(12) United States Patent
Sasai et al.

(10) Patent No.: US 8,273,570 B2
(45) Date of Patent: Sep. 25, 2012

(54) PROCESS OF INDUCING DIFFERENTIATION OF EMBRYONIC CELL TO CELL EXPRESSING NEURAL SURFACE MARKER USING OP9 OR PA6 CELLS

(75) Inventors: Yoshiki Sasai, Kyoto (JP); Shin-Ichi Nishikawa, Kyoto (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/855,587

(22) Filed: May 16, 2001

(65) Prior Publication Data

US 2002/0151056 A1 Oct. 17, 2002

Related U.S. Application Data

(60) Provisional application No. 60/257,049, filed on Dec. 20, 2000.

(30) Foreign Application Priority Data

May 16, 2000 (JP) .............................. P. 2000-144059
Sep. 25, 2000 (JP) .............................. P. 2000-290819

(51) Int. Cl.
C12N 5/071 (2010.01)
C12N 5/00 (2006.01)
C12N 5/02 (2006.01)

(52) U.S. Cl. ...................... 435/368; 435/375; 435/377

(58) Field of Classification Search .................. 435/325, 435/363, 366, 377, 383, 368, 373, 375
See application file for complete search history.

(56) References Cited

U.S. PATENT DOCUMENTS

| 5,753,506 A | 5/1998 | Johe ................................ 435/377 |
| 5,843,780 A * | 12/1998 | Thomson ....................... 435/363 |
| 6,114,168 A * | 9/2000 | Samarut et al. ................ 435/405 |
| 2002/0168763 A1* | 11/2002 | Yan et al. ...................... 435/325 |

FOREIGN PATENT DOCUMENTS

| WO | WO 99/27076 | 6/1999 |
| WO | WO 02/26941 | 4/2002 |

OTHER PUBLICATIONS

Moreadith, R.W. et al. Gene Targeting in Embryonic Stem Cells: The New Physiology and Metabolism. J. Mol. Med, 1997, 75:208-216.*
Mullins, L.J. et al. Molecular Medicine in Genetically Engineered Animals. J. Clin. Invest., 1997, 97:1557-1560.*
Pera, M.F. Human Embryonic Stem Cells. J. of Cell Science, 2000, 113:5-10.*
van Inzen, W.G. et al. Neuronal Differentiation of Embryonic Stem cells. Biochim et Biophys Acta (1996) 1312:21-26.*
Kalyani, A.J. et al. Spinal Cord Neuronal Precursors Generate Multiple Neuronal Phenotypes in Culture. The Journal of Neuroscience (1998) 18:7856-7868.*
Mizuseki et al. PNAS 100(10):5828-5833, May 2003.*
Kawasaki et al. Neuron 28(1):31-40, Oct. 2000.*
Thomson et al. Biol. Reprod. Aug. 1996;55(2):254-9 Pluripotent cell lines derived from common marmoset (*Callithrix jacchus*) blastocysts.*
Mizuseki et al, (PNAS, 100(10): 5828-5833, 2003.*
Lerou et al, (Blood Reviews, 19: 321-331, 2005).*
Nakano et al, (Science, 265: 1090-1101, 1994).*
Li et al (Nat Biotechnol. Feb. 2005;23(2):215-21).*
Allegrucci et al., 2006 (Human Reproduction Update, Vol. Advance Access published on Aug. 26, 2006, p. 1-18).*
Sato et al., 2003 (Developmental Biology, vol. 260, p. 404-413).*
Rao, M., 2004 (Developmental Biology, vol. 275, p. 269-286).*
Abeyta et al., 2004 (Human Molecular Genetics, vol. 13, No. 6, p. 601-608).*
Sasai Y., 2002 (Journal of Neurology, vol. 249, Supplement 2, p. II/41-II/44).*
Tropepe, et al., "Autonomous Neural Cell Fate Specification in Mouse Embryonic Stem Cell", Society for Neuroscience Abstracts, vol. 25, No. 1/2 (1999), p. 527.
Vescovi, et al., "Isolation and Cloning of Multipotential Stem Cells from the Embryonic Human CNS and Establishment of Transplantable Human . . . ", Experimental Neorology, vol. 156 (1999), pp. 71-83.
lzumi-Hisha, et al. "Monoclonal Antibodies Against a Preadipose Cell Line (MC3T3-G2/PA6) Which Can Support Hemopoiesis", Hybridoma, vol. 10, No. 1 (1991), pp. 103-112.
Lin, et al., "Expression of CD34 in endothelial cells, hematopoietic progenitors and nervous cells in fetal and adult mouse tissues", *Eur. J. Immunol.*, vol. 25, No. 6 (1995), pp. 1508-1516.
Hirami, et al., "Generation of retinal cells from mouse and human induced pluripotent stems cells", Neuroscience Letters, vol. 458 (2000) 126-31. Kim, et. al., "Robust Enhancement of Neural Differentiation from Human ES and iPS Cells Regardless of their Innate Difference in Differentiation Propensity", Stem Cell Rev and Rep, vol. 6 (2010) 270-81.
Osafune, et al., "Marked differences in differentiation propensity among human embryonic stem cell lines", Nature Biotechnology, vol. 26, No. 3 (2008) 313-15.
Osakada, et al., "Toward the generation of rod and cone photoreceptors from mouse, monkey and human embryonic stem cells", Nature Biotechnology, vol. 26, No. 2 (2008) 215-24.
Hirami, et al., "Generation of retinal cells from mouse and human induced pluripotent stems cells", Neuroscience Letters, vol. 458 (2009) 126-31.
Okabe, "Differentiation of Embryonic Stem Cells", Current Protocols in Neuroscience, Unit 3.6 (1997) 1-13.

* cited by examiner

*Primary Examiner* — Gerald Leffers, Jr.
*Assistant Examiner* — Magdalene Sgagias
(74) *Attorney, Agent, or Firm* — Fitzpatrick, Cella, Harper & Scinto

(57) ABSTRACT

A method for inducing differentiation of an embryonic stem cell into an ectodermal cell and an ectoderm-derived cell, which comprises culturing the embryonic stem cell under non-aggregation conditions; a medium and a medium supernatant used in the method; an agent for inducing differentiation used in the method; a stroma cell or a stroma cell-derived factor having activity of inducing differentiation in the method; an antibody which specifically recognizes the stroma cell; an antigen which recognizes the antibody; a cell induced by the method; a method for evaluating or screening a substance relating to the regulation in a differentiation step from an embryonic stem cell into an ectodermal cell or an ectoderm-derived cell by carrying out the method; and a medicament comprising the stroma cell, the stroma cell-derived cell, the antibody, the antigen or the cell.

18 Claims, 10 Drawing Sheets

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Synthetic
      DNA

<400> SEQUENCE: 1
tgaagagagc ggacaaggag atc                                           23

<210> SEQ ID NO 2
<211> LENGTH: 24
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Synthetic
      DNA

<400> SEQUENCE: 2
tctggagtta agaaatcgga gctg                                          24

<210> SEQ ID NO 3
<211> LENGTH: 19
<212> TYPE: DNA
<213> ORGANISM: Artificial Sequence
<220> FEATURE:
<221> NAME/KEY:
```

```
<222> LOCATION:
<223> OTHER INFORMATION: Description of Artificial Sequence: Synthetic
      DNA

<400> SEQUENCE: 3
aggacggctc tctgaagaa                                                      19

<210> SEQ ID NO 4
<211> LENGTH: 20
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Synthetic
      DNA

<400> SEQUENCE: 4
ttgaccgagt tgaaggcgaa                                                     20

<210> SEQ ID NO 5
<211> LENGTH: 22
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Synthetic
      DNA

<400> SEQUENCE: 5
gaccacagtc catgccatca ct                                                  22

<210> SEQ ID NO 6
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Synthetic
      DNA

<400> SEQUENCE: 6
tccaccaccc tgttgctgta g                                                   21
```

PROCESS OF INDUCING DIFFERENTIATION OF EMBRYONIC CELL TO CELL EXPRESSING NEURAL SURFACE MARKER USING OP9 OR PA6 CELLS

This application is a non-provisional application of provisional application No. 60/257,049 filed Dec. 20, 2000.

BACKGROUND OF THE INVENTION

1. Field of the Invention

The present invention relates to a process for inducing differentiation of an embryonic stem cell into a functional cell. More particularly, the present invention relates to a process for inducing differentiation of an embryonic stem cell into an ectodermal cell or an ectoderm-derived cell useful for cell medical treatment, the differentiation-induced cell and use thereof. Also, the present invention relates to a medium used in the above process, an antibody which specifically recognizes a stroma cell in the above process, an antigen recognized by the antibody and use thereof.

2. Brief Description of the Background Art

In general, an embryonic stem cell means a cell which can be cultured in vitro and can also differentiate into all cells including germ cells when injected into the vacuole of an embryo before implantation, such as blastocyst, of other individual, and is called an embryonic stem cell or an ES cell.

Relationship between the generation of the initial stage embryo and the embryonic stem cell is described below using mouse as an example.

While moving from the oviduct to the uterus, a mouse fertilized egg repeats its division into 2 cells, 4 cells and 8 cells, generates compaction in which adhesion among cells is increased when it becomes the 16-cell stage, and reaches the stage called morula where borders among cells become unclear. In addition, 3.5 days after fertilization, a space called blastcoel is formed inside the embryo and becomes blastocyst. The blastocyst of this stage comprises the outer trophectogerm layer and inner cell mass (ICM). The blastocyst is implanted onto the uterus wall spending at 4.5 to 5.5 days after fertilization. At the stage of implantation, surface cells facing the blastcoel in the inner cell mass are differentiated into primitive endoderm cells. A part of these cells separates from the embryo itself, migrates into inside of the trophectoderm layer and becomes parietal endoderm cells to form Reichert's membrane by secreting an extracellular matrix.

On the other hand, the primitive endodermal cells around the embryonic part form a cell layer called visceral endoderm. These parietal and visceral endoderms then become a supporting tissue for protecting the fetus itself and exchanging nourishment and waste matter between it and the mother body. Cells of the inner cell mass, which form the fetus body in the future, proliferate and form a cell layer called primitive ectoderm. The primitive ectoderm is also called embryonic ectoderm or epiblast. Since the embryo after implantation grows into a cylindrical form as a whole, the embryo after 5.5 to 7.5 days of implantation is called egg cylinder. In half of the base side of the egg cylinder to the uterus, an extraembryonic tissue which forms the placenta in the future is formed by differentiating from the trophectoderm. After 6.5 days of fertilization, a groove called primitive streak appears on the primitive ectoderm layer, and, in this part, the primitive ectoderm enters into a space between the primitive ectoderm layer and the visceral endoderm layer by changing to a mesenchymal cell-like form and migrates from the primitive streak toward all directions to form embryonic mesoderm. In this cell layer, cells which become the definitive endoderm of the fetus body in the future are also contained.

Thus, it is known that 3 germ layers of not only ectoderm but also mesoderm and endoderm of the fetus are produced from the primitive ectoderm, and that all tissues of the fetus are derived from the primitive ectoderm. Also, It has been found that cells of the nervous system and the epidermal system are formed from ectoderms, and the ectoderm destined to differentiate into nervous system cells is called neuroectoderm (neural ectoderm), and the ectoderm destined to differentiate into epidermal system cells is called non-neuroectoderm.

Among the cell lineage in the embryo generation process described above, individual blastomere staring from fertilized egg to morula, cells of the inner cell mass in the blastocyst and cells constituting the primitive ectoderm layer have a totipotency and have properties as undifferentiated embryonic stem cells. When a primitive ectoderm starts its differentiation into each germ layer, most of its cells lose the totipotency, but a part of them is left as a primordial germ cell which takes part in transmitting genes to the next generation. When the primitive ectoderm is differentiated into each germ layer, the primordial germ cell migrates in the rear together with the embryonic mesoderm layer invaginating from the primitive streak and appears in a specific region of the extraembryonic mesoderm at the base of allantois. The primordial germ cell then migrates toward the gonad primordium and forms an ovum or a spermatozoon according to the sexual differentiation of gonad.

The embryonic stem cell can be established by culturing the inner cell mass-constituting undifferentiated stem cell existing in the inside of blastocyst and frequently repeating dissociation and subculturing of the cell mass. It is known that the cell can repeat proliferation and subculture almost unlimitedly while maintaining its normal karyotype and has a pluripotency of differentiating into every type of cells just as the same as the inner cell mass.

When an embryonic stem cell is injected into the blastocyst of other individual, it is mixed with the cell of inner cell mass of the host embryo and forms a chimeric individual by contributing to the formation of embryo and fetus. In an extreme case, an individual fetus body mostly composed of the only embryonic stem cell injected can be produced. Among chimeric individuals, an individual in which the injected embryonic stem cell has contributed to the formation of a primordial germ cell which will produce an egg or a sperm in the future is called germ line chimera, and since an individual derived from the injected embryonic stem cell can be obtained by crossing the germ line chimera, it has been confirmed that the embryonic stem cell has a totipotency of differentiating into all cells (*Manipulating the Mouse Embryo, A Laboratory Manual*, Second Edition, Cold Spring Harbor Laboratory Press (1994) (hereinafter referred to as "*Manipulating the Mouse Embryo, A Laboratory Manual*"); *Gene Targeting, A Practical Approach*, IRL Press at Oxford University Press (1993) (hereinafter referred to as "*Gene Targeting*"); Biomanual Series 8, *Gene Targeting, Production of Mutation Mouse Using ES Cell*, Yodo-sha (1995) (hereinafter referred to as "*Production of Mutation Mouse Using ES Cell*")).

When the inner cell mass of blastocyst is cultured like the usual primary culture, it directly differentiates into a fibroblast-like cell in most cases. In order to culture it while maintaining undifferentiated conditions, it is necessary in general to use a primary fibroblast cell produced from the fetus or STO cell derived from an SIHM mouse as a feeder cell (*Gene Targeting, Production of Mutation Mouse Using ES Cell*). By keeping an appropriate cell density on the feeder cell and repeating dissociation and subculture of the cell mass while frequently exchanging the culture medium, it becomes possible to maintain the conditions while keeping properties of the undifferentiated stem cell (*Manipulating the Mouse Embryo, A Laboratory Manual*).

As a factor for maintaining undifferentiated conditions of an embryonic stem cell, LIF (leukemia inhibitory factor) has been identified (A. G. Smith and M. L. Hooper, *Dev. Biol.*, 121, 1 (1987); A. G. Smith et al., *Nature*, 336, 688 (1988); P. D. Rathjen et al., *Genes Dev.*, 4, 2308 (1990)), and it has been reported that an embryonic stem cell having a totipotency can be isolated and cultured without using a feeder cell when LIF is added to the culture medium (J. Nichols et al., *Development*, 110, 1341 (1990); S. Pease et al., *Dev. Biol.*, 141, 344 (1990)). Also, it has been shown that the addition of a family molecule of interleukin 6 sharing a subunit gp130 of LIF receptor as the common receptor is effective, instead of adding LIF itself to the culture medium (D. P. Gearing and G. Bruce, *New Biol.*, 4, 61 (1992); J. I. Conover et al., *Development*, 119, 559 (1993); C. Piquet-Pellorce et al., *Exp. Cell Res.*, 213, 340 (1994); D. Pennica et al., *J. Biol. Chem.*, 270, 10915 (1995)).

In addition, since it has been reported that an embryonic stem cell capable of contributing to the formation of a germ line cell by maintaining undifferentiated conditions of the embryonic cell was established by jointly using interleukin 6 capable of directly activating gp130 and a soluble interleukin 6 receptor (K. Yoshida et al., *Mech. Dev.*, 45, 163 (1994); J. Nichols et al., *Exp. Cell Res.*, 215, 237 (1994); Japanese Published Unexamined Patent Application No. 51060/95, It has been found that intracellular signal transduction from gp130 is playing an important role in maintaining the pluripotency and undifferentiation of the embryonic stem cell. This is supported also by a fact that normal generation of initial stage embryo is observed in a deficiency mouse whose LIF gene and LIF receptor gene were destroyed using gene targeting techniques (C. L. Stewaet et al., *Nature*, 359, 76 (1992); J. L. Escary et al., *Nature*, 363, 361 (1993); M. Li et al., *Nature*, 378, 724 (1995); C. B. Ware et al., *Development*, 121, 1283 (1995)), but fetal death occurs during a period from the fetal age of 12.5 days to birth in a mouse whose gp130 gene was destroyed (K. Yoshida et al., *Proc. Natl. Acad. Sci. USA*, 93, 407 (1996)).

Since the first establishment of an embryonic stem cell in mice (M. J. Evans et al, *Nature*, 292, 154 (1981); G. R. Martin, *Proc. Natl. Acad. Sci. USA*, 78, 7634 (1981)), methods for establishing efficient embryonic stem cells such as methods for establishing embryonic stem cells in non-mice (U.S. Pat. No. 5,453,357; U.S. Pat. No. 5,670,372) have been studied, and embryonic stem cells have so far been established in rat (P. M. Iannaccone et al., *Dev. Biol.*, 163, 288 (1994)), in domestic fowl (B. Pain et al., *Development*, 122, 2339 (1996); U.S. Pat. No. 5,340,740; U.S. Pat. No. 5,656,479)), in pig (M. B. Wheeler, *Reprod. Fertil. Dev.*, 6, 563 (1994); H. Shim et al., *Biol. Reprod.*, 57, 1089 (1997)), in monkey (J. A. Thomson et al., *Proc. Natl. Acad. Sci. USA*, 92, 7844 (1996)) and in human (J. A. Thomson et al., *Science*, 283, 1145 (1998); M. J. Shamblott et al., *Proc. Natl. Acad. Sci. USA*, 95, 13726 (1998)).

It is known that a teratoma in which various tissues are mixed is formed when an embryonic stem cell is transplanted, e.g., under the skin of an animal of the same line of the embryonic stem cell (*Manipulating the Mouse Embryo, A Laboratory Manual*).

Also, it has been reported that, in in vitro culturing, various cells such as endodermal cells, ectodermal cells, mesodermal cells, blood cells, endothelial cells, cartilage cells, skeletal muscle cells, smooth muscle cells, heart muscle cells, glial cells, nerve cells, epithelial cells, melanocytes and keratinocytes can be formed by inducing differentiation through the formation of a cell mass called embryoid body (hereinafter referred to as "EB") in which embryonic stem cells are once aggregated to form a pseudo-embryonic state (P. D. Rathjen et al., *Reprod. Fertil. Dev.*, 10, 31 (1998)). However, in the differentiation induction by this culturing method, spontaneous differentiation is generated by the formation of cell aggregation mass and, as a result, appearance of the intended cell is observed. Accordingly, it does not result in the efficient induction of a specified cell group and appearance of a variety of tissue cells is simultaneously observed.

Various attempts have been made for methods for efficiently inducing differentiation of nervous system cells from the embryonic stem cell.

It has been reported that expression of a transcription factor Pax3 and neurofilament important for the differentiation of nervous system cells is significantly increased when culturing of the stem cell after formation of EB is continued using a medium supplemented with NGF (nerve growth factor) on a glass dish coated with poly-L-lysine or laminin (G. Yamada et al., *Biochem. Biophys. Res. Commun.*, 199, 552 (1994)). Based on the information that differentiation of an EC cell which will be described later into nervous system is accelerated by retinoic acid treatment (E. M. V. Jones-Villeneuve et al., *J. Cell Biol.*, 94, 253 (1982); G. Bain et al., *BioEssays*, 16, 323 (1994)), its effect on embryonic stem cells has also been examined, and it has been reported that a neuron-like cell which generates action potential by developing axons appears at a high ratio of about 40%, when EB is cultured for 4 days in the presence of retinoic acid and then treated with trypsin to carry out monolayer culturing, and that expression of class III tubulin, neurofilament M subunit, GAP-43 (growth-associated protein-43) as a substrate of nerve-specific calmodulin binding kinase C, γ-aminobutyric acid (hereinafter referred to as "GABA") receptor, NMDA (N-methyl-D-aspartate) receptor and synapsin is observed in this cell at a protein level, and expression of neurofilament L subunit, glutamic acid receptor, tyrosine hydroxylase, a transcription factor Brn-3, GFAP (glial fibrillary acidic protein) and a GABA synthesizing enzyme GAD (glutamic acid decarboxylase) is observed at a mRNA level (G. Bain et al., *Dev. Biol.*, 168, 342 (1995); F. A. Michael et al., *J. Neurosci.*, 16, 1056 (1996)).

Since it is known that Brn-3 is expressed in central nervous system (X. He et al., *Nature*, 340, 35 (1989)), and GAP-43 is expressed in nerve axon (L. I. Benowitz and A. Routtenberg, *Trends Neurosci.*, 20, 84 (1997)), MAP-2 is expressed in nerve dendrite (L. I. Binder et al., *Ann. NY Acad. Sci.*, 76, 145 (1986)), GFAP is expressed in glial cell (A. Bignami et al., *Brain Res.*, 43, 429 (1972)), GABA receptor and GAD are expressed in inhibitory nerve (Y. Chang and D. I. Gottlieb, *J. Neurosci.*, 8, 2123 (1988)) and glutamic acid receptor and NMDA receptor are expressed in excitatory, nerve, it is shown that signals of differentiation into various nervous system cells are simultaneously transmitted when the differentiation is induced using retinoic acid.

Also, it has been reported that differentiating induction to nervous cells was not observed when retinoic acid was simply allowed to react directly with embryonic stem cells without mediating the interaction of cells by EB formation (H. G. Slager et al., *Dev. Gen.*, 14, 212 (1993)). It has been reported that, when $10^{-7}$ mol/l retinoic acid was allowed to react with monolayer-cultured embryonic stem cells, expression of GAP-43 was observed in about 50% of the cells 3 days thereafter, and expression of neurofilament-165 (S. H. Yen and K. L. Fields, *J. Cell Biol.*, 88, 115 (1981)) in less than 5% of the cells 4 to 5 days thereafter, both at protein level, but most of the GAP-43 positive cells showed an endodermal cell-like form (W. G. van Inzen et al., *Biochim. Biophys. Acta.*, 1312, 21 (1996)). It has been reported that a part of the GAP-43 positive cells show a glial cell-like morphology and about half thereof are neurofilament-165 positive cells, but both of the GAP-43 and neurofilament-165 have lower staining degree by antibody staining than the nervous cells induced by retinoic acid treatment after EB formation (W. G. van Inzen et al., *Biochim. Biophys. Acta.*, 1312, 21 (1996)). Thus, it has been confirmed that the interaction among cells by EB formation is necessary for the efficient differentiation induction of nervous system cells.

In addition, it has been reported that, when action potential of the cells having glial cell-like morphology was measured using a patch clamp method, generation of the potential by 5-HT (5-hydroxytryptamin)-, GABA-, kainic acid-, glutamic acid-, dopamine- or carbachol-stimulation was observed in about half of the examined cells, but generation of action potential by carbachol-stimulation was not observed in the neuron-like cells induced by retinoic acid treatment after EB formation, used as a control, instead, generation of action potential by noradrenaline-stimulation was observed, thus showing that the interaction among cells by EB formation is also important for the determination of the direction of differentiation of nerve cells (W. G. van Inzen et al., *Biochim. Biophys. Acta.*, 1312, 21 (1996)). It is known that the cell layer on the EB surface differentiates into a primitive endoderm-like form in the EB formation by cell aggregation and it is considered that the differentiation is induced by a certain interaction between the cell layer and inner undifferentiated cells, but its factor has not specifically been identified (P. D. Tathjen et al., *Reprod. Fertil. Dev.*, 10, 31 (1998)).

Thereafter, as a result of further detailed analysis of the effect of retinoic acid on embryonic stem cells, it has been found that, when EB formed in a medium supplemented with retinoic acid is cultured in a dish for tissue culture, a nestin-positive precursor cell common for neuron and glial cells firstly appears, and then cells differentiated into GABAergic nerve cells, cholinergic nerve cells, GFAP positive astrocytes, and O4 positive (M. Schachner et al., *Dev. Biol.*, 83, 328 (1981)) oligodendrocytes appear (A. Fraichard et al., *J. Cell Sci.*, 108, 3181 (1995)).

Differentiation of neuron and glial cells from nestin-positive common precursor cells in the living body has been suggested by a labeling test using retrovirus (U. Lendahl et al., *Cell*, 60, 585 (1990); J. Price et al., *Development Supplement*, 2, 23 (1991); J. Price et al., *Brain Pathol.*, 2, 23 (1992)), and then confirmed by the isolation of a precursor cell existing in the brain of the living body as a nervous system stem cell (S. J. Morrison et al., *Cell*, 88, 287 (1997); R. D. G. McKay, *Science*, 276, 66 (1997)).

However, when retinoic acid is used for the differentiation induction of an embryonic stem cell, it is used at a markedly higher concentration (10 to 100 times) than the physiologically existing concentration. Since the use of retinoic acid at a concentration higher than the physiologically existing concentration is disliked from the toxicity point of view, it is difficult to use the obtained cell in transplantation. Accordingly, attempts have been made to induce an embryonic stem cell into a nervous system cell under conditions more close to the physiological conditions without using retinoic acid.

The following has been reported. A nestin-positive and fatty acid binding protein (which is expressed in the brain)-positive (A. Kurtz et al., *Development*, 120, 2637 (1994)) nerve epithelial cell-like precursor cell (neuroepithelial precursor cell) is induced, when EB formed by 4 days of suspension culturing is adhered onto a tissue culture dish by 1 day of culturing and then cultured for 5 to 7 days using an ITSFn medium comprising insulin, transferrin, selenium chloride and fibronectin (A. Rizzino and C. Growley, *Proc. Natl. Acad. Sci. USA*, 77, 457 (1980)), and the precursor cell grows keeping as the precursor cell when cultured using an mN3 serum-free medium comprising bFGF (basic fibroblast growth factor) and laminin, but it differentiates into a central nervous system cell and a glial cell when cultured using the medium from which bFGF is removed, and synaptogenesis of excitatory nervous system and inhibitory nervous system is observed when culturing is continued using a serum-supplemented medium (S. Okabe et al., *Mech. Dev.*, 59, 89 (1996)).

A possibility for the nervous system cell induced in vitro in this manner to function normally in the living body has also been examined.

It has been observed that when the mouse epithelial cell-like precursor cell induced using the ITSFn medium is transplanted into the cerebral ventricle of a rat of 16 to 18 days of fetal age, the transplanted precursor cell migrates to be incorporated by the brain tissue and differentiates into a nerve cell, an astrocyte and an oligodendrocyte, but they cannot be distinguished from the host cell morphologically (O. Brustle et al., *Proc. Natl. Acad. Sci. USA*, 94, 14809 (1997)). However, formation of teratoma tissues which are not observed in the original tissue is observed in the transplanted region, such as formation of a neural tube-like structural body actively repeating cell division and a small cluster of alkaline phosphatase positive undifferentiated cells.

Formation of such teratoma tissues has also been observed in the transplantation of a nervous system precursor cell induced from embryonic stem cell using retinoic acid (J. Dinsmore et al., *Cell, Transplant.*, 5, 131 (1996); T. Deacon et al., *Exp. Neurol.*, 149, 28 (1998)).

Thereafter, it has been reported that repair of myelin sheath was observed without forming teratoma, when a precursor cell of a glial cell was induced from embryonic stem cells and the glial precursor cell was transplanted into the brain or spinal cord of a rat congenitally lacking myelin sheath (O. Brustle et al., *Science*, 285, 754 (1999)). In this transplantation, a further differentiated glial cell precursor cell was induced from the above-mentioned nerve epithelial cell-like precursor cell induced using an ITSFn medium after the EB formation and used in the transplantation.

That is, it is shown that the cell differentiation-induced in this manner can be used in the transplantation, because differentiation into a glial precursor cell can be induced by culturing the induced nerve epithelial cell-like precursor cell for 5 days on a dish coated with polyornithine in a medium containing insulin, transferrin, progesterone, putrescine, selenium chloride, FGF2 (fibroblast growth factor 2) and laminin, pealing the cells using Hanks' buffer which does not contain calcium and magnesium, subculturing the cells at a cell density of ⅕ in a medium containing FGF2 and EGF (epidermal growth factor) and then, when the cells reached confluent, continuing the subculture at a cell density of ⅕ in a medium comprising FGF2 and PDGF-AA (platelet-derived growth factor-AA). It has been found that the cell differentiation-induced in this manner is a glial precursor cell, because it is A2B5-positive (M. C. Raff et al., *Nature*, 303, 390 (1983)) and its differentiation into an astrocyte and an oligodendrocyte is observed in vitro when cultured using a medium which does not comprise FGF2 and EGF.

Regarding cells having functions similar to the embryonic stem cell, their relationships with the embryonic stem cell are described below.

Various embryonal carcinoma cells (EC cells) have been established from a malignant teratoma (teratocarcinoma), as cell lines having a pluripotency like the case of an embryonic stem cell (M. J. Evans, *J. Embryol. Exp. Morph.*, 28, 163 (1972)).

These cells are considered to be cells having the properties of an embryonic stem cell as an undifferentiated stem cell, because they express a gene to be used as a marker of an embryonic stem cell (E. G. Bernstine et al., *Proc. Natl. Acad. Sci. USA*, 70, 3899 (1973); S. B. Diwan and L. C. Steven, *J. Natl. Cancer Inst.*, 57, 937 (1976); D. Solter and B. B. Knowles, *Proc. Natl. Acad. Sci. USA*, 75, 5565 (1978); B. A. Hosler et al., *Mol. Cell. Biol.*, 9, 5623 (1989); S. C. Pruitt, *Development*, 120, 37 (1994)), they are capable of differentiating into various cells in vitro (G. R. Martin and M. J. Evans, *Cell*, 6, 467 (1975); G. R. Martin and M. J. Evans, *Proc. Natl. Acad. Sci. USA*, 72, 1441 (1975); M. W. McBurney, *J. Cell. Physiol.*, 89, 441 (1976)), teratoma is formed from various tissues by their transplantation into congenic individuals (L. J. Kleinsmith and G. B. Pierce, *Cancer Res.*, 24, 797 (1964)), they form chimeric individuals by contributing to fetus formation when injected into a blastocyst (B. Mintz and K. Illmensee, *Proc. Natl. Acad. Sci. USA*, 72, 3538 (1975); V. E. Papaioannou et al., *Nature*, 258, 70 (1975); M. J. Dewey et al., *Proc. Natl. Acad. Sci. USA*, 74, 5564 (1977)) and, although it is extremely rare, an example is reported on an embryonal carcinoma cell line capable of producing a germ line chimera (T. A. Stewart and B. Mintz, *Proc. Natl. Acad. Sci. USA*, 78, 7634 (1981)).

Also, it was shown that a cell line of a cell analogous to an embryonic stem cell appeared when bFGF was added in culturing a primordial germ cell, and was established as an EG cell (embryonic germ cell) (Y. Matsui et al., *Cell*, 70, 841 (1992); J. L. Resnic et al., *Nature*, 359, 550 (1992)). It has been found that this EG cell is capable of contributing to the formation of a germ line chimera (C. L. Stewart et al., *Devel. Biol.*, 161, 626 (1994); P. A. Labosky et al., *Development*, 120, 3197 (1994)) and has the properties as the undifferentiated stem cell possessed by the embryonic stem cell. Since undifferentiated stem cells and germ cells have fairly common properties, it is considered that they can be mutually converted relatively easily, by changes in the controlling conditions of proliferation and differentiation.

On the other hand, with the advance in developmental engineering, possibility of preparing an embryonic stem cell of individual human has been reported. Since the creation of a sheep, Dolly, as a somatic cell nucleus-derived clone individual for the first time in an mammal by Wilmut et al. in 1997 (Wilmut et al., *Nature*, 385, 810 (1997)), creation of a cloned calf using the nucleus of a fetal cell (J. B. Cibelli et al., *Science*, 280, 1256 (1998)), a cloned calf using the nucleus of a skin, muscle, ear capsule, oviduct or proligerous cumulus cell (A. Iritani, Protein, *Nucleic Acid and Enzyme*, 44, 892 (1999)), a cloned goat (A. Baguisi et al., *Nature Biotechnology*, 17, 456 (1999)), a cloned mouse using the nucleus of proligerous cumulus cell (T. Wakayama et al., *Nature*, 394, 369 (1998)), a cloned mouse using a cell of male tail (T. Wakayama et al., *Nature Genetics*, 22, 127 (1999)) and a cloned mouse using the nucleus of embryonic stem cell (T. Wakayama et al., *Proc. Natl. Acad. Sci. USA*, 96, 14984 (1999); W. M. Rideout III et al., *Nature Genetics*, 24, 109 (2000)) has been reported, thus showing a possibility of creating cloned individuals of mammals by introducing the nucleus of a somatic cell into enucleated oocytes. Since it is possible to prepare an embryonic stem cell of individual human by combining this nucleus transplantation technique with a technique for establishing the embryonic stem cell, a possibility of applying it to organ plantation as a cell medical treatment has been pointed out (R. P. Lanza et al., *Nature Medicine*, 5, 975 (1999)). Also, it has been pointed out that it is possible to carry out more effective gene therapy by applying gene manipulation to an embryonic stem cell and to modify histocompatibility antigens (P. D. Rathjen et al., *Reprod. Fertil. Dev.*, 10, 31 (1998)).

Next, effectiveness of the cell medical treatment in organ transplantation is described with examples.

Parkinson disease is a chronic progressive disease mainly caused by the degeneration of dopaminergic neurons of substantia nigra corpus striatum. A perlingual therapy mainly using L-DOPA (L-dihydroxyphenylalanine) has conventionally been carried out, but since it is necessary to carry out its internal use for a prolonged period of time, its effect gradually attenuates in many patients who then will suffer from side effects such as wearing off phenomenon, dyskinesia and the like. Accordingly, development of more effective therapeutic methods has been attempted, and a treatment for transplanting an abortion fetal brain to patients of Parkinson disease has been started. In the whole world, several hundred cases of abortion fetal brain transplantation treatment have so far been carried out. Recently, a double blindfold test on the transplantation of abortion fetal brain cells was carried out in the United States for 40 patients of Parkinson disease, and its usefulness was confirmed. In addition, a case has been reported in which the transplanted cell was fixed for 10 years or more and the transplanted cell formed a synapse with corpus striatum in some patients who underwent such an abortion fetal brain cell transplantation. Thus, it has been understood that the cell treatment for transplanting the brain of abortion fetus shows high efficiency for Parkinson disease, but a protest against the use of abortion fetuses is strong due to ethical problems. In addition, since close to 10 fetuses are practically required for the treatment of one patient, it meets with a great obstacle for its realistic application to the therapy. Accordingly, concern has been directed toward the development of a method for preparing a dopaminergic neuron in a large amount by a commonly acceptable method.

In view of these backgrounds, development of a method for inducing differentiation of a target functional cell selectively and efficiently from an undifferentiated stem cell which can be cultured while maintaining its pluripotency has been drawing attention, and various attempts have been made thereon. However, development of a method for efficiently inducing differentiation of a cell group without accompanying formation of teratoma is not successful yet in many functional cells. Also, induction of a target functional cell under an artificially controlled physiological environment, such as culture conditions which do not use serum or retinoic acid, is desired from the viewpoint of cell medical treatment, but such a method is not known. Particularly, a method for obtaining an ectoderm-derived cell, specifically a dopaminergic neuron having normal functions, by efficient differentiation induction from an undifferentiated stem cell is important and desired from the viewpoint of the medical treatment of patients of brain diseases including Parkinson disease, but such a method has not been developed yet.

SUMMARY OF THE INVENTION

An object of the present invention is to provide a method for inducing differentiation of an ectodermal cell and an ectoderm-derived cell, applicable to cell and organ transplantation for medical treatments, selectively and efficiently from an embryonic stem cell, the differentiation-induced cell and use thereof.

Also, another object of the present invention is to provide a medium used in the method, for differentiation induction, an antibody which specifically recognizes a stroma cell to be used in the differentiation induction process and a method for producing the antibody, an antibody obtained thereby, a method for obtaining an antigen recognized by the antibody, an antigen obtained thereby and use thereof.

As a result of intensive studies on various culture conditions capable of inducing differentiation of embryonic stem cells, the present inventors have succeeded in finding a selective and efficient method for inducing differentiation of an ectodermal cell and an ectoderm-derived cell from embryonic stem cell, thereby resulting in the accomplishment of the present invention.

The present invention relates to the following (1) to (71).

(1) A method for inducing differentiation of an embryonic stem cell into an ectodermal cell, which comprises culturing the embryonic stem cell under non-aggregation conditions.

(2) The method according to (1), wherein the ectodermal cell is a cell capable of differentiating into a nervous system cell or an epidermal system cell.

(3) A method for inducing differentiation of an embryonic stem cell into an ectoderm derived cell, which comprises culturing the embryonic stem cell under non-aggregation conditions.

(4) The method according to (3), wherein the ectoderm-derived cell is a nervous system cell or an epidermal system cell.

(5) The method according to (4), wherein the epidermal system cell is an epidermal cell.

(6) The method according to (4), wherein the nervous system cell is a cell selected from the group consisting of the following (a), (b), (c) and (d):
 (a) a neural stem cell;
 (b) a nerve cell;
 (c) a cell of neural tube; and
 (d) a cell of neural crest.

(7) The method according to (6), wherein the neural stem cell is a neural stem cell expressing nestin.

(8) The method according to (6), wherein the nerve cell is a nerve cell selected from the group consisting of the following (a), (b), (c) and (d):
 (a) a dopaminergic neuron;
 (b) an acetylcholinergic neuron;
 (c) a γ-aminobutyratergic neuron; and
 (d) a serotonergic neuron.

(9) The method according to (8), wherein the acetylcholinergic neuron is a motor nerve cell expressing islet 1.

(10) The method according to (6), wherein the cell of neural tube is a cell selected from the group consisting of the following (a), (b), (c) and (d):
 (a) a cell of neural tube before determination of dorsoventral axis, which is capable of differentiating into a cell positioned at the ventral side by reacting with sonic hedgehog as a ventral factor of neural tube and of differentiating into a cell positioned at the dorsal side by reacting with bone morphogenetic protein 4 as a dorsal factor of neural tube;
 (b) a cell of the neural tube ventral side, expressing HNF-3β (hepatocyte nuclear factor-3β) positioned on the basal plate of the most ventral side of neural tube;
 (c) a cell of the neural tube ventral side, expressing a marker Nkx2.2 existing secondary to the HNF-3β (hepatocyte nuclear factor-3β) from the ventral side of neural tube; and
 (d) a cell of the neural tube dorsal side, expressing Pax-7.

(11) The method according to (6), wherein the cell of neural crest is a cell expressing AP-2 (activator protein 2).

(12) The method according to any one of (1) to (11), wherein said culturing is carried out in the presence of bone morphogenetic protein 4.

(13) The method according to any one of (1) to (12), wherein said culturing is carried out in the presence of sonic hedgehog.

(14) The method according to any one of (1) to (13), wherein the non-aggregation conditions are conditions not mediating an embryoid body.

(15) The method according to any one of (1) to (14), which further comprises culturing under serum-free culture conditions.

(16) The method according to any one of (1) to (15), wherein said culturing is carried out in the presence of a stroma cell-derived factor.

(17) The method according to any one of (1) to (16), wherein said culturing is carried out in the presence of a stroma cell.

(18) The method according to (17), wherein the stroma cell is a stroma cell whose proliferation potency is deleted by a physicochemical treatment.

(19) The method according to (18), wherein the physicochemical treatment is selected from the group consisting of the following (a), (b) and (c):
 (a) a treatment with an antitumor agent;
 (b) a treatment by an radiation irradiation; and
 (c) a treatment for tissue fixation used in pathologic diagnosis.

(20) The method according to (19), wherein the antitumor agent is selected from the group consisting of mitomycin C, 5-fluorouracil, adriamycin and methotrexate.

(21) The method according to (19), wherein the treatment for tissue fixation used in pathologic diagnosis is selected from the group consisting of a microwave fixation, a rapid freeze-substitution fixation, a glutaraldehyde fixation, a p-formaldehyde fixation, a formalin fixation, an acetone fixation, a Van fixation, a periodic acid fixation, a methanol fixation and an osmic acid fixation.

(22) The method according to any one of (16) to (21), wherein the stroma cell is recognized by a monoclonal antibody produced by a hybridoma FERM BP-7573.

(23) The method according to any one of (16) to (22), wherein the stroma cell is selected from the group consisting of the following (a), (b), (c), (d), (e), (f) and (g):
 (a) a fetal primary culture fibroblast;
 (b) an SIHM mouse-derived STO cell;
 (c) a mouse fetus-derived NIH/3T3 cell;
 (d) an M-CSF deficient mouse calvaria-derived OP9 cell;
 (e) a mouse calvaria-derived MC3T3-G2/PA6 cell;
 (f) an embryonic stem cell-derived stroma cell; and
 (g) a bone marrow mesenchymal stem cell-derived stroma cell.

(24) The method according to any one of (1) to (23), wherein the embryonic stem cell is selected from the group consisting of the following (a), (b) and (c):
 (a) an embryonic stem cell established by culturing an early embryo before implantation;
 (b) an embryonic stem cell established by culturing an early embryo produced by nuclear transplantation of the nucleus of a somatic cell; and (c) an embryonic stem cell in which a gene on the chromosome of the embryonic stem cell of (a) or (b) is modified using a gene engineering technique.

(25) The method according to any one of (1) to (24), wherein said culturing is carried out in the absence of retinoic acid.

(26) The method according to any one of (1) to (25), wherein the embryonic stem cell is differentiated into an ectodermal cell or an ectoderm-derived cell at an efficiency of 5% or more.

(27) The method according to any one of (1) to (26), which does not substantially accompany differentiation induction of a mesodermal system cell.

(28) A medium for inducing differentiation of an embryonic stem cell into an ectodermal cell or an ectoderm-derived cell, which is used in the method of any one of (1) to (27).

(29) A stroma cell-derived factor which induces differentiation of an embryonic stem cell into an ectodermal cell or an ectoderm-derived cell.

(30) The factor according to (29), which is capable of adsorbing a mucopolysaccharide.

(31) The factor according to (30), wherein the mucopolysaccharide is heparin.

(32) An agent for inducing differentiation of an ectodermal cell into an epidermal system cell, which comprises, as an active ingredient, bone morphogenetic protein 4.

(33) An agent for inducing differentiation of an embryonic stem cell into an ectodermal cell or an ectoderm-derived cell, which comprises, as an active ingredient, a stroma cell which has activity of inducing differentiation of an embryonic stem cell into an ectodermal cell or an ectoderm-derived cell, or a factor derived from the cell.

(34) The agent according to (33), wherein the stroma cell is the stroma cell described in any one of (18) to (23).

(35) The agent according to (34), wherein the stroma cell-derived factor is capable of adsorbing a mucopolysaccharide.

(36) The agent according to (35), wherein the mucopolysaccharide is heparin.

(37) A medium which comprises a culture supernatant obtained by culturing a stroma cell which has activity of inducing differentiation of an embryonic stem cell into an ectodermal cell or an ectoderm-derived cell in a medium comprising a mucopolysaccharide.

(38) The medium which comprises a culture supernatant according to (37), wherein the stroma cell is the stroma cell described in any one of (18) to (23).

(39) The medium which comprises a culture supernatant according to (37) or (38), wherein the mucopolysaccharide is heparin.

(40) An agent for inducing differentiation of an ectodermal cell or an ectoderm-derived cell, which comprises, as an active ingredient, the culture supernatant described in any one of (37) to (39).

(41) A method for obtaining an antibody which specifically recognizes a stroma cell which has activity of inducing differentiation of an embryonic stem cell into an ectodermal cell or an ectoderm-derived cell, which comprises using a stroma cell as an antigen.

(42) The method according to (41), wherein the stroma cell is a stroma cell described in any one of (18) to (23).

(43) An antibody which specifically recognizes a stroma cell which has activity of inducing differentiation of an embryonic stem cell into an ectodermal cell or an ectoderm-derived cell, which is obtained by the method according to (41) or (42).

(44) A monoclonal antibody produced by a hybridoma FERM BP-7573.

(45) A method for obtaining an antigen recognized by the antibody according to (43) or (44), which comprises using the antibody.

(46) An antigen recognized by the antibody according to (43) or (44), which is obtained by the method according to (45).

(47) A medium for culturing a cell, which comprises the antigen according to (46).

(48) A method for obtaining a stroma cell-derived factor which has activity of inducing differentiation of an embryonic stem cell into an ectoderm-derived cell, which comprises using, as an index, the activity of inducing differentiation of an embryonic stem cell into an ectodermal cell or an ectoderm-derived cell.

(49) The method according to (48), which further comprises:
absorbing a mucopolysaccharide to a stroma cell-derived factor; and
the stroma cell-derived factor from the factor absorbing on the mucopolysaccharide.

(50) The method according to (48) or (49), wherein the stroma cell is a stroma cell described in any one of (18) to (23).

(51) The method according to (49), wherein the mucopolysaccharide is heparin.

(52) An ectodermal cell or an ectoderm-derived cell, which is induced by using the method according to any one of (1) to (27).

(53) A method for increasing purity of a cell which is differentiation-induced from an embryonic stem cell, which comprises culturing the ectodermal cell or ectoderm-derived cell according to (52) in a medium comprising an antitumor agent.

(54) The method according to (53), wherein the antitumor agent is selected from the group consisting of mitomycin C, 5-fluorouracil, adriamycin, methotrexate and ara-C.

(55) A cell which is obtained by using the method according to (53) or (54).

(56) A method for evaluating a substance relating to the regulation in a differentiation step from an embryonic stem cell into an ectodermal cell or an ectoderm-derived cell, which comprises:
carrying out the method according to any one of (1) to (27) in the presence of a substance to be tested and the method in the absence of the substance to be tested; and
comparing the differentiation step from an embryonic stem cell into an ectodermal cell or an ectoderm-derived cell in the presence of the substance to be tested with that in the absence of the substance to be tested.

(57) A method for screening a substance relating to the regulation in a differentiation step from an embryonic stem cell into an ectodermal cell or an ectoderm-derived cell, which comprises:
carrying out the method according to any one of (1) to (27) in the presence of a substance to be tested and the method in the absence of the substance to be tested; and
comparing the differentiation step from an embryonic stem cell into an ectodermal cell or an ectoderm-derived cell in the presence of a substance to be tested with that in the absence of the substance to be tested.

(58) A method for evaluating a substance relating to the regulation of the function of an ectodermal cell or an ectoderm-derived cell, which comprises:
culturing the cell according to (52) in the presence of a substance to be tested and the cell in the absence of the substance to be tested; and
comparing the function of an ectodermal cell or an ectoderm-derived cell in the presence of the substance to be tested with that in the absence of the substance to be tested.
(59) A method for screening a substance relating to the regulation of the function of an ectodermal cell or an ectoderm-derived cell, which comprises:
culturing the cell according to (52) in the presence of a substance to be tested and that in the absence of the substance to be tested; and
comparing the function of the ectodermal cell or the ectoderm-derived cell in the presence of the substance to be tested with that in the absence of the substance to be tested.
(60) A medicament comprising a stroma cell having activity of inducing differentiation of an embryonic stem cell into an ectodermal cell or an ectoderm-derived cell, or a factor derived from the cell.
(61) The medicament according to (60), wherein the stroma cell is a stroma cell described in any one of (18) to (23).
(62) The medicament according to (60), wherein the factor is capable of adsorbing a mucopolysaccharide.
(63) The medicament according to (62), wherein the mucopolysaccharide is heparin.
(64) A medicament comprising the antibody according to (43) or (44).
(65) A medicament comprising the antigen according to (46).
(66) A medicament comprising the cell according to (52) or (55).
(67) The medicament according to any one of (60) to (66), which is a medicament for diagnosing, preventing and/or treating diseases caused by the disorder of an ectoderm-derived cell.
(68) The medicament according to (67), wherein the diseases caused by the disorder of an ectoderm-derived cell are diseases caused by the disorder of a nervous system cell or an epidermal system cell.
(69) The medicament according to (68),
wherein the diseases caused by the disorder of a nervous system cell are Alzheimer disease, Huntington chorea, Parkinson disease, ischemic cerebral disease, epilepsy, brain injury, vertebral injury, motor neuron disease, neurodegeneration disease, pigmentary retinal dystrophy, cochlear hearing loss, multiple sclerosis, amyotrophic lateral sclerosis or diseases due to a neurotoxin damage; and
the diseases caused by the disorder of an epidermal system cell are burn, wound, healing of wound, compression gangrene or psoriasis.
(70) A method for immunologically detecting the antigen according to (46), which comprises using the antibody according to (43) or (44).
(71) A tissue immunostaining method of the antigen according to (46), which comprises using the antibody according to (43) or (44).

DETAILED DESCRIPTION OF THE INVENTION

Figure 1:
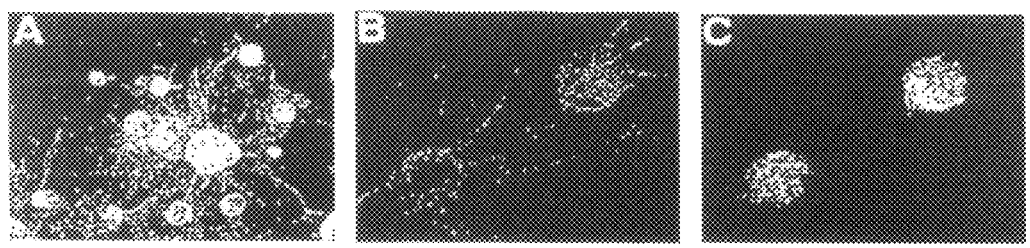
FIG. 1 is a microphotograph showing a result in which colonies formed by coculturing ES cell EB5 with PA6 cell are stained with antibodies against (A) NCAM, (B) tubulin and (C) nestin.

This application is based on Japanese application Nos. 2000-144059 filed on May 16, 2000 and 2000-290819 filed on Sep. 25, 2000, and U.S. provisional application No. 60/257,049 filed on Dec. 20, 2000, the entire contents of which are incorporated hereinto by reference.

The embodiments and methods for carrying out the present invention are described below in detail.

1. Method for Inducing Differentiation of the Present Invention (1) Animals to be Applied Examples of the animals used in the present invention include vertebral animals, particularly warm-blooded animals, and more particularly mammals such as mouse, rat, guinea pig, hamster, rabbit, cat, dog, sheep, pig, cattle, goat, monkey, human and the like.

(2) Embryonic Stem Cell

The embryonic stem cell include those cells which can be cultured in vitro and have a pluripotency capable of differentiating into all cells constituting the living body. Examples include (a) an embryonic stem cell of, e.g., a mammal established by culturing an early embryo before implantation, and specific examples include an ES cell established from an early embryo-constituting inner cell mass, an EG cell established from a primordial germ cell, a cell isolated from a cell group (e.g., primitive ectoderm) having a pluripotency of an early embryo before implantation and a cell obtained by culturing such a cell. Since it is known that an EC cell established from a malignant teratoma shows properties similar to those of the ES cell, it is included in the embryonic stem cell of, e.g., a mammal established by culturing an early embryo before implantation in a broad sense.

The embryonic stem cell according to the present invention includes the embryonic stem cell of (a), (b) an embryonic stem cell established by culturing an early embryo produced by nuclear transplantation of the nucleus of a somatic cell and (c) an embryonic stem cell in which a gene on the chromosome of the embryonic stem cell of (a) or (b) is modified using a gene engineering technique.

(3) Ectodermal Cell and Ectoderm-Derived Cell

The embryonic stem cell described above can be differentiation-induced into an ectodermal cell or an ectoderm-derived cell by culturing the embryonic stem cell under non-aggregation conditions using the method for inducing differentiation of the present invention.

According to the present invention, the ectodermal cell include germ layer cells comprising a cell having a pluripotency capable of differentiating into a nervous system cell or an epidermal system cell. Examples include a fetal ectodermal cell differentiated from a primitive ectoderm.

According to the present invention, the ectoderm-derived cell includes functional cells which are differentiated from an ectodermal cell and constitute the living body. Specific examples include nervous system cells and epidermal system cells. That is, an ectodermal cell can be induced into a nervous system cell or an epidermal system cell.

(a) Nervous System Cell

Examples of the nervous system cell include a neural stem cell, a nerve cell, a cell of neural tube, a cell of neural crest and the like.

(i) Nerve Cell

The nerve cell means a cell which functions to receive a stimulus from other nerve cells or stimulus receptor cells and transmit the stimulus to other nerve cells, muscle or glandular cells.

The nerve cell is classified based on the difference in the neurotransmitter produced by the nerve cell, specifically, based on, e.g., each neurotransmitter and synthase of the neurotransmitter. The neurotransmitter includes both of peptide and non-pepeide substances. The non-peptide neurotransmitter includes dopamine, noradrenaline, adrenaline, serotonin, acetylcholine, γ-aminobutyric acid and glutamic acid. Dopamine, noradrenaline and adrenaline are called catecholamine.

Examples of nerve cells classified by these neurotransmitters include dopaminergic neurons, acetylcholinergic neurons, γ-aminobutyratergic neurons, serotonergic neurons, noradrenalinergic neurons, adrenalinergic neurons, glutamatergic neurons and the like. The dopaminergic neurons, noradrenalinergic neurons and adrenalinergic neurons are generally referred to as catecholaminergic neurons.

The catecholaminergic neurons express tyrosine hydroxylase in common, and the noradrenalinergic neurons and the adrenalinergic neurons express dopamine-β-hydroxylase in common. Also, phenylethanolamine N-methyltransferase is specifically expressed in the noradrenalinergic neurons, tryptophan hydroxylase is specifically expressed in the serotonergic neurons, choline acetyltransferase is specifically expressed in the acetylcholinergic neurons and glutamate decarboxylase is specifically expressed in the γ-aminobutyratergic neurons. Accordingly, a method for recognizing a nerve cell includes an identification method using antibodies which recognizes enzymes, a method for detecting expression of mRNA coding for the enzyme, and the like.

Examples of the peptide neurotransmitter include adrenocorticotropic hormone (corticotropin (ACTH)), ααγ, β-lipotropin, α-melanin cell stimulating hormone (MSH), α-endorphin, β-endorphin, γ-endorphin, methionine enkephalin (Met-enkephalin), leucine enkephalin (Leu-enkephalin), α-neoendorphin, β-neoendorphin, dynorphin A, dynorphin B, leumorphin, vasopressin, neurophysin, oxytocin, neurophysin I, substance P, neurokinin A, neuropeptide K, neuropeptide-γ, neurokinin B, bombesin, gastrin-releasing peptide, secretin, motilin, glucagon, vasoactive intestinal peptide, growth hormone-releasing factor, insulin, insulin-like growth factors, somatostatin, gastrin, cholecystokinin, neuropeptide Y, pancreatic polypeptide, peptide YY, corticotropin-releasing factor, calcitonin, calcitonin gene-related peptide, angiotensin, bradykinin, thyrotropin-releasing hormone, neurotensin, galanin and luteinizing hormone-releasing hormone. Nerve cells capable of producing these peptide neurotransmitters can be identified by staining using an antibody which recognizes a neurotransmitte or a neurotransmitter precursor peptide, or by detecting expression of mRNA coding for the neurotransmitter or neurotransmitter precursor peptide.

Also, the motor neuron transmits information to skeletal muscle by secreting acetylcholine from its nerve ending and is classified into the acetylcholinergic neurons. Examples of a marker protein of the motor nerve cell include islet 1 (O. Karlson et al., *Nature,* 344, 879, 1990).

The method for inducing differentiation of the present invention is suitably used for inducing differentiation into nerve cells, preferably dopaminergic neurons, acetylcholinergic neurons, γ-aminobutyratergic neurons and serotonergic neurons.

Particularly, the dopaminergic neuron induced from an embryonic stem cell by the method of the present invention is characterized as a cell which expresses tyrosine hydroxylase whose expression is observed in the catecholaminergic neurons in common but which does not express dopamine-β-hydroxylase whose expression is observed in the noradrenalinergic neurons and adrenalinergic neurons in common, as described above, and is capable of improving symptoms of nerve degeneration diseases such as Parkinson disease by its transplantation.

(ii) Neural Stem Cell

The neural stem cell is defined as a cell which is capable of differentiating into neuron, astrocyte and oligodendrocyte and also has the self-replicating ability. The neural stem cell does not have the pluripotency of embryonic stem cell to differentiate into all cells but functions to supply a nerve cell, an astrocyte and an oligodendrocyte in the brain.

Accordingly, examples of a method for confirming that the cell is the neural stem cell include a method in which the cell is practically transplanted into the brain and its differentiation ability is confirmed and a method in which differentiation induction of the neural stem cell into a nerve cell, an astrocyte and an oligodendrocyte is confirmed in vitro (*Mol. Cell. Neuro Science,* 8, 389 (1997); *Science,* 283, 534 (1999)).

Also, the neural stem cell having such a function can be stained with an anti-nestin antibody which recognizes a cytoskeletal protein nestin whose expression in a nerve precursor cell has been confirmed (R. Mckay, *Science,* 276, 66 (1997)). Accordingly, the neural stem cell can also be confirmed by staining it with the anti-nestin antibody.

(iii) Cells of Neural Tube and Neural Crest

In the initial stage development in chordates, a primitive streak appears in the primitive ectoderm layer and neural induction starts. The neural induction means a stage in which an ectoderm positioned on the dorsal side of an early embryo receives a signal from an organizer region positioned in its adjacent or inner part and thereby differentiates into a neuroectoderm. The neuroectoderm formed by this neural induction becomes a neural plate independently from a non-neuroectoderm, namely an epidermal ectoderm, and then forms a neural tube by invaginating into the ventral side. The ectoderm portion positioned between the neural plate and epidermal ectoderm forms a neural crest during the invagination. All cell groups of the central nervous system are generated from one layer of the neuroepithelial tissues which constitute the neural tube. That is, the front part of the neural tube expands and forms a brain vesicle which becomes primordium of the brain, and the rear part differentiates into the spinal cord as the tube. The neural crest does not directly take part in the differentiation of central nerve itself, but the cells constituting neural crest migrate and differentiate into various tissues such as cerebral or spinal ganglion, sympathetic nerve and its ganglion, adrenal medulla and melanocyte.

The term "cell of neural tube" means a cell which constitutes a neural tube in the above generation process.

The term "cell of neural crest" means a cell which constitutes a neural crest in the above generation process.

The method for inducing differentiation of the present invention is suitably used for the differentiation induction into the cells of neural tube and neural crest.

The cell of neural tube induced from an embryonic stem cell by the method of the present invention includes a cell characterized as a cell of neural tube before the step in which the dorso-ventral axis is determined, which is capable of differentiating into a cell positioned at the ventral side by reacting with sonic hedgehog (hereinafter referred to as "shh") as a ventral factor of neural tube and of differentiating into a cell positioned at the dorsal side by reacting with bone morphogenetic protein 4 (hereinafter referred to as "BMP4") as a dorsal factor of neural tube. Also, a cell of the neural tube ventral side, expressing a marker HNF-3β (hepatocyte nuclear factor-3β, hereinafter referred to as "HNF-3β") positioned on the basal plate of the most ventral side of neural tube, a cell of the neural tube ventral side, expressing a marker Nkx2.2 existing secondary to the HNF-3β from the ventral side of neural tube, and a cell of the neural tube dorsal side, expressing Pax-7, all of which are differentiated from the above cell, are also included as neural tube cells induced from an embryonic stem cell by the method of the present invention.

The cell of neural crest induced from an embryonic stem cell by the method of the present invention includes a cell which is characterized as a cell expressing AP-2 (activator protein 2, hereinafter referred to as "AP-2").

Shh is a secretory factor relating to the morphogenesis in the early stage of development, such as formation of the dorso-ventral axis of neural tube and formation of the antero-posterior axis of limb bud (C. Chiang et al., *Nature,* 383, 407 (1996); M. Bitgood et al., *Curr. Biol.,* 6, 298 (1996)).

BMP4 is a secretory factor relating to the morphogenesis in the early stage of development, which reacts as a dorsal factor such as formation of the dorso-ventral axis of neural tube and formation of the dorso-ventral axis of mesoderm (J. M. Graff et al., *Cell,* 79, 169 (1994); A. Suzuki et al., *Proc. Natl. Acad. Sci. USA,* 91, 10255 (1994)).

It is known that HNF-3β is expressed in the liver, small intestines, lungs and pancreas Langerhans' cell after birth and is also expressed at the developmental stage in the intestinal epithelium and liver primordium of in and after the fore-gut forming stage or, through the gastulation stage, in organizer regions such as dorsal lip part, pro-notochordal plate, notochord and ventral central part of neural tube, and it is known that this is an important factor in controlling a signal for the body axis pattern formation of neural tube and metamere at the time of development (C. Vaisse et al., *Diabetes,* 46, 1364 (1997); M. Levinson-Dushnik et al., *Mol. Cell. Biol.,* 17, 3817 (1997)).

It is known that Nkx2.2 is a factor which is expressed in the ventral side of neural tube at the developmental stage, and plays an important role in the differentiation and function of these cells (M. Price et al., *Neuron,* 8, 241 (1992)).

Pax-7 is a factor which is expressed solely in the dorsal part of neural tube (B. Jostes et al., *Mech. Dev.,* 33, 27 (1990) and plays an important role in the differentiation formation of head neural crest-derived tissue and central nervous system (A. Mansouri et al., *Development,* 122, 831 (1996)).

AP-2 is a factor which is expressed in neural crest cell and head perception ganglion, spinal ganglion and facial mesenchyme as important tissues derived from the neural crest cell, in the mouse-derived embryo of 8.5 to 12.5 days of fetal age, and plays an important role in the differentiation and function of these cells (H. Schorle et al., *Nature,* 381, 235 (1996); J. Zhang et al., *Nature,* 381, 238 (1996)). As transcription factors other than AP2, Pax-3 and twist can be exemplified, which are expressed in the neural crest cell and take part in the head capsule atresia.

Since marker genes for these cells of neural tube and neural crest and factors which exert influences on the developmental polarity of these cells are known, a cell can be specified by detecting mRNA of the marker gene, detecting the expressed marker gene product itself or examining a response to the factor.

(b) Epidermal System Cell

Examples of an epidermal system cell include an epidermal cell and the like.

The skin comprises an ectoderm-derived epithelial tissue epidermis and a mesoderm-derived connective tissue dermis, and the epidermal cell is defined as an epithelial cell which constitutes the epidermis. The epidermis basically comprises a keratinized stratified squamous epithelium comprising, from the dermis toward the outer surface, stratum basale, stratum spinosum, stratum granulosum, stratum lucidum and stratum corneum. The epidermal cell is classified using morphology of the cell and expression mode of keratin filament as indexes. Since keratins 8 and 18 are expressed at the early stage of development, they are used as a marker of an epithelial cell at the early fetal period (R. G. Oshima et al., *Dev. Bio.*, 99, 447 (1983)). Keratin 19 is used as a marker of an epithelial cell in a fetus (P. C. Stasiak & E. B. Lane, *Nucleic Acids Res.*, 15, 10058 (1987)). Keratins 5 and 14 are used as a marker of an epithelial cell which constitutes the stratum basale of epidermis (E. Fuchs & H. Green, *Cell*, 19, 1033 (1980)). The epidermal cell during keratinization is called keratinocyte, and expression of keratins 5 and 14 decreases as the keratinization progresses but expression of keratins 1 and 10 increases instead (E. Fuchs & H. Green, *Cell*, 19, 1033 (1980); C. Bagutti et al., *Dev. Biol.*, 179, 184 (1996)).

Epidermal system cells, particularly epidermal cells, can be identified by staining with an antibody against each of these keratins or an antibody against E cadherin which is a marker of non-neuroectodermal cells or by detecting mRNA for these keratin proteins.

Differentiation induction into the epidermal cell of the stratum basale having high cell division ability can be suitably carried out by the method of the present invention.

(4) Culturing of Embryonic Stem Cell Under Non-Aggregation Conditions

The method for inducing differentiation of the present invention includes a method which comprises a step for preparing embryonic stem cells in a single cell state and a step for culturing the embryonic stem cell under non-aggregation conditions in the presence of a stroma cell or a stroma cell-derived factor.

Also, examples of the stroma cell include a stroma cell which will be described later in section 4, and examples of the stroma cell-derived, factor include an antigen which will be described later in section 8, a factor obtained by a method which will be described later in section 5, a culture supernatant of the stroma cell and a fragment of the stroma cell and the like.

Culturing of an embryonic stem cell under non-aggregation conditions means that culturing is started under a single cell state effected by disengaging mutual adhesion of cells, followed by culturing continuously. The single cell state means a condition in which individual cells are separated without mutual adhesion of cells, e.g., with an enzyme digestion.

In culturing, the inoculated cells do not aggregate or form an embryoid body. In order to start culturing of an embryonic stem cell in a single cell state, followed by continuously culturing, the embryonic stem cells are inoculated at a cell density of lower than the cell density used for usual subculturing of embryonic stem cells and cultured. That is, the embryonic stem cell is treated, e.g., with an enzyme digestion, a cell suspension of single cell state is produced using a medium and then the cell suspension is cultured under such conditions that individual cells are present without mutual contact in the culturing system. Such culturing is fundamentally different from the idea of a conventional embryoid body-employed method for generating the differentiation induction by positively aggregating cells and thereby reproducing a pseudo-embryo state. In this case, the cell density of inoculating embryonic stem cell by which individual cells are present without mutual contact in the culturing system is preferably from several tens to several hundreds of cells/cm$^2$, more preferably from 30 to 300 cells/cm$^2$.

Examples of the method for obtaining single cell state embryonic stem cell include a known enzyme digestion method used in tissue cell culturing. Specifically, the embryonic stem cell is proliferated to a stage from several 10% to an almost confluent by exchanging the medium on the preceding day, the medium is removed from the culture dish and then the cells are washed with an aqueous phosphate-buffered saline solution (hereinafter referred to as "PBS") several times, preferably 2 to 3 times. After washing, an appropriate enzyme digestion solution (e.g., PBS containing 1 mM EDTA and 0.25% trypsin) is added to the culture dish containing the embryonic stem cells, followed by culturing at 37° C. for several tens of minutes, preferably from 5 to 20 minutes. After the enzyme reaction, the cells are suspended in a medium produced in the following section 2 and centrifuged (e.g., at 4° C. and 200×g for 5 minutes) and then the embryonic stem cells are again suspended in the medium to thereby recover the embryonic stem cells in the single cell state.

Examples of the method for culturing an embryonic stem cell include the embryonic stem cell culturing methods described in *Manipulating the Mouse Embryo, A Laboratory Manual; Methods in Enzymology*, volume 225, Guide to Techniques in Mouse Development, Academic Press (1993); *Production of Mutation Mice Using ES Cell*; and the like. Also, it is possible to carry out serum-free culturing; e.g., the cell can be subcultured while keeping its characters as an undifferentiated embryonic stem cell using a Dulbecco's MEM medium supplemented with 15 to 20% KNOCKOUTS SR (manufactured by GIBCO BRL), 2 mM glutamine, 100 µM MEM non-essential amino acids solution, 50 U/ml penicillin, 50 U/ml streptomycin, 100 µM 2-mercaptoethanol and 1,000 U/ml LIF (M. D. Goldsborough et al., *Focus*, 20, 8 (1998)).

As the culturing method of the present invention for effecting differentiation induction of an ectodermal cell and an ectoderm-derived cell from an embryonic stem cell, any method can be used, so long as it is suitable for the differentiation induction of the embryonic stem cell to be used. Examples include a monolayer culturing method, a coculturing method with a supporting cell, a high density-maintaining culturing method, a micro-carrier culturing method, a perfusion culturing method, a soft-agar culturing method and the like. Specific examples include a method in which a single cell state embryonic stem cell is cultured in a medium produced in the following section 2, a method in which a single cell state embryonic stem cell suspended in a medium produced in the following section 2 is cocultured with a stroma cell produced in advance in the following section 4, for several days under non-aggregation conditions and the like.

The step of the present invention for culturing an embryonic stem cell under non-aggregation conditions is preferably carried out under serum-free culture conditions, but it is possible to carry out, after serum-free culturing, a step for culturing under serum-added culturing conditions (e.g., a step in which culturing is carried out at 37° C. in a stream of several percents, preferably 5%, of carbon dioxide in a $CO_2$ incubator, using a medium produced by adding preferably of several ten percents, more preferably from 5 to 20%, of a mammal serum to the basal medium described in the following section 2). Particularly, in differentiation induction in an epidermal system cell, the differentiation induction ratio can be further improved by including this step for culturing, under serum-added culturing conditions.

By this method, the ectodermal cell or ectoderm-derived cell of the present invention can be obtained. By the method of the present invention, the embryonic stem cell is differentiation-induced into the ectodermal cell or ectoderm-derived cell, and 5% or more, preferably 15% or more, more preferably 40% or more, and most preferably 80% or more, of the embryonic stem cell subjected to the method for inducing differentiation of the present invention can be differentiation-induced into an ectodermal system cell (an ectodermal cell or ectoderm-derived cell).

Differentiation of an ectodermal cell or an ectoderm-derived cell into a nervous system cell can be induced by continuing culturing by a method including the above step while optionally exchanging the medium.

In order to induce differentiation of an ectodermal cell or an ectoderm-derived cell into an epidermal system cell, it is preferable to add BMP4 to a culturing system including the above step.

In order to induce differentiation of an ectodermal cell or an ectoderm-derived cell into a cell of neural tube or neural crest, the above step using a medium which does not contain BMP4 is carried out and then, when differentiation of the embryonic stem cell into a neuroectoderm is started (e.g., 1 to 14 days, preferably 2 to 8 days, and more preferably 4 to 6 days after starting of culturing), culturing using a medium containing shh or BMP4 is continuously carried out along with optional exchange of the medium.

(5) Culturing in the Presence of Stroma Cell

In the method for inducing differentiation of the present invention, it is preferable to culture the embryonic stem cell in the presence of a stroma cell or a stroma cell-derived factor.

The stroma cell is described later in section 4, and examples of the stroma cell-derived factor include an antigen described later in section 8, a factor obtained by a method described later in section 5, a culture supernatant of the stroma cell, a fragment of the stroma cell and the like.

In the method for inducing differentiation of the present invention, the ratio of stroma cell to embryonic stem cell in the culturing system may be any ratio, so long as the embryonic stem cell can be differentiation-induced into an ectodermal cell or an ectoderm-derived cell by the ratio. But it is from $10^4$ to 1 per 1 (the number of stroma cells per the number of embryonic stem cells), preferably from $10^3$ to 1 per 1, and more preferably from $10^2$ to 10 per 1.

In this case, coculturing of an embryonic stem cell with a stroma cell includes coculturing in which the embryonic stem cell and stroma cell are physically contacted with each other and coculturing in which both cells are present in the same culturing system but cannot be contacted physically with each other due to their separation by a partition wall through which substances can pass.

Coculturing in which the embryonic stem cell and stroma cell are present in the same culturing system but cannot be contacted physically with each other due to their separation by a partition wall through which substances can pass includes coculturing in which both cells are separately cultured using a filter generally used in cell culture can be exemplified. The filter may have a pore size of preferably from 0.01 to several tens μm, more preferably from 0.02 to 12 μm. Specific examples of the filter include Membrane Culture Insert (manufactured by Iwaki Glass), Nunc TC Insert (manufactured by Nunc), COCULTURE Dish (manufactured by Greiner), Cell, Culture Insert (manufactured by Falcon), Chemotaxis Chamber (manufactured by Neuro Probe Inc.) and the like. Either of the embryonic stem cell and the stroma cell can be cultured on the filter, but it is preferable to culture the stroma cell on the filter.

Specific examples of the method for effecting differentiation induction of an ectodermal cell and a nervous system cell from an embryonic cell by coculturing the embryonic cell and stroma cell include a method in which the recovered embryonic stem cell is suspended in a medium produced in the following section 2 (e.g., a medium produced by adding 10% KNOCKOUT™ SR (manufactured by GIBCO BRL), 2 mM glutamine, 50 U/ml penicillin, 50 U/ml streptomycin, 100 μM MEM non-essential amino acids solution, 1 mM pyruvic acid and 100 μM 2-mercaptoethanol to the Glasgow MEM medium), the suspension is inoculated at a cell density of several tens to several hundreds of cells/cm², preferably 100 cells/cm², into a culture vessel (e.g., a cell culture flask) in which the stroma cell produced in the following section 4 is cultured, and then the cells are cultured at 37° C. for 5 to 20 days, preferably 7 to 10 days, in a stream of several percent, preferably 5%, of carbon dioxide in a $CO_2$ incubator.

Specific examples of the method for effecting differentiation induction of an ectodermal cell and an epidermal system cell from an embryonic cell by coculturing the embryonic cell and stroma cell include a method in which the recovered embryonic stem cell is suspended in a medium produced in the following section 2 (e.g., a medium produced by adding 10% KNOCKOUT™ SR (manufactured by GIBCO BRL), 2 mM glutamine, 50 U/ml penicillin, 50 U/ml streptomycin, 100 μM MEM non-essential amino acids solution, 1 mM pyruvic acid, 100 μM 2-mercaptoethanol and 0.1 to 100 ng/ml, preferably 1 to 50 ng/ml, BMP4 to the Glasgow MEM medium), the suspension is inoculated at a cell density of from several tens to several hundreds of cells/cm², preferably 100 cells/cm², into a culture vessel (e.g., a cell culture flask) in which the stroma cell produced in the following section 4 is cultured, and then the cells are cultured at 37° C. for 5 to 20 days, preferably 7 to 10 days, in a stream of several percent, preferably 5%, of carbon dioxide in a $CO_2$ incubator.

In addition, instead of coculturing the embryonic stem cell with stroma cell, the ectodermal cell and ectoderm-derived cell can also be differentiation-induced from the embryonic cell by using a medium produced by adding a culture supernatant of OP9 cell (T. Nakano et al., *Science*, 272, 722 (1996)), NIH/3T3 cell (J. L. Jainchill et al., *J. Virol.*, 4, 549 (1969)) or MC3T3-G2/PA6 cell to the embryonic stem cell culturing medium. Furthermore, instead of coculturing the embryonic stem cell with stroma cell, the ectodermal cell and ectoderm-derived cell can also be differentiation-induced from the embryonic cell by using a medium produced by adding a factor produced by OP9 cell, NIH/3T3 cell, MC3T3-G2/PA6 cell (H. Komada et al., *J. Cell. Physiol.*, 112, 89 (1982)), STO cell (G. Martin, *Proc. Natl. Acad. Sci. USA*, 78, 7634 (1981); M. J. Evans et al., *Nature*, 292, 154 (1981)) or fetal primary culture fibroblast (*Manipulating the Mouse Embryo, A Laboratory Manual, Gene Targeting; Production of Mutation Mice Using ES Cell*) to the medium.

(6) Culturing without Using Retinoic Acid

According to the method for inducing differentiation of the present invention, it is preferred to culture the embryonic stem cell without using retinoic acid in the culturing step of the cell under non-aggregation conditions.

The term "culturing without using retinoic acid" means that the cell is cultured without using retinoic acid at a non-physiological concentration. The non-physiological concentration means a concentration higher than the in vivo physiological concentration. Specifically, since it is known that retinoic acid is present in human blood generally at a concentration of about $10^{-8}$ mol/l (Seikagaku Jiten; second edition, Tokyo Kagaku Dojin (1992)), a concentration range of from $10^{-7}$ to $10^{-6}$ mol/l is the non-physiological concentration. Since retinoic acid has an action as a morphogen which has influence upon the morphogenesis at the time of developmental differentiation and, depending on the cell species, also has strong toxicity, there is a possibility of causing secondary side effects when a culture system using retinoic acid at a non-physiological concentration is applied to a medical treatment.

Thus, since the risk accompanied by the use of retinoic acid can be avoided, culturing without using retinoic acid is useful.

(7) Culturing in which Differentiation of Mesodermal System Cell is not Substantially Induced According to the method for inducing differentiation of the present invention, it is preferred that differentiation of a mesodermal system cell is not substantially induced in the culturing system.

The term "differentiation of a mesodermal system cell is not substantially induced" as used herein means that the ratio of a mesodermal system cell differentiated in the culturing system is 5% or less, preferably 2% or less, based on the total number of cells in the culturing system.

In this case, the mesodermal system cell means a cell comprising organs and tissues such as muscular system, connecting tissue, skeletal system, circulatory organ system, urinary organ system, reproductive system and the like.

The mesodermal system cell can be identified using, e.g., a method in which it is detected using an antibody which specifically recognizes the mesodermal system cell, a method in which mRNA for a protein specifically expressed in the mesodermal system cell is detected or a method in which it is detected using an antibody which specifically recognizes the protein.

(8) Culture Vessel

As the culture vessel used in the present invention, any culture vessel which can culture the embryonic stem cell can be used, but a culture vessel for cell culturing is preferred. Examples of the culture vessel for cell culturing include a flask, a tissue culture flask, a dish, a Petri dish, a tissue culture dish, a Conzar dish, a Permanox dish, a multi-dish, a microplate, a micro-well plate, a multi-plate, a multi-well plate, a separate strip well, a Terasaki plate, a tissue culture chamber slide, a schale, a cell culture schale, a tissue culture tube, a tray, a cell culture tray, a cell factory, a culture bag, a techno pot, a roller bottle, a spinner, a hollow fiber and the like. In order to control adhesiveness of the culture vessel and cells, the cell-contacting side surface of the culture vessel can be artificially treated. Examples of the artificial treatment of the culture vessel surface include collagen coating, gelatin coating, poly-L-lysine coating, fibronectin coating, laminin coating, proteoglycan coating, glycoprotein coating, matrigel coating, silicon coating and the like. In addition, the vessel can also be treated to provide a negative electric charge such as Primaria (manufactured by Falcon).

2. Production of Medium

With regard to the medium of the present invention used in the method for differentiation-inducing an ectodermal cell and ectoderm-derived cell from an embryonic stem cell, a medium usually used in culturing of animal cells can be prepared as a basal medium.

As the basal medium, any medium available the culturing of animal cells can be used. Examples include BME medium (*Proc. Soc. Exp. Biol. Med.*, 89, 363 (1965)), BGJb medium (*Exp. Cell Res.*, 25, 41 (1961)), CMRL 1066 medium (*N.Y. Academy of Science*, 5, 303 (1957)), Glasgow MEM medium (*Virology*, 16, 147 (1962)), Improved MEM Zinc Option medium (*J. National Cancer Inst.*, 49, 1705 (1972)), IMDM medium (*In Vitro*, 9, 6 (1970)), Medium 199 medium (*Proc. Soc. Exp. Biol. Med.*, 73, 1 (1950)), Eagle's MEM medium (*Science*, 130, 432 (1959)), Alpha MEM medium (*Nature New Biology*, 230, 310 (1971)), Dulbecco's MEM medium (*Virology*, 8, 396 (1959)), Ham's medium (*Exp. Cell Res.*, 29, 515 (1963); *Proc. Natl. Acad. Sci. USA*, 53, 288 (1965)), RPMI 1640 medium (*J. A. M. A.*, 199, 519 (1967)), Fischer's medium (*Methods in Med. Res.*, 10 (1964)), McCoy's medium (*Proc. Soc. Exp. Biol. Med.*, 100, 115 (1959)), William's E medium (*Exp. Cell Res.*, 69, 106 (1971); *Exp. Cell Res.*, 89, 139 (1974)), a mixed medium thereof and the like.

Also, any of the embryo culturing media described, e.g., in *Manipulating the Mouse Embryo, A Laboratory Manual* and *Methods in Enzymology*, volume 225, Guide to Techniques in Mouse Development, Academic Press (1993); *Production of Mutation Mice Using ES Cell*, such as M2 medium, M16 medium, Whitten medium and in vitro fertilization medium, can be used as a basal medium, so long as it can be used in embryo culturing.

Moreover, any one of media produced by adding various growth factors as serum substitutes, or a factor produced, e.g., by a stroma cell, to these basal medium, or a protein-free medium capable of culturing animal cells and embryo can also be used as the medium of the present invention. Specific examples include a serum-free medium to which commercially available KNOCKOUT™ SR is added (M. D. Goldsborough et. al., *Focus*, 20, 8 (1998)), a serum-free medium to which insulin and transferrin are added (e.g., CHO-S-SFM II (manufactured by GIBCO BRL), Hybridoma-SFM (manufactured by GIBCO BRL), eRDF Dry Powdered Media (manufactured by GIBCO BRL), UltraCULTURE™ (manufactured by BioWhittaker), UltraDOMA™ (manufactured by BioWhittaker), UltraCHO™ (manufactured by BioWhittaker), UltraMDCK™ (manufactured by BioWhittaker), ITPSG medium (S. Hosoi et al., *Cytotechnology*, 5, S17 (1991)), ITSFn medium (A. Rizzino and C. Growley, *Proc. Natl. Acad. Sci. USA*, 77, 457 (1980)) or mN3 medium (S. Okabe et al., *Mech. Dev.*, 59, 89 (1996)), a medium to which a cell-derived factor is added (e.g., a medium to which a culture supernatant of a pluripotency teratocarcinoma cell PSA1 is added (G. R. Martin, *Proc. Natl. Acad. Sci. USA*, 78, 7634 (1981)), a medium which contains a culture filtrate of the stroma cell described in the following section 4, a medium which contains a factor produced by the stroma cell described in the following section 5, a medium which contains an antigen component obtained in the following section 8, a medium which contains BMP4 and a protein-free medium (e.g., CD-CHO (manufactured by GIBCO BRL) PFHM-II (manufactured by GIBCO BRL) or UltraDOMA-PF™ (manufactured by BioWhittaker)).

3. Production of Embryonic Stem Cell

Production methods of the embryonic stem cells (a), (b) and (c) described in 1-(2) are specifically described.

(1) Production of Embryonic Stem Cell Established by Culturing Early Stage Embryo Before Implantation An embryonic stem cell can be produced from an early stage embryo before implantation by culturing the early stage embryo according to the method described in a reference (*Manipulating the Mouse Embryo, A Laboratory Manual*).

(2) Production of Embryonic Stem Cell Nuclear-Transplanted with the Nucleus of Somatic Cell An egg transplanted with the nucleus of a somatic cell of a mammal cell and started normal development can be produced in the following manner using a method reported by, e.g., Wilmut et al. (*Nature*, 385, 810 (1997)), Cibelli et al. (*Science*, 280, 1256 (1998)), A. Iritani et al. (*Protein, Nucleic Acid and Enzyme*, 44, 892 (1999)), Baguisi et al. (*Nature Biotechnology*, 17, 456 (1999)), Wakayama et al. (*Nature*, 394, 369 (1998); *Nature Genetics*, 22, 127 (1999); *Proc. Natl. Acad. Sci. USA*, 96, 14984 (1999)) or Rideout III et al (*Nature Genetics*, 24, 109 (2000)).

An egg which acquired the nucleus of other somatic cell and started normal development can be obtained by starting its development using a method in which the nucleus of a mammal cell is excised, initialized (an operation to return the nucleus to such a state that it can repeat the development again) and injected into an enucleated unfertilized egg of a mammal, and then incubating the development-started egg.

As the method for initializing the nucleus of a somatic cell, several methods are known. For example, the following methods are known.

The initialization can be carried out by changing the medium for culturing a nuclear donor side cell from a medium containing from 5 to 30%, preferably 10%, of fetal calf serum (e.g., M2 medium) to a poor nutrient medium containing from 0 to 1%, preferably 0.5%, of fetal calf serum and culturing the cell for a period of from 3 to 10 days, preferably 5 days, thereby to induce the cell cycle into an interphase state (G0 phase or G1 phase). This method is suitable, for example, when the mammal is sheep, goat or cattle.

Also, the initialization can be carried out by injecting the nucleus of a nucleus donor side cell into an enucleated unfertilized egg of a mammal of the same species and incubating the egg for several hours, preferably from about 1 to 6 hours. This method is suitable, for example, when the mammal is a mouse.

The thus initialized nucleus becomes possible to start its development in an enucleated unfertilized egg. Several methods are known as the method for starting development of the initialized nucleus in an enucleated unfertilized egg. The development can be started by transplanting a nucleus initialized by inducing the cell cycle into an interphase state (G0 phase or G1 phase) into an enucleated unfertilized egg of a mammal of the same species, e.g., by electrofusion to thereby activate the egg. This method is suitable, for example, when the mammal is sheep, goat or cattle.

Development of the nucleus initialized by injecting it into an enucleated unfertilized egg of a mammal of the same species can be carried out by again transplanting it into an enucleated unfertilized egg of a mammal of the same species, for example, using a method which uses a micromanipulator, stimulating it with an egg activating factor (e.g., strontium) and then treating it with a cell division inhibitor (e.g., cytochalasin B) to inhibit release of a secondary polar body. This method is suitable, for example, when the mammal is a mouse.

Once an egg which started the development is obtained, the embryonic stem cell can be obtained by a known method described in, for example, *Manipulating the Mouse Embryo, A Laboratory Manual; Gene Targeting; Production of Mutation Mice Using ES Cell* and the like.

(3) Production of Embryonic Stem Cell in which Gene on its Chromosome is Modified An embryonic stem cell in which a gene on its chromosome is modified can be produced by using homologous recombination techniques.

Examples of the chromosomal gene to be modified include genes for histocompatibility antigens and genes related to diseases caused by disorders of nervous system cells or epidermal system cells.

Modification of the target gene on the chromosome can be carried out using a method described in, for example, *Manipulating the Mouse Embryo, A Laboratory Manual; Gene Targeting; Production of Mutation Mice Using ES Cell* and the like.

Specifically, a genomic gene of the target gene to be modified (e.g., a histocompatibility antigen gene or a disease-related gene) is isolated, and a target vector for homologous recombination of the target gene is produced using the isolated genomic gene. An embryonic stem cell having a modified chromosomal gene can be produced by introducing the thus produced target vector into embryonic stem cells and selecting a cell in which homologous recombination occurred between the target gene and the target vector.

Examples of the method for isolating genomic gene of the target gene include a known method described in *Molecular Cloning, A Laboratory Manual*, Second Edition, Cold Spring Harbor Laboratory Press (1989) (hereinafter referred to as "*Molecular Cloning*, Second Edition") or in *Current Protocols in Molecular Biology*, John Wiley & Sons (1987-1997) (hereinafter referred to as "*Current Protocols in Molecular Biology*") and the like. The genomic gene of the target gene can also be isolated, for example, using Genome DNA Library Screening System (manufactured by Genome Systems) or Universal GenomeWalker™ Kits (manufactured by CLONTECH).

The target vector for carrying out homologous recombination of the target gene can be produced by using the method described in, for example, *Gene Targeting; Production of Mutation Mice Using ES Cell* and the like. As the target vector, any one of its replacement type and insertion type can be used.

Examples of a method for efficiently selecting a homologous recombinant include a method such as the positive selection, promoter selection, negative selection or poly(A) selection described in, for example, *Gene Targeting; Production of Mutation Mice Using ES Cell* and the like.

Examples of the method for the selection of the homologous recombinant of interest from the selected cell lines include the Southern hybridization for genomic DNA (*Molecular Cloning*, Second Edition), PCR (*PCR Protocols*, Academic Press (1990)) and the like.

4. Production of Stroma Cell

Regarding the stroma cell used in the method for inducing differentiation of an embryonic stem cell into an ectodermal cell or an ectoderm-derived cell in the present invention, any of the cells having activity of inducing differentiation of an embryonic stem cell into an ectodermal cell or an ectoderm-derived cell can be used. A stroma cell which is recognized by an antibody of the present invention produced by a method that will be described later in 7, preferably the monoclonal antibody produced by a hybridoma FERM BP-7573 obtained in Example 15 (5), is suitably used. Specific examples include:

(a) a fetal primary culture fibroblast (*Manipulating the Mouse Embryo, A Laboratory Manual; Gene Targeting; Production of Mutation Mice Using ES Cell*);

(b) an SIHM mouse-derived STO cell (G. Martin, *Proc. Natl. Acad. Sci. USA*, 78, 7634 (1981); M. J. Evans et al., *Nature*, 292, 154 (1981));

(c) a mouse fetus-derived NIH/3T3 cell (J. L. Jainchill et al., *J. Virol.*, 4, 549 (1969));

(d) an M-CSF deficient mouse calvaria-derived OP9 cell (T. Nakano et al., *Science*, 272, 722 (1996));

(e) a mouse calvaria-derived MC3T3-G2/PA6 cell (H. Kodama et al., *J. Cell. Physiol.*, 112, 89 (1982));

(f) a stroma cell obtained by its differentiation induction from an embryonic stem cell which is already confirmed to have a pluripotency (*Manipulating the Mouse Embryo, A Laboratory Manual*); and (g) a stroma cell obtained by its differentiation induction from a bone marrow-derived mesenchymal stem cell which is shown to have a differentiation potency into various stroma cells (*Science*, 284, 143 (1999)).

Among these, a stroma cell of (c), (d) or (e) is preferred, and a stroma cell of (e) is more preferred.

The stroma cell recognized by the monoclonal antibody produced by a hybridoma FERM BP-7573 obtained in Example 15 (5) is identified by immunological assay described in documents (e.g., *Monoclonal Antibodies: Principles and Applications*, Wiley-Liss, Inc., 1995; *Enzyme Immunoassay*, Third Edition, Igaku Shoin, 1987), for example, by an enzyme-antibody method using the antibody, a cell separation method using a flow cytometer or the like.

In culturing of the stroma cell, subculturing is preferably carried out using the method used for its establishment. Also, a method for culturing a feeder cell for use in culturing of a embryonic cell described, for example, in *Manipulating the Mouse Embryo, A Laboratory Manual; Methods in Enzymology*, volume 225, Guide to Techniques in Mouse Development, Academic Press (1993); *Production of Mutation Mice Using ES Cell* or the like. Specifically, it can be cultured using Dulbecco's MEM medium (manufactured by GIBCO BRL) supplemented with 10% fetal calf serum (manufactured by GIBCO BRL), 2 mM glutamine, 50 U/ml penicillin and 50 U/ml streptomycin.

When the stroma cell is used in culturing for inducing differentiation of an embryonic stem cell into an ectodermal cell or an ectoderm-derived cell, stroma cells proliferated on an appropriate support such as a culture dish may be used as living cells, or cells which lost the proliferation ability by undergoing a physicochemical treatment can be used. The cells which lost the proliferation ability by physicochemical treatment are cells from which the ability of forming next generation progenies accompanied by gene replication is completely lost, specifically, those cells which are obtained by culturing using an antitumor agent-containing medium, by a lethal dose radiation irradiation or by applying treatment for tissue fixation used in pathologic diagnosis.

The living stroma cells can be produced, for example, by washing the cells whose cell density reached almost confluent by exchanging the medium on the preceding day, several times with PBS, and then adding a medium of the present invention obtained in the above section 2 (e.g., a serum-free medium used in culturing for inducing differentiation of an embryonic stem cell into an ectodermal cell or an ectoderm-derived cell). Alternatively, they can also be produced by digesting the cells which reached an almost confluent with an appropriate digestive enzyme (e.g., PBS containing 0.02% EDTA and 0.05 to 0.25% trypsin or actinase), suspending the thus recovered cells in a medium of the present invention obtained in the above section 2 (e.g., a serum-free medium used in culturing for inducing differentiation of an embryonic stem cell into an ectodermal cell or an ectoderm-derived cell), and then inoculating the suspension into a culture vessel (e.g., a tissue culture dish coated with 0 to 1%, preferably 0.1%, of gelatin) and culturing for about 1 day.

The stroma cell which lost the proliferation ability by culturing using an antitumor agent-containing medium can be produced by a method described in, for example, *Manipulating the Mouse Embryo, A Laboratory Manual; Gene Targeting; Production of Mutation Mice Using ES Cell* or the like. For example, it can be produced by culturing the cells whose cell density reached an almost confluent by exchanging the medium on the preceding day, in a medium containing 1 to 100 µg/ml, preferably 10 µg/ml, of mitomycin C for several hours, preferably 2 to 3 hours, washing the resulting cells several times with PBS, digesting the cells with an appropriate digestive enzyme (e.g., PBS containing 0.02% EDTA and 0.05 to 0.25% trypsin or actinase), suspending the thus recovered cells in a medium of the present invention obtained in the above section 2 (e.g., a serum-free medium used in culturing for inducing differentiation of an embryonic stem cell into an ectodermal cell or an ectoderm-derived cell), and then inoculating the suspension into a culture vessel (e.g., a tissue culture dish coated with 0 to 1%, preferably 0.1%, of gelatin), followed by culturing for about 1 day. In addition, the stroma cell which lost the proliferation ability can also be produced by using other antitumor agent such as 5-fluorouracil, adriamycin, ara-C, methotrexate or the like at a concentration of $\frac{1}{10}$ to 10 times of, preferably identical to, the concentration used in the living body described in *The Pharmacopoeia of Japan*, instead of mitomycin C.

The stroma cell which lost the proliferation ability by receiving lethal dose of a radiation irradiation can be produced by using a method described in, for example, in *Tissue Culture Techniques*, Asakura Shoten (1982); *Tissue Culture Techniques* (Second Edition), Asakura Shoten (1988); *Tissue Culture Techniques* (Third Edition), Asakura Shoten (1996); or the like. For example, it can be produced by exposing the cells whose cell density reached almost confluent by exchanging the medium on the preceding day to 200 to 5,000 rad, preferably 500 to 1,000 rad, of an X-ray or γ-ray, washing the cells several times with PBS, and then adding a medium of the present invention obtained in the above section 2 (e.g., a serum-free medium to be used in the culturing for inducing differentiation of an embryonic stem cell into an ectodermal cell or an ectoderm-derived cell). Alternatively, it can also be produced by digesting the radiation-irradiated cells with an appropriate digestive enzyme (e.g., PBS containing 0.02% EDTA and 0.05 to 0.25% trypsin or actinase), suspending the thus recovered cells in a medium of the present invention obtained in the above section 2 (e.g., a serum-free medium used in culturing for inducing differentiation of an embryonic stem cell into an ectodermal cell or an ectoderm-derived cell), and then inoculating the suspension into a culture vessel (e.g., a tissue culture dish coated with 0 to 1%, preferably 0.1%, of gelatin), followed by culturing for about 1 day.

The stroma cell which lost the proliferation ability by a tissue fixation treatment used in pathologic diagnosis can be produced by using a method described in, for example, *Histochemistry and Cytochemistry*, Gakusai Kikaku (1987-1999), edited and published every year by Japanese Society of Histochemistry and Cytochemistry, *Basic Techniques for Transmission Electron Microscopy*, Acad. Press (1986), *Electron Microscopy Chart Manual*, Igaku Shuppan Center (1993) or the like. Specifically, it can be produced by carrying out a microwave fixation, a rapid freeze-substitution fixation, a glutaraldehyde fixation, a p-formaldehyde fixation, a formalin fixation, an acetone fixation, a Van fixation, a periodic acid fixation, a methanol fixation or an osmic acid fixation. For example, it can be produced by soaking the cells whose cell density reached almost confluent by exchanging the medium on the preceding day, in a solution containing 0.1 to 50%, preferably 1 to 10%, and more preferably from 3 to 5%, of p-formaldehyde at 4° C. for, e.g., several minutes to several hours, preferably 5 minutes to 1 hour, and more preferably 30 minutes, and then washing the cells several times with 5. Method for Obtaining Stroma Cell-Derived Factor Having Activity of Inducing Differentiation of Embryonic Stem Cell into Ectoderm-Derived Cell A factor having activity of inducing differentiation of an embryonic stem cell into an ectoderm-derived cell can be obtained from the stroma cell of the present invention. Specifically, it can be carried out using an expression cloning method described in, e.g., *Molecular Cloning*, Second Edition, *Current Protocols in Molecular Biology, Monoclonal Antibodies: principles and practice*, Third Edition, Acad. Press (1993) (hereinafter referred to as "*Monoclonal Antibodies*"), *Antibody Engineering, A Practical Approach*, IRL Press at Oxford University Press (1996) (hereinafter referred to as "*Antibody Engineering*"), or the like.

Specifically, for example, cDNA is produced from the stroma cell of the present invention and the cDNA is inserted into downstream of the promoter of an appropriate expression vector to prepare a recombinant vector and a cDNA library. Transformants which produce gene products produced by the stroma cell of the present invention are obtained by introducing the recombinant vector into a host cell suitable for the expression vector, and a transformant which produces a gene product having activity of inducing differentiation of an embryonic stem cell into an ectoderm-derived cell is selected therefrom. A factor having activity of inducing differentiation of an embryonic stem cell into an ectoderm-derived cell can be obtained by determining the gene sequence encoded by the cDNA introduced into the selected transformant.

This procedure is described in detail below.

As the host cell, a cell which does not have the activity of inducing differentiation of an embryonic stem cell into an ectoderm-derived cell is preferred. Specific examples include a Chinese hamster ovary-derived CHO cell (T. T. Puck et al., *J. Exp. Med.*, 108, 945 (1985)), a female cocker spaniel kidney-derived MDCK cell (C. R. Gaush et al., *Proc. Soc. Exp. Biol. Med.*, 122, 931 (1966); D. S. Misfeldt et al., *Proc. Natl. Acad. Sci. USA*, 73, 1212 (1976)), a rat fibroblast 3Y1 (S. Sandineyer et al., *Cancer Res.*, 41, 830 (1981)) and a green monkey kidney-derived COS cell (Y. Gluzman, *Cell*, 23, 175 (1981)). Among these, the COS cell which is suitable for expression cloning using an SV40 expression vector is preferred.

As the cell to be used in the production of cDNA, a stroma cell having activity of inducing differentiation of an embryonic stem cell into an ectoderm-derived cell is preferred. Specific examples include a fetal primary culture fibroblast (*Manipulating the Mouse Embryo, A Laboratory Manual; Production of Mutation Mice Using ES Cell*) and an SIHM mouse-derived STO cell (G. Martin, *Proc. Natl. Acad. Sci. USA*, 78, 7634 (1981)); M. J. Evans et al., *Nature*, 292, 154 (1981), more preferably a mouse fetus-derived NIH/3T3 cell (J. L. Jainchill et al., *J. Virol.*, 4, 549 (1969)), an M-CSF deficient mouse calvaria-derived OP9 cell (T. Nakano et al., *Science*, 272, 722 (1996)) and a mouse calvaria-derived MC3T3-G2/PA6 cell (H. Kodama et al., *J. Cell. Physiol.*, 112, 89 (1982)).

The method for preparing a cDNA library includes a method which will be described later in section 8. The thus produced cDNA library may be used as such, but, in order to concentrate the target gene, a cDNA library produced by carrying out a subtraction method (*Proc. Natl. Acad. Sci. USA*, 85, 5783 (1988)) using mRNA of a cell which does not have activity of inducing differentiation of an embryonic stem cell into an ectoderm-derived cell can also be used.

Examples of a method for introducing a recombinant vector, a method for obtaining a transformant and a method for culturing the thus obtained transformant using a medium include the methods described in the following section 8.

In the method for inducing differentiation of the present invention, a transformant which produces a gene product having activity of inducing differentiation of an embryonic stem cell into an ectoderm-derived cell can be selected by carrying out coculturing of the embryonic cell and the transformant.

Examples of a method for isolating cDNA introduced into the selected transformant and a method for determining gene sequence of the isolated cDNA include the methods described in the following section 8.

A stroma cell-derived factor having activity of inducing differentiation of an embryonic stem cell into an ectoderm-derived cell can also be obtained by a method other than the expression cloning method. Specifically, it can be purified using an effect to accelerate differentiation induction of an embryonic stem cell into an ectoderm-derived cell as an indication of the purification when the stroma cell of the present invention is used as the starting material and added to the medium. Examples of the purification method include the method described in the following section 8.

In addition, since the stroma cell-derived factor has a property of adsorbing a mucopolysaccharide (e.g., heparin), the factor can be obtained from the stroma cell-derived factor absorbed on a mucopolysaccharide, after allowing the factor in a culture system in which the stroma cell is cultured, or in a culture system in which an embryonic stem cell is cultured under non-aggregation conditions in the presence of the stroma cell, to absorb on the mucopolysaccharide. For example, the stroma cell-derived factor can be obtained by absorbing the factor to heparin using column chromatography with heparin as the carrier and then eluting the bound factor, using the differentiationinduced effect of the factor as the index.

6. Agent for Inducing Differentiation and Medicament Containing the Same (1) Agent for Inducing Differentiation The agent for inducing differentiation of the present invention can be of any form, so long as it contains the stroma cell or stroma cell-derived factor as the active ingredient. Examples include an agent comprising a culture capable of coculturing an embryonic stem cell with a stroma cell and an agent comprising the stroma cell. Cell fragments of the stroma cell and a culture supernatant of the stroma cell can also be used as the active ingredient of the agent for inducing differentiation.

Examples of the culture supernatant of the stroma cell include a culture supernatant obtained by culturing the stroma cell having activity of inducing differentiation of an embryonic stem cell into an ectodermal cell or an ectoderm-derived cell in a medium or a culture supernatant obtained by culturing the stroma cell in a medium containing a mucopolysaccharide.

In this case, any kind of mucopolysaccharide can be used, so long as it is capable of absorbing on factors which are produced by various stroma cells and are capable of inducing differentiation of an embryonic stem cell into an ectodermal cell or an ectoderm-derived cell, but, for example, heparin or the like is preferable. As the heparin, a commercially available known heparin can be used. The culture supernatant can be produced by culturing the stroma cell for 5 minutes to several days using a medium containing heparin within the range of several ng/ml to the several thousand ng/ml, preferably of several hundred ng/ml. The culture supernatant obtained in this manner can be effectively used in obtaining an agent for inducing differentiation of an embryonic stem cell into an ectodermal cell or an ectoderm-derived cell or an active factor which induces differentiation of an embryonic stem cell into an ectodermal cell or an ectoderm-derived cell.

Also, since a mucopolysaccharide such as heparin is considered to have a property of specifically interacting with an active factor which induces differentiation of an embryonic stem cell into an ectodermal cell or an ectoderm-derived cell, it can be used effectively in the evaluation method and screening method of substances related to the regulation in the differentiation of an embryonic stem cell into an ectodermal cell or an ectoderm-derived cell, or in the evaluation method and screening method of substances related to the regulation of functions of an ectodermal cell or an ectoderm-derived cell.

Preferably, the agent for inducing differentiation of an ectodermal cell into an epidermal system cell contains BMP4.

(2) Medicament Comprising the Agent for Inducing Differentiation

The agent for inducing differentiation of the present invention can be used as a therapeutic agent for diseases caused by the disorder of ectoderm-derived cells.

Examples of the disease cause by the disorder of ectoderm-derived cells include diseases caused by the disorder of nervous system cells or epidermal system cells.

Examples of the disease caused by the disorder of nervous system cells include Alzheimer disease, Huntington chorea, Parkinson disease, ischemic cerebral disease, epilepsy, brain injury, vertebral injury, motor neuron disease, neurodegeneration disease, pigmentary retinal dystrophy, cochlear hearing loss, multiple sclerosis, amyotrophic lateral sclerosis, a disease due to a neurotoxin damage and the like. Examples of the disease caused by the disorder of epidermal system cells include burn, wound, healing of wound, compression gangrene, psoriasis and the like.

The medicament comprising the agent for inducing differentiation of the present invention as the active ingredient can be administered by the active ingredient alone, but generally, it is preferable to provide the active ingredient as a pharmaceutical production produced by an optional method well known in the technical field of manufacturing pharmacy, by mixing it with one or more pharmaceutically acceptable carriers. Preferably, a sterile solution produced by dissolving it in an aqueous carrier such as water or an aqueous solution of sodium chloride, glycine, glucose, human albumin or the like is used. Also, pharmaceutically acceptable additives including a buffering agent and a tonicity agent for use in resembling the pharmaceutical production solution to physiological conditions, such as sodium acetate, sodium chloride, sodium lactate, potassium chloride, sodium citrate or the like, can be added. Also, it is possible to store the production by freeze-drying and use it by dissolving in an appropriate solvent when used.

It is preferable to use a route of administration which is most effective in carrying out a treatment. Examples include oral administration and parenteral administration such as buccal, airway, rectal, subcutaneous, intramuscular, intravenous administration and the like. Examples of the dosage form include sprays, capsules, tablets, granules, syrups, emulsions, suppositories, injections, ointments, tapes and the like.

Examples of the pharmaceutical production suitable for oral administration include emulsions, syrups, capsules, tablets, powders, granules and the like. For example, liquid productions such as emulsions, syrups and the like can be produced using, as additives, water, saccharides such as sucrose, sorbitol, fructose, etc.; glycols such as polyethylene glycol, propylene glycol, etc.; oils such as sesame oil, olive oil, soybean oil, etc.; antiseptics such as p-hydroxybenzoic acid esters, etc.; flavors such as strawberry flavor, peppermint flavor, etc.; and the like. Capsules, tablets, powders and granules can be produced using, as additives, fillers such as lactose, glucose, sucrose, mannitol, etc.; disintegrating agents such as starch sodium alginate, etc.; lubricants such as magnesium stearate, talc, etc.; binders such as polyvinyl alcohol, hydroxypropylcellulose, gelatin, etc.; surfactants such as a fatty acid ester, etc.; plasticizers such as glycerol, etc.; and the like.

Examples of the pharmaceutical production suitable for parenteral administration include injections, suppositories, sprays and the like. For example, injections are produced using a carrier such as a salt solution, a glucose solution, a mixture of thereof and the like. Suppositories are produced using a carrier such as cacao butter, hydrogenated fat, carboxylic acid or the like. Also, sprays are produced using the active ingredient as such or using a carrier which does not stimulate the buccal or airway mucous membrane of the patient and can facilitate absorption of the active ingredient by dispersing it as fine particles. Specific examples of the carrier include lactose, glycerine and the like. Depending on the properties of the active ingredient and the carrier, it is possible to produce other pharmaceutical productions such as aerosols, dry powders and the like. In addition, the components exemplified as additives for oral productions can also be added to these parenteral productions.

Although the clinical dose or the frequency of administration varies depending on various conditions such as the intended therapeutic effect, administration method, treating period, age and body weight, it is usually from 10 µg/kg to 8 mg/kg per day per adult.

7. Method for Obtaining Antibody which Recognizes Stroma Cell

An antibody such as a polyclonal antibody, a monoclonal antibody and the like which recognize the stroma cell of the present invention can be produced using the stroma cell of the present invention as the antigen. A large number of studies have been reported on the production, using a cell as the antigen, of an antibody specific for the surface of the cell used as the antigen and of an antigen molecule recognized by the antibody (N. Itoh et al., *Cell,* 66, 233 (1991)), and currently a large number of surface antigen molecules have been identified to be known as CD antigens.

Similar to the production of antibodies using proteins and peptides as the antigen, techniques for preparing antibodies capable of recognizing cell surface molecules using cells as the antigen have been established, so that an antibody which recognizes the stroma cell of the present invention can be produced, e.g., by the following method.

(1) Production of Polyclonal Antibody

A polyclonal antibody can be produced by using the stroma cell to be used in the present invention as the antigen and administering it into an animal.

Examples of the useful animal to be administered include rabbit, goat, 3-20 weeks-old rat, mouse, hamster and the like.

It is preferred that the dose of the antigen is $10^4$ to $10^8$ cells, or 0.01 to 10 mg as a cell membrane fraction produced from the cells, per one animal.

The immunogen is administered by subcutaneous or intraperitoneal injection together with an appropriate adjuvant (e.g., complete Freund's adjuvant, a combination of aluminum hydroxide gel with pertussis vaccine, and the like).

The immunogen is administered 3 to 10 times at intervals of 1 to 2 weeks after the first administration. Three to seven days after each administration, a blood sample is taken from the venous plexus of the eyegrounds, and the serum derived from the sample is tested as to whether it is reactive with the antigen used in the immunization, for example, by enzyme immunoassay (*Enzyme-linked Immunosorbent Assay* (*ELISA*), published by Igaku Shoin (1976), *Antibodies, A Laboratory Manual*, Cold Spring Harbor Laboratory (1988) (hereinafter referred to as "*Antibodies, A Laboratory Manual*"), a method using a flow cytometer (*Monoclonal Antibodies*) or the like.

It is already known that a cell membrane component of cells used as the antigen can be produced using many known methods, for example, it can be produced by the method of Jones et al. (D. H. Jones and A. L. Matus, *Biochim. Biophys. Acta.,* 356, 276 (1974)) using a difference in sucrose density gradient, and the enzyme immunoassay can be carried out using a plate coated with this cell membrane component.

A polyclonal antibody can be obtained by preparing a serum sample from a non-human mammal in which its serum showed a sufficient antibody titer for the antigen used in the immunization and separating and purifying the antibody from the serum.

Examples of the separation and purification method include centrifugation, salting out with 40 to 50% saturation ammonium sulfate, caprylic acid precipitation (*Antibodies, A Laboratory Manual*), chromatography using, e.g., a DEAE-Sepharose column, an anion exchange column, a protein A- or G-column, a gel filtration column, etc., and the like, which may be used alone or as a combination.

(2) Production of Monoclonal Antibody (a) Production of Antibody Producing Cell

A mouse or rat in which its serum showed a sufficient antibody titer for the stroma cell of the present invention used in the immunization is submitted for use as a supply source of the antibody producing cell.

Three to seven days after the final administration of the cell used as the antigen into the mouse or rat which showed the antibody titer, the spleen is excised.

The spleen is cut to pieces in MEM medium (manufactured by Nissui Pharmaceutical), the cells are unbound using a pair of forceps and centrifuged at 1,200 rpm for 5 minutes, and then the supernatant is discarded.

Splenocytes in the thus obtained precipitation fraction are treated with Tris-ammonium chloride buffer (pH 7.65) for 1 to 2 minutes to eliminate erythrocytes and then washed three times with MEM medium, and the thus obtained splenocytes are used as the antibody producing cells.

(b) Production of Myeloma Cells

Cells of a cell line which have been obtained from mouse or rat are used as the myeloma cells. For example, the 8-azaguanine-resistant mouse (BALB/c-derived) myeloma cell lines P3-X63Ag8-U1 (hereinafter referred to as "P-3-U1") (*Curr. Topics in Microbiol. Immunol.*, 81, 1 (1978)); *Europ. J. Immunol.*, 6, 511(1976)), SP2/O-Ag14 (SP-2) (*Nature*, 276, 269 (1978)), P3-X63-Ag8653 (653) (*J. Immunol.*, 123, 1548 (1979)), P3-X63-Ag8 (X63) (*Nature*, 256, 495 (1975)) or the like may be used. These cell lines are subcultured in an 8-azaguanine medium (produced by supplementing RPMI-1640 medium with glutamine (1.5 mM), 2-mercaptoethanol ($5 \times 10^{-5}$ M), gentamicin (10 μg/ml) and fetal calf serum (FCS) (manufactured by CSL; 10%) (hereinafter referred to as "normal medium") and further supplementing the resulting medium with 8-azaguanine (15 μg/ml)), culturing is carried out 3 to 4 days before cell fusion in the normal medium, and $2 \times 10^7$ or more of the cells are used in the cell fusion.

(c) Production of Hybridoma

The antibody producing cells obtained in (a) and the myeloma cells obtained in (b) are washed well with MEM or PBS (1.83 g of disodium phosphate, 0.21 g of monopotassium phosphate and 7.65 g of sodium chloride per liter of distilled water, pH 7.2), and mixed in a proportion of antibody producing cells: myeloma cell=5 to 10:1, the mixture is centrifuged at 1,200 rpm for 5 minutes and then the supernatant is discarded.

The cells of the thus obtained precipitation fraction are thoroughly disintegrated, 0.2 to 1 ml of a mixture solution containing 2 g of polyethylene glycol-1,000 (PEG-1,000), 2 ml of MEM and 0.7 ml of dimethyl sulfoxide (DMSO) is added to the cells per $10^8$ antibody producing cells with stirring at 37° C., then 1 to 2 ml of MEM is added several times at 1- to 2-minute intervals.

After the addition, the total volume is adjusted to 50 ml by adding MEM. After centrifugation of the thus produced solution at 900 rpm for 5 minutes, the supernatant is discarded. The cells of the thus obtained precipitation fraction are loosened gently and then suspended in 100 ml of HAT medium (produced by supplementing the normal medium with hypoxanthine ($10^{-4}$ M), thymidine ($1.5 \times 10^{-5}$ M) and aminopterin ($4 \times 10^{-7}$ M)) by repeated drawing up and discharging using a measuring pipette.

This suspension is dispensed in 100 μl into each well of a 96-well incubation plates and incubated in a 5% $CO_2$ incubator at 37° C. for 7 to 14 days.

After the incubation, a part of the culture supernatant is taken from each well, and a hybridoma which specifically reacts with the stroma cell of the present invention is selected by the enzyme immunoassay described in, for example, *Antibodies, A Laboratory Manual*, or by the flow cytometer method described in, for example, *Monoclonal Antibodies*.

Specific examples of the enzyme immunoassay are shown below.

An appropriate plate is coated with the cell membrane fraction produced from the stroma cell of the present invention used as the antigen in immunization, the plate is allowed to react with a hybridoma culture supernatant or the purified antibody obtained in the following procedure (d), as a first antibody, and then with an anti-rat or anti-mouse immunoglobulin antibody as a second antibody labeled with biotin, an enzyme, a chemiluminescent substance, a radioactive compound or the like, and then a reaction suitable for the label is carried out to select a hybridoma which produces an antibody specifically reacting with the stroma cell of the present invention as a hybridoma which produces the monoclonal antibody of the present invention.

A specific method using a flow cytometer is shown below.

The cells used as the antigen are allowed to react with a hybridoma culture supernatant or the purified antibody obtained in the following procedure (d) as a first antibody, and then with an anti-mouse or anti-rat immunoglobulin antibody as a second antibody labeled with biotin, a fluorescent material or the like, or further with a fluorescent-labeled avidin when a biotin-labeled second antibody is used, and then the presence of staining is confirmed using a flow cytometer such as FACS to select a hybridoma which produces an antibody specifically reacting with the stroma cell of the present invention as a hybridoma which produces the monoclonal antibody of the present invention.

Using the hybridoma, cloning is repeated twice by limiting dilution (using HT medium (HAT medium minus aminopterin) for the first cloning and the normal medium for the second), and a line for which a high antibody titer is constantly observed is selected as a hybridoma which produces the monoclonal antibody of the present invention.

(d) Production of Monoclonal Antibody

The monoclonal antibody producing hybridoma cells of the present invention obtained in (c) are intraperitoneally injected into 8 to 10 weeks-old mice or nude mice treated with pristane (by intraperitoneal administration of 0.5 ml of 2,6,10,14-tetramethylpentadecane (pristane) followed by feeding for 2 weeks) at a dose of $5 \times 10^6$ to $20 \times 10^6$ cells per animal. The hybridoma causes ascites tumor in 10 to 21 days.

The ascitic fluid is collected from the ascites tumor-caused mice and centrifuged at 3,000 rpm for 5 minutes to remove solid matter.

A monoclonal antibody can be purified and obtained from the resulting supernatant by the same method used for the production of a polyclonal antibody.

The subclass of the antibody can be determined using a mouse monoclonal antibody typing kit or a rat monoclonal antibody typing kit. The amount of protein can be determined by the Lowry method or calculated based on the absorbance at 280 nm.

As a monoclonal antibody obtained by the above method, the monoclonal antibody produced by a hybridoma FERM BP-7573 obtained in Example 15-(5) can be exemplified.

8. Preparation of Antigen Recognized by the Antibody of the Present Invention

The antibody obtained by using the stroma cell of the invention produced in the above section 4 recognizes antigen molecules existing on many cell surfaces. Thus, antigen molecules recognized by the antibody can be obtained by using the thus produced antibody. Specifically, it can be carried out using the expression cloning techniques described in, for example, *Molecular Cloning*, Second Edition, *Current Protocols in Molecular Biology, Monoclonal Antibodies* or *Antibody Engineering*.

Specifically, for example, cDNA is produced from the stroma cell of the present invention and the cDNA is inserted into downstream of the promoter of an appropriate expression vector to prepare a recombinant vector and a cDNA library. By introducing the recombinant vector into a host cell suited for the expression vector, transformants capable of producing gene products produced by the stroma cell of the present invention are obtained, and a transformant which produces a gene product which reacts with the antibody of the present invention is selected therefrom. An antigen molecule recognized by the antibody of the present invention can be obtained by determining the gene sequence encoded by the cDNA introduced into the selected transformant.

The present invention will be explained in detail below.

Any of bacteria, yeast, animal cells, insect cells, plant cells and the like can be used as the host cell, so long as it can express the target gene. Examples of the expression vector include those which can autonomously replicate in the above host cell or which can be integrated into a chromosome and have a promoter at an operative position such that the DNA encoding the antigen of the present invention can be transcribed.

First, total RNA is prepared from a stroma cell used in the present invention. Examples of the method includes a guanidine thiocyanate-cesium trifluoroacetate method (*Methods in Enzymol.*, 154, 3 (1987)), an acidic thiocyanate guanidine-phenol-chloroform (AGPC) method (*Analytical Biochemistry*, 162, 156 (1987), *Experimental Medicine*, 9, 1937 (1991))) and the like. Examples of the method for preparing mRNA from total RNA include an oligo (dT) immobilized cellulose column method (*Molecular Cloning*, Second Edition) and the like. Also, mRNA can be prepared by using a kit such as Fast Track mRNA Isolation Kit (manufactured by Invitrogen), Quick Prep mRNA Purification Kit (manufactured by Pharmacia) or the like.

Examples of the method for producing a cDNA library from the prepared stroma cell mRNA include methods described in *Molecular Cloning*, Second Edition, *Current Protocols in Molecular Biology*, etc.; methods using a commercially available kit, such as SuperScript Plasmid System for cDNA Synthesis and Plasmid Cloning (manufactured by Life Technologies), ZAP-cDNA Synthesis Kit (manufactured by STRATAGENE), etc.; and the like.

As the vector for producing cDNA library, any of a phage vector, plasmid vector and the like can be used, so long as it can autonomously replicate in a microorganism such as *Escherichia coli* K12 or the like and can express cDNA which is introduced into the host cell.

When a phage is used as the host cell, a transformant to which the prepared cDNA has been introduced can be obtained, for example, by using a commercially available kit Recombinant Phage Antibody System (manufactured by Pharmacia).

When prokaryote such as a bacterium or the like is used as the host cell, it is preferred that the recombinant vector comprising the prepared cDNA can autonomously replicate in the prokaryote and is constructed with a promoter, a ribosome binding sequence, the cDNA gene and a transcription termination sequence. A promoter-controlling gene may be contained therein.

Examples of the expression vector include pBTrp2, pBTac1 and pBTac2 (manufactured by Boehringer Mannheim), pKK233-2 (manufactured by Pharmacia), pSE280, pSE380 and pSE420 (manufactured by Invitrogen), pAX and pMEX (manufactured by MOBITEC), pGEMEX-1 (manufactured by Promega), pQE-8 (manufactured by QIAGEN), pKYP10 (Japanese Published Unexamined Patent Application No. 110600/83), pKYP200 (*Agric. Biol. Chem.*, 48, 669 (1984)), pLSA1 (*Agric. Biol. Chem.*, 53, 277 (1989)), pGEL1 (*Proc. Natl. Acad. Sci. USA*, 82, 4306 (1985)), pBluescript II SK(−) (manufactured by Stratagene), pTrs30 (prepared from *Escherichia coli* JN109/pTrS30 (FERM BP-5407)), pTrs32 (prepared from *Escherichia coli* JN109/pTrS32 (FERM BP-5408), pGHA2 (prepared from *Escherichia coli* IGHA2 (FERM B-400), Japanese Published Unexamined Patent Application No. 221091/85), pGKA2 (prepared from *Escherichia coli* IGKA2 (FERM BP-6798), Japanese Published Unexamined Patent Application No. 221091/85), pTerm2 (U.S. Pat. No. 4,686,191, U.S. Pat. No. 4,939,094, U.S. Pat. No. 5,160,735), pSupex, pUB110, pTP5, pC194 and pEG400 (*J. Bacteriol*, 172, 2392 (1990)), pGEX (manufactured by Amersham Pharmacia Biotech), pET system (manufactured by Novagen) and the like.

As the promoter, any promoter can be used, so long as it can function in a host cell. Examples include promoters derived from *Escherichia coli*, phage and the like, such as trp promoter ($P_{trp}$), lac promoter, $P_L$ promoter, $P_R$ promoter, T7 promoter and the like. Also, artificially designed and modified promoters, such as a promoter in which two $P_{trp}$ are linked in series ($P_{trp} \times 2$), tac promoter, lacT7 promoter, letI promoter and the like, can be used.

A plasmid in which the space between Shine-Dalgarno sequence which is a ribosome binding sequence and the initiation codon is adjusted to a suitable distance (for example, 6 to 18 nucleotides) is preferably used.

Examples of the host cell include microorganisms belonging to the genus Escherichia, the genus Serratia, the genus Bacillus, the genus Brevibacterium, the genus Corynebacterium, the genus Microbacterium, the genus Pseudomonas and the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Serratia ficaria*, *Serratia fonticola*, *Serratia liquefaciens*, *Serratia marcescens*, *Bacillus subtilis*, *Bacillus amyloliquefaciens*, *Brevibacterium ammoniagenes*, *Brevibacterium immariophilum* ATCC 14068, *Brevibacterium saccharolyticum* ATCC 14066, *Brevibacterium glutamicum* ATCC 14067, *Brevibacterium glutamicum* ATCC 13869, *Corynebacterium glutamicum* ATCC 13032, *Corynebacterium acetoacidophilum* ATCC 13870, *Microbacterium ammoniaphilum* ATCC 15354, Pseudomonas sp. D-0110 and the like.

As the method for introducing the recombinant vector, any method can be used, so long as it is a method for introducing DNA into the above host cell. Examples include a method using a calcium ion (*Proc. Natl. Acad. Sci. USA,* 69, 2110 (1972)), a protoplast method (Japanese Published Unexamined Patent Application No. 248394/88), methods described in *Gene,* 17, 107 (1982) and *Molecular & General Genetics,* 168, 111 (1979), and the like.

When yeast is used as the host cell, examples of the expression vector include YEP13 (ATCC 37115), YEp24 (ATCC 37051), YCp50 (ATCC 37419) and the like.

Any promoter can be used, so long as it can function in yeast. Examples include a promoter of a gene in the glycolysis system such as hexose kinase, etc., PHO5 promoter, PGK promoter, GAP promoter, ADH promoter, gal 1 promoter, gal 10 promoter, a heat shock polypeptide promoter, MFα1 promoter, CUP 1 promoter and the like.

Examples of the host cell include microorganisms belonging to the genus Saccharomyces, the genus Schizosaccharomyces, the genus Kluyveromyces, the genus Trichosporon, the genus Schwanniomyces and the like. Specific examples include *Saccharomyces cerevisiae, Schizosaccharomyces pombe, Kluyveromyces lactis, Trichosporon pullulans, Schwanniomyces alluvius* and the like.

As the method for introducing the recombinant vector, any method can be used, so long as it is a method for introducing DNA into yeast. Examples include electroporation (*Methods in Enzymology,* 194, 182 (1990)), a spheroplast method (*Proc. Natl. Acad. Sci. USA,* 84, 1929 (1978)), a lithium acetate method (*J. Bacteriology,* 153, 163 (1983)), a method described in *Proc. Natl. Acad. Sci. USA,* 75, 1929 (1978) and the like.

When an animal cell is used as the host, examples of the expression vector include pcDNAI and pcDM8 (manufactured by Funakoshi), pAGE107 (Japanese Published Unexamined Patent Application No. 22979/91; *Cytotechnology,* 3, 133 (1990)), pAS3-3 (Japanese Published Unexamined Patent Application No. 227075/90), pcDM8 (*Nature,* 329, 840 (1987)), EBV Vector (manufactured by Inbitrogen), pRc/CMV2 (manufactured by Invitrogen), pRc/RSV (manufactured by Invitrogen), pZeoSV Vector (manufactured by Invitrogen), pcDNAI/amp (manufactured by Invitrogen), pDisplayp (manufactured by Invitrogen), REP4 (manufactured by Invitrogen), pcDNA3.1 Vector (manufactured by Invitrogen), pXT1 (manufactured by Invitrogen), pSG5 (manufactured by Invitrogen), pBK-CMV (manufactured by Stratagene), pBK-RSV (manufactured by Stratagene), pAGE103 (*J. Biochemistry,* 101, 1307 (1987)), pAGE210 and the like.

Any promoter can be used, so long as it can function in the animal cell. Examples include a promoter of IE (immediate early) gene of cytomegalovirus (CMV), an early promoter of SV40, a promoter of retrovirus, a metallothionein promoter, a heat shock promoter, SRα promoter and the like. Also, the enhancer of the IE gene of human CMV can be used together with the promoter.

Examples of the host cell include human Namalwa cell, monkey COS cell, Chinese hamster CHO cell, HBT5637 (Japanese Published Unexamined Patent Application No. 299/88) and the like.

As the method for introducing the recombinant vector, any method can be used, so long as it is a method for introducing DNA into an animal cell. Examples include electroporation (*Cytotechnology,* 3, 133 (1990)), a calcium phosphate method (Japanese Published Unexamined Patent Application No. 227075/90), a lipofection method (*Proc. Natl. Acad. Sci. USA,* 84, 7413 (1987)) and the like.

When an insect cell is used as the host, a protein can be expressed by a method described in, for example, *Current Protocols in Molecular Biology, Bacurovirus Expression Vectors, A Laboratory Manual,* W. H. Freeman and Company, New York (1992), *Bio/Technology,* 6, 47 (1988) or the like.

Specifically, a vector for recombinant gene introduction and a baculovirus are cotransfected into an insect cell to thereby obtain a recombinant virus in an insect cell culture supernatant, and then the insect cell is infected with the recombinant virus to express a protein.

Examples of the vector for gene introduction used in the method include pVL1392, pVL1393, pBlueBacIII (all manufactured by Invitrogen) and the like.

Examples of the bacurovirus include *Autographa californica* nuclear polyhedrosis virus which infects insects of the family Barathra and the like.

Examples of the insect cell include Sf9 and Sf21 which are *Spodoptera frugiperda* ovary cells (*Baculovirus Expression Vectors, A Laboratory Manual,* W. H. Freeman and Company, New York (1992)), High 5 which is *Trichoplusia ni* ovary cell and the like.

The method for cotransfecting the above vector for recombinant gene introduction and the above bacurovirus for the preparation of the recombinant virus include a calcium phosphate method (Japanese Published Unexamined Patent Application No. 227075/90), a lipofection method (*Proc. Natl. Acad. Sci. USA,* 84, 7413 (1987)) and the like.

When a plant cell is used as the host cell, examples of the expression vector include Ti plasmid, tobacco mosaic virus vector and the like.

As the promoter, any promoter can be used, so long as it can function in a plant cell. Examples include cauliflower mosaic virus (CaMV) 35S promoter, rice actin 1 promoter and the like.

Examples of the host cell include plant cells such as tobacco, potato, tomato, carrot, soybean, rape, alfalfa, rice, wheat, barley and the like.

As the method for introducing the recombinant vector, any method can be used, so long as it is a method for introducing DNA into a plant cell. Examples include a method using Agrobacterium (Japanese Published Unexamined Patent Application No. 140885/84, Japanese Published Unexamined Patent Application No. 70080/85, WO94/00977), electroporation (Japanese Published Unexamined Patent Application No. 251887/85), a method using a particle gun (gene gun) (Japanese Patent No. 2606856, Japanese Patent No. 2517813) and the like.

The thus-obtained transformant is cultured in a medium to express a gene product encoded by the cDNA introduced. Culturing of the transformant in a medium may be carried out according to a method generally carried out in culturing a host.

As a medium for culturing the transformant obtained by using, as the host, prokaryote such as *Escherichia coli* or the like or eukaryote such as yeast or the like, the medium may be either a natural medium or a synthetic medium, so long as it contains a carbon source, a nitrogen source, an inorganic salt and the like which can be assimilated by the organism and the transformant can be cultured efficiently.

Any carbon source can be used, so long as it can be assimilated by the organism. Examples include carbohydrates, such as glucose, fructose, sucrose, molasses containing them, starch, starch hydrolysate, etc.; organic acids, such as acetic acid, propionic acid, etc.; alcohols, such as ethanol, propanol, etc.; and the like.

Examples of the nitrogen source include ammonia; ammonium salts of inorganic acids or organic acids, such as ammonium chloride, ammonium sulfate, ammonium acetate, ammonium phosphate, etc., other nitrogen-containing compounds, peptone, meat extract, yeast extract, corn steep liquor, casein hydrolysate, soybean meal, soybean meal hydrolysate, various fermented cells, hydrolysates thereof and the like.

Examples of the inorganic salt include potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is generally carried out under aerobic conditions by shaking culture, deep aeration stirring culture or the like. The culturing temperature is preferably 15 to 40° C. The culturing time is generally 16 to 7 days. The pH is maintained at 3.0 to 9.0 during culturing. The pH is adjusted using inorganic or organic acid, an alkali solution, urea, calcium carbonate, ammonia or the like.

Also, if necessary, antibiotics such as ampicillin, tetracycline and the like can be added to the medium during culturing.

When a microorganism transformed with an expression vector using an inducible promoter as the promoter is cultured, an inducer may be added to the medium, if necessary. For example, when a microorganism transformed with an expression vector using lac promoter is cultured, isopropyl-β-D-thiogalactopyranoside or the like can be added to the medium, and when a microorganism transformed with an expression vector using trp promoter is cultured, indoleacrylic acid or the like can be added to the medium.

Examples of the medium for culturing a transformant obtained by using an animal cell as the host include generally used RPMI 1640 medium (*The Journal of the American Medical Association*, 199, 519 (1967)), Eagle's MEM (*Science*, 122, 501 (1952)), Dulbecco modified MEM medium (*Virology*, 8, 396 (1959)), 199 Medium (*Proceeding of the Society for the Biological Medicine*, 73, 1 (1950)), media obtained by adding fetal calf serum or the like to these media, and the like.

Culturing is generally carried out, for example, at pH of 6 to 8 and at 30 to 40° C. for 1 to 7 days in the presence of 5% $CO_2$.

Furthermore, if necessary, antibiotics such as kanamycin, penicillin and the like can be added to the medium during culturing.

Examples of the medium for culturing a transformant obtained by using an insect cell as the host include generally used TNM-FH medium (manufactured by Pharmingen), Sf-900 II SFM (manufactured by Life Technologies), ExCell 400 and ExCell 405 (both manufactured by JRH Biosciences), Grace's Insect Medium (*Nature*, 195, 788 (1962)) and the like.

Culturing is generally carried out, for example, at pH of 6 to 7 and at 25 to 30° C. for 1 to 5 days.

Furthermore, if necessary, antibiotics such as gentamicin and the like can be added to the medium during culturing.

A transformant obtained by using a plant cell as the host can be used as the cell or after differentiating to a plant cell or organ. Examples of the medium used for culturing the transformant include generally used Murashige and Skoog (MS) medium, White medium, media to which a plant hormone such as auxin, cytokinine or the like has been added, and the like.

Culturing is generally carried out at a pH of 5 to 9 and at 20 to 40° C. for 3 to 60 days.

Also, if necessary, antibiotics such as kanamycin, hygromycin and the like can be added to the medium during culturing.

As described above, a transformant derived from a microorganism, an animal cell or a plant cell comprising a recombinant vector to which cDNA prepared from a stroma cell used in the present invention has been inserted is cultured according to the generally used culturing method to thereby produce a transformant expressing a gene product encoded by the cDNA.

Examples of a method for selecting a transformant which produces a gene product which reacts with the antibody of the present invention include enzyme immunoassay described in *Antibodies, A Laboratory Manual; Monoclonal Antibodies; Antibody Engineering; Enzyme Immunoassay*, Third Edition, Igaku Shoin (1987) and the like, a method using a flow cytometer described in *Antibodies, A Laboratory Manual; Monoclonal Antibodies; Antibody Engineering; Int. Immunol.*, 10, 275 (1998); *Exp. Hematol.*, 25, 972 (1997) and the like, and the Panning method described in *Monoclonal Antibodies; Antibody engineering; J. Immunol.*, 141, 2797 (1988) and the like.

As a method for isolating cDNA which has been introduced into the selected transformant, when an expression vector which can autonomously replicate is used in a host cell, the method includes a generally used method which recovers a phage vector or a plasmid vector described in *Molecular Cloning*, Second Edition; *Current Protocols in Molecular Biology; Mol. Cell. Biol.*, 8, 2837 (1988) and the like, and the Hirt method. When an expression vector which is integrated into a chromosome is used, cNDA which is to be introduced into a host is classified into groups of various kinds (e.g., 100 to 1000 kinds) and pooled, the group which provides the target transformant is classified into groups having few kinds (e.g., 10 to 100 kinds) and pooled, and this classification and pooling are repeated to thereby isolate the target cDNA.

The nucleotide sequence of the isolated cDNA is analyzed from its end according to a generally used nucleotide sequence analyzing method such as the dideoxy method of Sanger et al. (*Proc. Natl. Acad. Sci. USA*, 74, 5463 (1997)) or by using a nucleotide sequence analyzing apparatus such as ABIPRISM377DNA sequencer (manufactured by PE Biosystems) or the like to thereby determine the nucleotide sequence of the DNA.

As described above, the antigen molecule recognized by the antibody of the present invention can be obtained by using the method for expression cloning.

In the present invention, expression cloning is preferably carried out using a cell having no activity of inducing differentiation of an embryonic stem cell into an ectoderm-derived cell (for example, as described in Example 3 below).

Specific examples include an expression cloning method in which a cell having no activity of inducing differentiation of an embryonic stem cell into an ectoderm-derived cell is used as the host cell, cDNA prepared from a stroma cell according to the present invention is introduced thereinto and expressed, and the antigen molecule is selected using an antibody which recognizes the stroma cell according to the present invention.

Examples of the cell having no activity of inducing differentiation of an embryonic system cell into an ectoderm-derived cell include CHO cell derived from Chinese hamster ovary (T. T. Puck et al., *J. Exp. Med.*, 108, 945 (1985)), COS cell derived from African grivet kidney cell (Y. Gluzman, *Cell*, 23, 175 (1981)), MDCK cell derived from a female cocker spaniel kidney (C. R. Gaush et al., *Proc. Soc. Exp. Biol. Med.*, 122, 931 (1966); D. S. Misfeldt et al., *Proc. Natl. Acad. Sci. USA*, 73, 1212 (1976)) and a rat fibroblast 3Y1 (S. Sandineyer et al., *Cancer Res.*, 41, 830 (1981)). Accordingly, CHO cell, MDCK cell and 3Y1 cell are preferably used, and COS cell which is suitable for expression cloning using an SV40 expression vector is more preferably used.

In addition to the expression cloning method, an antibody which recognizes a stroma cell according to the present invention can be used to obtain an antigen molecule recognized by the antibody. Specific examples include a method in which the stroma cell according to the present invention is used as the starting material, the reactivity with the antibody is measured using the above-described enzyme immunoassay, and the antigen can be purified using the measured value as the index.

More specifically, stroma cells according to the present invention are recovered by centrifugation and suspended in an aqueous buffer, and then the cells are disrupted with an ultrasonicator, a French press, a Manton Gaulin homogenizer, a Dynomill, surfactant treatment or the like to obtain a cell-free extract. From the supernatant obtained by centrifuging the cell-free extract, an antigen purified product can be obtained by the general method used for isolating and purifying an enzyme, for example, solvent extraction, salting out using ammonium sulfate or the like, desalting, precipitation using an organic solvent, anion exchange chromatography using a resin, such as diethylaminoethyl (DEAE)-Sepharose, DIAION HPA-75 (manufactured by Mitsubishi Chemical) or the like, cation exchange chromatography using a resin, such as S-Sepharose FF (manufactured by Pharmacia) or the like, hydrophobic chromatography using a resin, such as butyl sepharose, phenyl sepharose or the like, gel filtration using a molecular sieve, affinity chromatography, chromatofocusing, or electrophoresis, such as isoelectric focusing or the like, alone or in combination thereof.

9. Application of Method for Inducing Differentiation, Cell, Antibody, Antigen and Agent for Inducing Differentiation of the Present Invention (1) Method for Evaluating or Screening Substance Using the Method for Inducing Differentiation of the Present Invention The method of the present invention for inducing differentiation of an embryonic stem cell into an ectodermal cell or ectoderm-derived cell is useful for the pharmacological evaluation and activity evaluation of substances such as a physiologically active substance (for example, a drug) and a novel gene product whose functions are unknown, in the differentiation process of these cells or in the cell function regulation. It is also useful for the function evaluation of a gene in the differentiation method of an embryonic stem cell into an ectodermal cell or ectoderm-derived cell, by using an embryonic stem cell in which the specified gene is modified.

For example, the application method of the culturing method of the present invention are shown below.

According to the method for inducing differentiation of the present invention, influences upon the differentiation process into an ectodermal cell or ectoderm-derived cell or upon the functional regulation of an ectodermal cell or an ectoderm-derived cell of a test substance added to the medium can be evaluated. Any substance can be used as the substance to be tested, so long as it can be added to the culturing system. Examples include a low molecular weight compound, a high molecular weight compound, an organic compound, an inorganic compound, a protein, a gene, a virus, a cell and the like. The substances to be tested, excluding genes, may be added directly to the culture medium.

Examples of the method for efficiently introducing a gene into the culture system include a method in which the gene is added to the culture system by carrying it on a virus vector such as retrovirus, adenovirus, adeno-associated virus, herpes simplex virus or lentivirus and a method in which it is added to the culture system by including into an artificial vesicle structure such as liposome. Specific examples include reports on the analysis of genes using recombinant virus vectors (*Proc. Natl. Acad. Sci. USA,* 92, 6733 (1995); *Nucleic Acids Res.,* 18, 3587 (1990); *Nucleic Acids Res.,* 23, 3816 (1995)).

These substances to be tested can be added to the culture system in the differentiation induction method at any stage, for example, each substance to be tested can be evaluated by adding it at a relatively early stage of the culturing when it is necessary to evaluate its action on a differentiation step of the stem cell into an ectodermal cell, or at a relatively latter stage of culturing when it is necessary to evaluate its action on a differentiation step of an ectodermal cell into an ectoderm-derived cell. In order to judge the differentiating degree in the culture system, it can be understood by examining expression of a marker protein of respective differentiated cell formed as a result of its differentiation from the embryonic stem cell. The evaluation or screening of a substance to be tested can be carried out, e.g., by measuring qualitative or quantitative changes in the differentiation efficiency into an ectodermal cell or ectoderm-derived cell after a predetermined period of culturing. Examples of the method for measuring qualitative changes include a method in which van Inzen et al. have measured the action potential using a nerve cell differentiation-induced from an embryonic stem cell (*Biochim. Biophys. Acta.,* 1312, 21 (1996)).

(2) Cell-Containing Medicament

The stroma cell used in the present invention or factors derived from the stroma cell of the present invention, or an ectodermal cell or an ectoderm-derived cell obtained by carrying out differentiation induction of an embryonic cell using them, can be used as a medicament for treating, diagnosing or preventing diseases caused by the disorder of ectoderm-derived cells.

Examples of the diseases caused by the disorder of ectoderm-derived cells include various diseases described in the above section 6 (2).

Examples of the therapeutic agent for diseases caused by the disorder of ectoderm-derived cells include a cell having the same function of the cell which caused a disorder, a precursor of the cell which caused a disorder, a cell which can compensate function of the disordered cell or a cell having a function to accelerate regeneration of the disordered cell, which can be applied to the transplantation medical treatment.

The therapeutic agent of the present invention can be produced by preparing an ectodermal cell or an ectoderm-derived cell obtained by its differentiation induction from an embryonic stem cell and using it as the active ingredient. Also, the therapeutic agent of the present invention may be produced by preparing a stroma cell in the manner as described in 4 as mentioned above, or a factor derived from a stroma cell in the manner as described in 5 as mentioned above, and using it as the active ingredient. The therapeutic agent of the present invention functions to accelerate regeneration of disordered cells in diseases caused by the disorder of ectoderm-derived cells.

Any one of the already known methods for separating and purifying cells can be used as the method for increasing purity of cells. Examples include a method using a flow cytometer described in, for example, *Antibodies, A Laboratory Manual, Monoclonal Antibodies, Antibody Engineering, Int. Immunol.,* 10, 275 (1998), *Exp. Hematol.,* 25, 972 (1997) or the like, a panning method described in, for example, *Monoclonal Antibodies, Antibody Engineering, J. Immunol.,* 141, 2797 (1988) or the like, and a cell fractionation method using density difference of sucrose concentration described in, for example, *Techniques of Tissue Culture* (Third Edition), Asakura Shoten (1996).

The method for increasing purity of a cell differentiation-induced from an embryonic stem cell, according to the present invention, comprises culturing the ectodermal cell or ectoderm-derived cell obtained by differentiation-inducing the embryonic stem cell, in a medium comprising an antitumor agent.

Since cells under an undifferentiated state can be removed by this step, differentiated cells can be obtained with further higher purity, so that the product becomes more suitable as a medicament. That is, by the treatment with an antitumor agent, cells other than the target differentiated cell, such as undifferentiated cells, can be removed. It is considered that such undifferentiated cells will become a cause of teratoma, but the danger can be avoided by treating with an antitumor agent.

Examples of the antitumor agent include mitomycin C, 5-fluorouracil, adriamycin, ara-C, methotrexate and the like. It is preferable to use these antitumor agents at a concentration which shows stronger cytotoxicity on undifferentiated cells than that on differentiated cells. Specifically, the optimum concentration can be determined by carrying out culturing using these antitumor agents according to the method described in 4, such as a method in which culturing is carried out at 37° C. for several hours, preferably 2 hours, in a stream of 5% carbon dioxide in a $CO_2$ incubator, using a medium comprising any of these antitumor agents at a concentration of 1/100 to 1 equivalent of the concentration used in the living body described in *The Pharmacopoeia of Japan*.

Any medium may be used in this method, so long as it is capable of culturing differentiation-induced cells, The medium described in 2 can be exemplified. Also, these antitumor agents can be used in differentiation-induced cells according to the method described in 4.

The therapeutic agent of the present invention may further contain pharmaceutically acceptable physiological saline, additives and/or a medium, in addition to the cells (including an ectodermal cell or ectoderm-derived cell and a stroma cell), but since it is used for the purpose of carrying out a transplantation medical treatment, it is preferable to avoid contamination of impurities such as sera, viruses and the like. A therapeutic agent comprising the factor from a stroma cell is produced by the method of the following item 9-(4), but it is preferable to avoid contamination of impurities such as sera and viruses similar to the case of the cell-containing therapeutic agent. According to the method of the present invention, differentiation of an ectodermal cell and an ectoderm-derived cell can be induced under serum-free culture conditions and without requiring an agent for inducing differentiation such as retinoic acid at a non-physiological concentration, so that it is useful in transplantation medical treatments.

In the transplantation medical treatment, rejection due to difference in the histocompatibility antigens sometimes causes a problem, but this problem can be resolved by using the embryonic stem cell described in 1-(2) into which the nucleus of a somatic cell has been transplanted or the embryonic stem cell described in 1-(3) in which a gene on the chromosome has been modified.

Also, an ectodermal cell and an ectoderm-derived cell of a somatic cell-donated individual can be obtained by carrying out differentiation induction using the embryonic stem cell described in 1-(2) into which the nucleus of a somatic cell has been transplanted. Such a cell of individual person is useful not only as a transplantation medical treatment of the cell itself but also as a diagnosing material for judging whether or not an existing agent is effective for the person. Also, since sensitivities to oxidation stress and aging can be judged by culturing a differentiation-induced cell for a prolonged period of time, risk of individual person for a disease such as a nerve degeneration disease can be evaluated by comparing its function and life with those of a cell derived from other individual, and the evaluation data are useful for providing an effective method for preventing a disease which is diagnosed as high in its future morbidity rate.

As the transplantation method, any method can be used, so long as it is a method suitable for the disease to be treated, and methods suitable for respective diseases are known. For example, an embryonic stem cell is collected from a patient and mixed with a stroma cell and a stroma cell-derived factor, and the resulting embryonic stem cell is cultured. The disease can be treated by inducing differentiation of an ectodermal cell or an ectoderm-derived cell from the embryonic stem cell and then transplanting the resulting cell into the affected part of the patient. Alternatively, the disease can also be treated by directly administering a stroma cell and a stroma cell-derived factor into the affected part of the patient. Examples of a method for transplanting a brain cell of an abortion fetus into a patient of Parkinson disease include the method described in, e.g., *Nature Neuroscience*, 2, 1137 (1999) and the like.

(3) Method for Immunologically Detecting Antigen Using Antibody, and Medicament Comprising the Antibody An antigen of the present invention or a tissue containing the antigen can be immunologically detected by allowing it to carry out an antigen-antibody reaction using an antibody which specifically recognizes the stroma cell of the present invention having activity of inducing differentiation of an embryonic stem cell into an ectodermal cell or an ectoderm-derived cell. The detection method and a medicament comprising the antibody can be applied to the diagnosis of diseases caused by the reduction or disappearance of functions of the stroma cell, such as diseases induced by the disorder of ectoderm-derived cells. This detection method can also be used in the determination of antigens.

Examples of the disease induced by a disorder of ectoderm-derived cells include various diseases described in 6-(2).

Examples of the immunological detection method include ELISA using a microtiter plate, an immunofluorescent method, western blotting, tissue immunostaining and the like. Examples of the immunological determination method include sandwich ELISA using two antibodies having different epitopes, among antibodies which react in a liquid phase with the antigen of the present invention, radioimmunoassay using the antigen of the present invention labeled with a radioisotope such as $^{125}I$ and an antibody which recognizes the antigen of the present invention, and the like.

(4) Medicament Comprising Antigen

An antigen molecule which is recognized by the antibody of the present invention and is specifically expressed in a stroma cell having activity of inducing differentiation of an embryonic stem cell into an ectodermal cell or an ectoderm-derived cell can be used as a therapeutic agent for diseases caused by the disorder of ectoderm-derived cells.

Examples of the diseases caused by the disorder of ectoderm-derived cells include various diseases described in 6-(2).

The medicament comprising the antigen of the present invention as the active ingredient can be administered by the active ingredient alone, but generally, it is preferable to provide the active ingredient as a pharmaceutical formulation produced by an optional method well known in the technical field of manufacturing pharmacy, by mixing it with one or more pharmaceutically acceptable carriers. Examples of the form, route of administration, dose and use form of these pharmaceutical formulations include those described in the above 6-(2).

The present invention is described more specifically based on the following examples, but these examples show only illustrations of the present invention and do not limit the scope of the present invention.

Example 1

Differentiation of Embryonic Stem Cell into Dopaminergic Neuron

An embryonic stem cell, ES cell EB5 (H. Niwa et al., *Nature Genet.*, 24, 372 (2000); obtained from Dr. Niwa at Department of Molecular Applied Medicine, Medical School of Osaka University) was cocultured with a stroma cell, MC3T3-G2/PA6 cell (H. Kodama et al., *J. Cell Physiol.*, 112, 89 (1982), hereinafter referred to as "PA6 cell"), or with a mouse fetal primary culture fibroblast (hereinafter referred to as "MEF cell").

Since the ES cell EB5 is gene-transferred in such a manner that a drug-resistant gene blastocidine-R is expressed in downstream region of an undifferentiation-specific promoter (Oct3 promoter; E. Pikarsky et al., *Mol. Cell. Biol.*, 14, 1026 (1994)), undifferentiated ES cell alone can be selected and maintained by culturing it by adding 20 µg/ml of blastocidine. The ES cell EB5 was used in the present invention after confirming that it survived and maintained the undifferentiated state during the testing period in a medium to which 20 µg/ml of blastocidine had been added.

The ES cell EB5 was cultured on a gelatin-coated plastic culture dish using Dulbecco's MEM medium supplemented with 10% fetal bovine serum (ES cell-qualified; manufactured by Litech Oriental), 2 mM glutamine, 100 µM MEM non-essential amino acids solution, 50 U/ml penicillin, 50 U/ml streptomycin, 100 µM 2-mercaptoethanol and 1,000 U/ml LIF (ESGRO Murine LIF; manufactured by Litech Oriental), while keeping the undifferentiated characters according to the method described in *Manipulating the Mouse Embryo, A Laboratory Manual*.

The PA6 cell was cultured according to the method of Kodama et al. (H. Kodama et al., *J. Cell Physiol.*, 112, 89 (1982)) using α-MEM medium containing 10% fetal bovine serum (manufactured by GIBCO-BRL).

The MEF cell was prepared and cultured according to the method described in *Manipulating the Mouse Embryo, A Laboratory Manual*, using Dulbecco's MEM medium supplemented with 10% fetal bovine serum (ES cell-qualified; manufactured by Litech Oriental), 2 mM glutamine, 50 U/ml penicillin and 50 U/ml streptomycin.

Differentiation of the ES cell was induced by coculturing the ES cell in a single cell state with the PA6 cell or MEF cell.

The ES cell EB5 in a single cell state was produced in the following manner.

The ES cell EB5 was proliferated to a 30% confluent by exchanging the medium. After removing the medium, the cells were washed twice using PBS(-) and then cultured at 37° C. for 20 minutes by adding PBS(-) containing 1 mM EDTA and 0.25% trypsin. The culture broth was suspended in a medium (hereinafter referred to as "serum-free medium") produced by adding 10% KNOCKOUT SR (manufactured by GIBCO BRL), 2 mM glutamine, 100 µM MEM non-essential amino acids solution, 1 mM pyruvic acid, 50 U/ml penicillin, 50 U/ml streptomycin and 100 µM 2-mercaptoethanol to the Glasgow MEM medium. The suspension was centrifuged at 4° C. and at 200×g for five minutes, and the precipitated cells were suspended again in the serum-free medium to prepare the ES cell EB5 in a single cell state.

The PA6 cell or MEF cell whose cell density reached almost confluent by exchanging the medium in advance was washed twice using PBS(-) and then suspended in the serum-free medium to prepare as feeder cells.

The ES cell EB5 in a single cell state was inoculated at a cell density of 10 to 100 cells/cm$^2$ into a culture vessel in which the thus produced PA6 cell was cultured, the medium was exchanged using a fresh serum-free medium on the 4th, 6th and 7th day, and then the cells were cultured at 37° C. for 8 days in a stream of 5% carbon dioxide in a $CO_2$ incubator. As a control, the ES cell was inoculated in the same manner into a simply gelatin-coated culture vessel and cultured in the same manner.

Eight days after coculturing, the medium in the culturing vessel was removed and the cells were fixed for 30 minutes by adding 4% p-formaldehyde solution. The thus fixed cells were immunologically stained according to the method described in *Using Antibodies*, Cold Harbor Laboratory Press (1999), using an antibody against a typical neuron marker NCAM (manufactured by Chemicon, hereinafter referred to as "anti-NCAM antibody"), an antibody against a neuron-specific marker class III β tubulin (manufactured by Babco, hereinafter referred to as "anti-tubulin antibody") and an antibody against a neural precursor cell-specific marker nestin (manufactured by Pharmingen, hereinafter referred to as "anti-nestin antibody").

PA6 cell and ES cell EB5 were cocultured for 10 days by the above method. Resulting cells in the culture vessel were fixed and then immunologically stained using an antibody against a dopaminergic neuron marker tyrosine hydroxylase (manufactured by Chemicon), an antibody against a cholinergic neuron marker VAchT (manufactured by Chemicon), an antibody against a GABAergic neuron marker GAD (manufactured by Chemicon), an antibody against a serotonergic neuron marker serotinin (manufactured by Dia Sorin) or an antibody against a noradrenaline neuron marker dopamine β-hydroxylase (manufactured by PROTOS Biotech).

Using a 3 cm dish for tissue culture (made of plastic, manufactured by FALCON) as a culturing vessel, 200 cells of the ES cell EB5 were cultured by inoculating them into each of 1) the dish produced using the PA6 cell as a feeder cell, 2) the dish produced using the MEF cell as a feeder cell and 3) the dish simply coated with gelatin, with the results shown in the drawings.

Cells of the ES cell EB5 inoculated in a single cell state adhered to the feeder cells or to the dish surface without causing mutual aggregation, repeated cell division and formed colonies (hereinafter referred to as "ES cell-derived colonies" or simply as "colonies").

Figure 2:
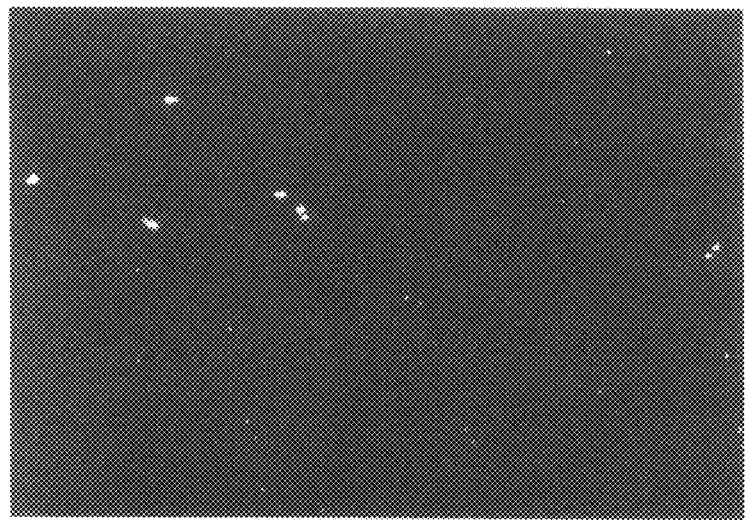
FIG. 2 is a microphotograph showing a result in which colonies formed by coculturing ES cell EB5 with MEF cell are stained with anti-NCAM antibody.
Figure 3:
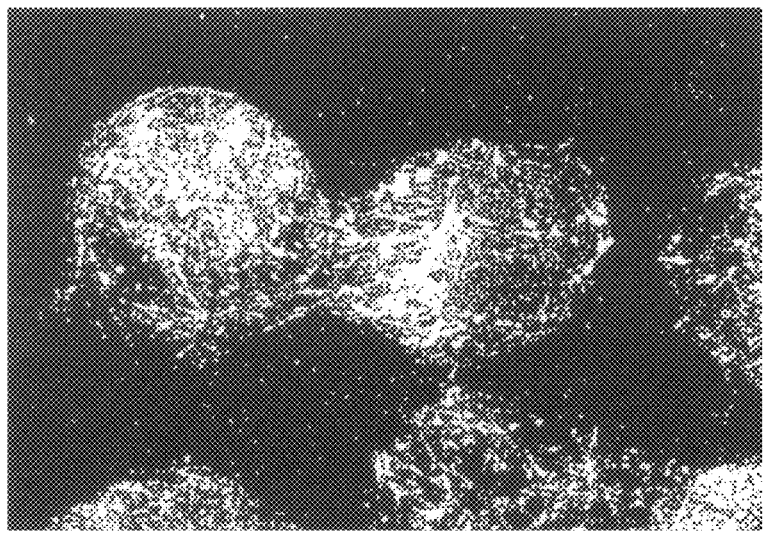
FIG. 3 is a microphotograph showing a result in which colonies formed by coculturing ES cell EB5 with PA6 cell are stained with an antibody against tyrosine hydroxylase.
Figure 4:
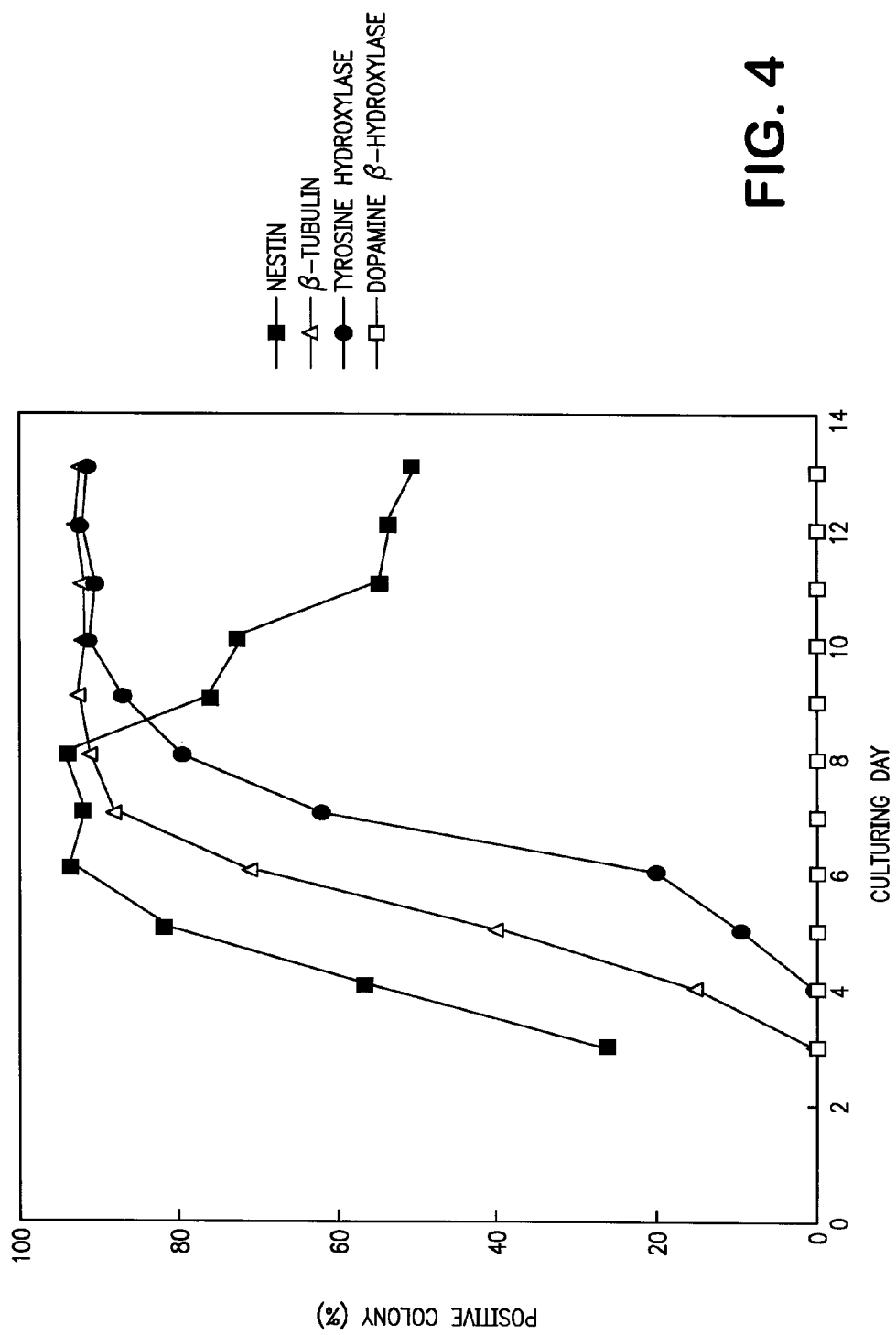
FIG. 4 is a graph showing periodical changes in the ratio of various marker positive colonies among colonies formed by coculturing ES cell EB5 with PA6 cell.

FIG. 1 shows a result of staining of the colonies formed by the coculturing with PA6 cell, with (A) the anti-NCAM antibody, (B) the anti-tubulin antibody or (C) the anti-nestin antibody. FIG. 2 shows a result of staining of the colonies formed by the coculturing with MEF cell, with the anti-NCAM antibody. FIG. 3 shows a result of staining of the colonies formed by the coculturing with PA6 cell, with an antibody against tyrosine hydroxylase (hereinafter referred to as "anti-tyrosine hydroxylase antibody"). FIG. 4 shows periodical changes in the ratio of each marker-positive colonies among colonies formed by the coculturing with PA6 cell. The ratio of colonies was calculated by preparing 160 dishes cocultured under each of the conditions 1), 2) and 3) and observing staining strength of all of the formed colonies under a microscope.

In the coculture system of the condition 1) in which the PA6 cell was prepared as a feeder cell, 90% (n=160) of colonies derived from the ES cell EB5 were strongly NCAM-positive as shown in FIG. 1A. These colonies were staining-positive with both of the anti-tubulin antibody (FIG. 1B) and anti-nestin antibody (FIG. 1C). On the other hand, the appearance of significant neuron markers was not found by coculturing with MEF cell as the condition 2) (FIG. 2). The colonies cultured on the gelatin-coated culture vessel showed the same staining result of the colonies formed by coculturing with MEF cell as the condition 2). In the coculture system of the condition 1) in which the PA6 cell was prepared as a feeder cell, anti-tyrosine hydrolase antibody-positive colonies derived from the ES cell were found at a high frequency (89%) (FIG. 3). As a result of coculturing of PA6 cell with ES cell EB5, nestin-positive colonies appeared 3 days, and tubulin-positive colonies 4 days, after starting of the coculturing, periodically as shown in FIG. 4. Also, 5 days after, tyrosine hydrolase-positive colonies appeared, and 10 days after, they reached the peak. During this period, the immunological staining with the antibody against a noradrenaline neuron marker dopamine β-hydroxylase was negative. Ten days thereafter, cholinergic neuron marker VAchT-positive colonies were formed at a frequency of 5%, GABAergic neuron marker GAD-positive colonies at a frequency of 15% and serotonin-positive colonies at 4%.

Also, a result similar to the above was obtained when coculturing was carried out using a typical ES cell, 129 line mouse-derived CCE cell (M. R. Kuehn et al., *Nature*, 326, 295 (1987); *Production of Mutation Mice Using ES Cell*).

Example 2

Differentiation of Embryonic Stem Cell into Non-Neuroectodermal Cell

A medium was produced by adding 0.5 nmol/l BMP4 (manufactured by R & D) to the serum-free medium described in Example 1. The ES cell EB5 was cocultured with PA6 cell according to the method described in Example 1, using the thus produced BMP4-added serum-free medium instead of the serum-free medium used in Example 1. Eight days after culturing, immunological cell staining was carried out using the anti-NCAM antibody, the anti-nestin antibody or an antibody against a non-neural ectoderm cell marker E cadherin (manufactured by Takara Shuzo). As a control, coculturing was carried out using the serum-free medium without BMP4. The results are shown in FIGS. 5A, B, C, D, E and F.

Also, 8 days after culturing using the BMP4-added serum-free medium, the medium was changed to Glasgow MEM medium containing 10% fetal bovine serum (manufactured by GIBCO BRL), followed by culturing for 3 days. The thus cultured cells were fixed for 30 minutes by adding 4% p-formaldehyde and immunologically stained using an antibody against a skin epidermis cell marker keratin 14 (manufactured by Biomedia), and the results were compared with those in which culturing was continued for additional 3 days using the bovine serum-free medium, with the results shown in FIGS. 5G, R and I.

Figure 5:
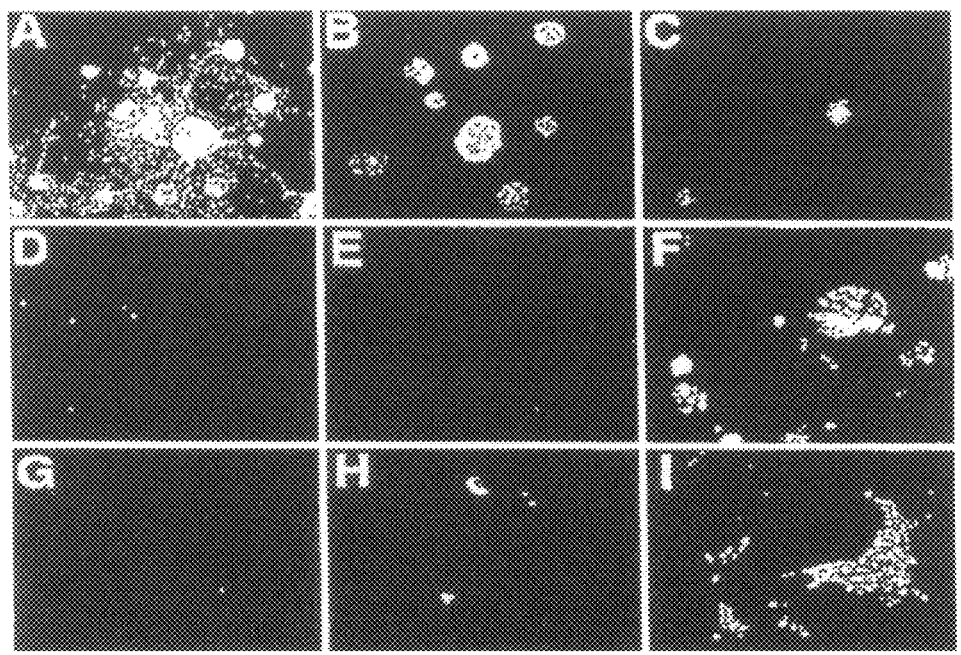
FIG. 5 is a microphotograph showing a result in which colonies formed by coculturing ES cell EB5 with PA6 cell in the absence of BMP4 are stained with (A) an antibody against NCAM, (B) an antibody against nestin, (C) an antibody against E cadherin and (G) an antibody against keratin 14, and a result in which colonies formed by coculturing ES cell with PA6 cell in the presence of BMP4 are stained with (D) an antibody against NCAM, (E) an antibody against nestin, (F) an antibody against E cadherin and (H, I) an antibody against keratin 14.

As shown in Example 1, when the medium without BMP4 was used, the ES cell-derived colonies were strongly anti-NCAM antibody-positive (FIG. 5A) and strongly anti-nestin antibody-positive (FIG. 5B), whereas the number of E cadherin-positive colonies was small (18%) (FIG. 5C). On the other hand, when the BMP4-added serum-free medium was used, the ES cell-derived colonies were anti-NCAM antibody-negative (FIG. 5D) and anti-nestin antibody-negative (FIG. 5E), whereas E cadherin-positive colonies appeared at a high frequency (98%) (FIG. 5F). Keratin 14-positive colonies were not formed when the medium without no BMP4 was used (FIG. 5G), whereas they appeared when the BMP4-added serum-free medium was used at a frequency of 34% (FIG. 5H). When culturing was carried out for 8 days using the BMP4-added serum-free medium and then for next 3 days using the Glasgow MEM medium containing 10% fetal bovine serum, both of the frequency of keratin 14-positive colonies (47%) and the colony size significantly increased (FIG. 5I).

Also, a result similar to the above was obtained when coculturing was carried out using a typical ES cell, 129 line mouse-derived CCE cell (M. R. Kuehn et al., *Nature*, 326, 295 (1987); *Production of Mutation Mice Using ES Cell*).

Example 3

Selection of Stroma Cell Having Activity of Inducing Differentiation of Embryonic Cell into Dopaminergic Neuron ES cell EB5 was cocultured with PA6 cell, MEF cell, STO cell, NIH/3T3 cell, OP9 cell, CHO cell, MDCK cell, 3Y1 cell or COS cell (hereinafter referred to as "respective cells").

The STO cell was cultured according to the method described by Evans et al. (M. J. Evans et al., *Nature*, 292, 154 (1981)). The NIH/3T3 cell was cultured according to the method described by Jainchill et al. (J. L. Jainchill et al., *J. Virol*, 4, 549 (1969)). The OP9 cell was cultured according to the method described by Nakano et al. (T. Nakano et al., *Science*, 272, 722 (1996)). The CHO cell was cultured according to the method described by Puck et al. (T. T. Puck et al., *J. Exp. Med.*, 108, 945 (1985)). The MDCK cell was cultured according to the method described by Misfeldt et al. (D. S. Misfeldt et al., *Proc. Natl. Acad. Sci. USA*, 73, 1212 (1976)). The 3Y1 cell was cultured according to the method described by Sandineyer et al. (S. Sandineyer et al., *Cancer Res.*, 41, 830 (1981)). The COS cell was cultured according to the method described by Gluzman (*Cell*, 23, 175 (1981)).

According to the method described in Example 1, the respective cells and ES cell EB5 were cocultured for 8 days and immunologically stained with the anti-NCAM antibody, and the ratio of positive ES cell-derived colonies was examined. As a result, the PA6 cell, OP9 cell and NIH/3T3 cell showed positive ratios of 95%, 45% and 10%, respectively, so that it was confirmed that these cells have significant nerve differentiation-inducing activity for the ES cell. On the other hand, other cells did not show significant nerve differentiation-inducing activity.

Next, the ES cell were cocultured with the respective cells fixed with p-formaldehyde.

Respective cells whose cell density reached an almost confluent by exchanging the medium in advance was washed twice with PBS(−) and then fixed by adding 4% p-formaldehyde solution and incubating it at 4° C. for 30 minutes. Respective cells were produced by washing the fixed cells several times with PBS(−).

The ES cell EB 5 was cocultured using each of the thus produced respective cells as a feeder cell according to the method described in Example 1. When the cells fixed using p-formaldehyde were used, differentiation of the ES cell into nerve cell was observed at a high ratio by coculturing with the PA6 cell, OP9 cell, NIH/3T3 cell, MEF cell or STO cell but was not observed by coculturing with the 3Y1 cell, COS cell, MDCK cell or CHO cell. It was found from these results that a group of stroma cells, namely PA6 cell, OP9 cell, NIH/3T3 cell, MEF cell and STO cell, have the nerve differentiation-inducing activity, and that this activity remains even when these cells are fixed using p-formaldehyde. Also, it was suggested that a mechanism for inhibiting the nerve differentiation-inducing activity is removed by the p-formaldehyde treatment in the MEF cell and STO cell.

Example 4

Analysis of Activity of Stroma Cell to Differentiate Embryonic Stem Cell into Nerve Cell In order to analyze the activity of stroma cell to differentiate an embryonic stem cell into a nerve cell, an ES cell and a stroma cell were cocultured via a porous filter.

As the porous filter, a 6-well cell culture insert (product No. 3090, manufactured by FALCON) was used. The PA6 cell was cultured in the inner side of the cell culture insert, and the PA6 cell adhered on the filter was produced as a feeder cell according to the method described in Example 1.

The ES cell EB5 suspended in the serum-free medium described in Example 1 was inoculated in 400 cells/well into a gelatin-coated 6-well culture dish (manufactured by FALCON), and the cell culture insert produced using the PA6 cell as a feeder cell was inserted into the wells, followed by culturing. That is, the ES cell EB5 inoculated onto the 6-well culture dish and the PA6 cell produced as a feeder cell inside the cell culture insert were cocultured via the filter membrane. Forth, sixth and seventh days after starting of culturing, the medium was exchanged using a fresh serum-free medium, and the cells were cultured at 37° C. for 8 days in a stream of 5% carbon dioxide in a $CO_2$ incubator. Eight days after of coculturing, the medium was removed and the cells were fixed for 30 minutes by adding 4% p-formaldehyde solution. The thus fixed cells were immunologically stained according to the method described in *Using Antibodies*, Cold Harbor Laboratory Press (1999), using an antibody against a neuron-specific marker tubulin (manufactured by Babco). The formed ratio of tubulin-positive colonies was compared with that in culturing without using the filter, with the results shown in FIG. 6.

Figure 6:
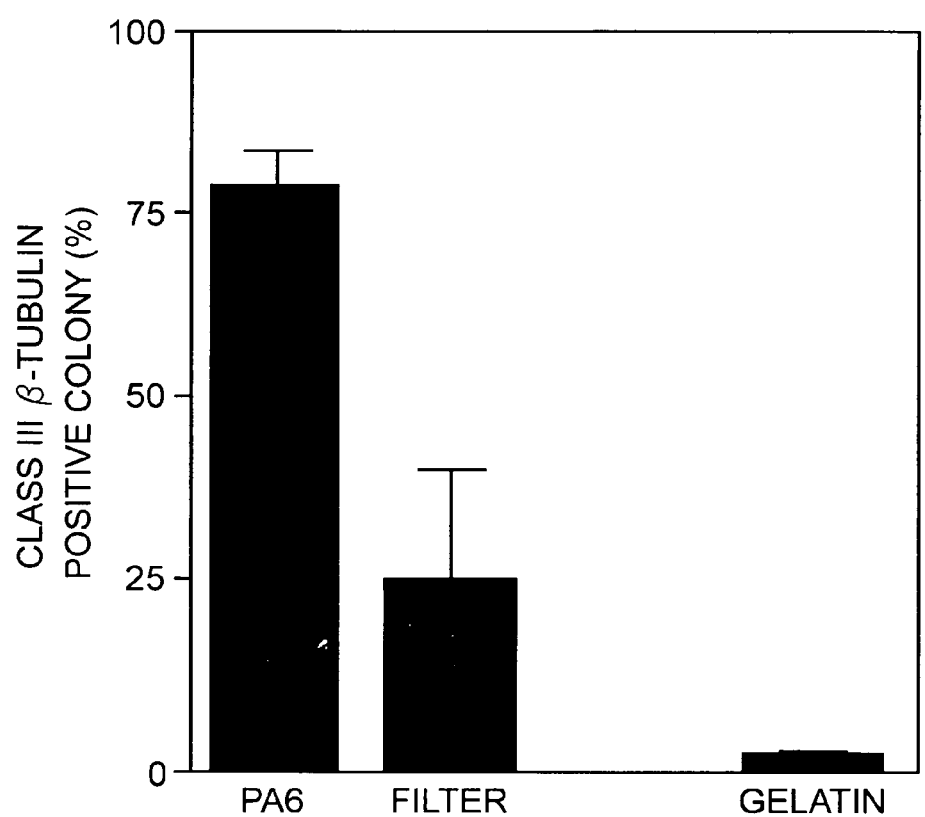
FIG. 6 is a graph showing a result in which colonies formed by coculturing ES cell EB5 with PA6 cell via a filter (filter) or not via a filter (PA6) or colonies formed by culturing ES cell EB5 on gelatin without PA6 cell (gelatin) are stained with an antibody against tubulin.

When the PA6 cell and ES cell EB5 were cocultured via the filter (FIG. 6, Filter), 25% of the colonies were tubulin-positive. Although this proportion was about ⅓ of the efficiency in comparison with that in culturing without using the filter (FIG. 6, PA6), the nerve differentiation was significantly higher than that in culturing on gelatin without PA6 cell (FIG. 6, Gelatin, positive ratio 3% or less).

Example 5

Analysis of Intracerebral Transplantation of Embryonic Stem Cell Differentiated into Dopaminergic Neuron (Part 1)

According to the method described in Example 1, the ES cell EB5 was cultured for 10 days in the serum-free medium without BMP4 using the PA6 cell as a feeder cell. That is, the PA6 cell proliferated to an almost confluent on a 6 cm tissue culture dish was used as a feeder cell, the ES cell EB5 was inoculated onto the feeder cell at a density of 2,000 cells/dish, the medium was exchanged using a fresh serum-free medium on the 4th, 6th and 8th days, and the cells were cultured at 37° C. for 10 days in a stream of 5% carbon dioxide in a $CO_2$ incubator.

The cells differentiation-induced as a result of culturing were fluorescence-labeled using a cell lineage tracer DiI (manufactured by Molecular Probe) according to the manufacture's instructions. After labeling, a papain-treatment was carried out at room temperature for 5 minutes using Papain Dissociation System Kit (manufactured by Worthington) according to the manufacture's instructions, and the formed ES cell-derived colonies were separated from the feeder cell almost as a mass. In this case, in order to avoid damage to nerve cells in the colonies, each colony formed by the differentiation induction was separated from the feeder cell as a mass of colonies as much as possible and used in the transplantation.

After inactivation of the enzyme using the papain inhibitor attached to the kit, a mass of the differentiation-induced ES cells was recovered by centrifugation at 300 rpm for 5 minutes. The mass of the differentiation-induced ES cells recovered from one 6 cm dish was suspended in 5 μl of $N_2$-added Glasgow MEM medium (manufactured by Gibco Lifetech) and used in the following transplantation.

The transplantation and pharmaceutical injection were carried out according to the method described in Current Protocols in Neuroscience (John Wiley & Sons (1999)) 3.10. Each of C57BL/6 mice anesthetized with nembutal was fixed on a stereotaxic apparatus (manufactured by Narishige), and positions of the striate bodies were identified according to the method described in The Mouse Brain in Stereotaxic Coordinates (Academic Press (1997)). In order to destroy the topical dopamine nerve, 6-hydroxydopamine (2,4,5-trihydroxyphenethylamine)hydrobromide (hereinafter referred to as "6-OHDA") was dissolved in PBS at a concentration of 8 mg/ml and, using a micro-glass tube, injected into a position on the mouth side and a position on the tail side of either of the striate bodies, 4 μl of the resulting solution for each of the two positions. Three days thereafter, extrapyramidal signs in the injected side of several of the mice were confirmed and then 2 μl of the suspension of ES cell mass differentiation-induced into nerve cells by the above method was injected into central region of the same side striate body, spending 4 minutes using a blunted 26G Hamilton syringe. Eight days after the 6-OHDA treatment, tissue samples were produced by perfusion-fixing the brain of each mouse and immunologically stained using an antibody against a dopaminergic neuron marker tyrosine hydroxylase (manufactured by Chemicon) and an antibody against dopamine transporter (manufactured by Chemicon).

In the group in which cell transplantation was not carried out by treating with 6-OHDA for destroying the dopamine nerve, nerve tissues expressing the tyrosine hydroxylase and dopamine transporter in the same side striate body were 40% or less of the normal tissues (n=6). On the other hand, in the group in which transplantation of the differentiation-induced ES cell was carried out, the tyrosine hydroxylase- and dopamine transporter-expressing regions in the same side striate body were significantly recovered and became about 75% as a total (n=6), mainly in the DiI-labeled grafts, so that recovery of the dopaminergic neuron by the transplantation was observed.

Example 6

Analysis of Intracerebral Transplantation of Embryonic Stem Cell Differentiated into Dopaminergic Neuron (Part 2)

According to the method described in Example 1, the ES cell EB5 was cultured for 8 days in the serum-free medium without BMP4 using the PA6 cell as a feeder cell. That is, the PA6 cell proliferated to an almost confluent on a 6 cm tissue culture dish was used as a feeder cell, the ES cell EB5 was inoculated onto the feeder cell at a density of 2,000 cells/dish, the medium was exchanged using a fresh serum-free medium on the 4th and 6th days, and the cells were cultured at 37° C. for 8 days in a stream of 5% carbon dioxide in a $CO_2$ incubator.

Culturing was further carried out for 4 days using Glasgow MEM medium to which 2 mmol/l glutamine, 1 mmol/l pyruvic acid, 0.1 mmol/l MEM non-essential amino acids solution, 0.1 mmol/l 2-mercaptoethanol and $N_2$ (manufactured by GIBCO BRL, 1/100 of the 100 times stock solution was added) had been added (hereinafter referred to as "$N_2$-added Glasgow MEM medium").

After culturing, the cells were cultured for 2 hours using a medium (Glasgow MEM medium) containing 10 µg/ml mitomycin C (MMC) according to the method described in *Manipulating the Mouse Embryo, A Laboratory Manual*.

The cells differentiation-induced as a result of culturing were subjected to a papain-treatment at room temperature for 5 minutes using Papain Dissociation System Kit (manufactured by Worthington) according to the manufacture's instructions, and the formed ES cell-derived colonies were separated from the feeder cell almost as a mass (in this case, in order to avoid damage to nerve cells in the colonies, each colony formed by the differentiation induction was separated from the feeder cell as a mass of colonies as much as possible). After separation of the colonies, the colony-forming cells were fluorescence-labeled using a cell lineage tracer DiI (manufactured by Molecular Probe) according to the manufacture's instructions, by allowing the cells to react at room temperature for 20 minutes in a PBS solution containing 5 µg/ml CM-DiI and 4 mg/ml glucose. After labeling, the cells were washed using the $N_2$-added Glasgow MEM medium, made into a suspension of such a density that about $4 \times 10^5$ cells were contained in 1 µl of the $N_2$-added Glasgow MEM medium, and used in the following transplantation.

The transplantation and pharmaceutical injection were carried out according to the method described in *Current Protocols in Neuroscience* (John Wiley & Sons (1999) 3.10. Each of C57BL/6 mice anesthetized with nembutal was fixed on a stereotaxic apparatus (manufactured by Narishige), and positions of the striate bodies were identified according to *The Mouse Brain in Stereotaxic Coordinates* (Academic Press, 1997). In order to destroy the topical dopamine nerve, 6-OHDA was dissolved in PBS at a concentration of 8 µg/µl and, using a micro-glass tube, injected into three positions in either of the striate bodies, 0.5 µl for each of the three positions (A+0.5, L+2.0, v+3.0), (A+1.2, L+2.0, V+3.0) and (A+0.9, L+1.4, V+3.0), according to the method as described in *The Mouse Brain in Stereotaxic Coordinates* (Academic Press, 1997). Three days thereafter, extrapyramidal signs in the injected side of part of the mice were confirmed and then 1 µl of the suspension of ES cell mass differentiation-induced into nerve cell by the above method was injected into central region (A+0.9, L+2.0, V+3.0) of the same side of the striate body, spending a period of 3 minutes by use of a blunted 26G Hamilton syringe. Into a control group, Glasgow MEM medium supplemented with 1 µl of $N_2$ was injected. Fourteen days after the 6-OHDA treatment, the brain of each mouse was perfusion-fixed and immunologically stained using an antibody against a dopaminergic neuron marker tyrosine hydroxylase (manufactured by Chemicon) and an antibody against dopamine transporter (manufactured by Chemicon).

In the group in which cell transplantation was not carried out and treatment with 6-OHDA for destroying the dopamine nerve was carried out, nerve tissues expressing the tyrosine hydroxylase and dopamine transporter in the same side of the striate body were 15% or less of the normal tissues (n=5). On the other hand, in the group in which the cell transplantation was carried out, the tyrosine hydroxylase- and dopamine transporter-expressing regions in the same side of the striate body were significantly recovered and became about 50% as a total (n=5), mainly in the DiI-labeled grafts. Also, formation of teratoma was not observed even 2 weeks after the transplantation.

Example 7

Analysis of Differentiation Process of Embryonic Stem Cell into Nervous Ectodermal Cell According to the method described in Example 1, the ES cell EB5 was cultured for 8 days in the serum-free medium without BMP4 using the PA6 cell as a feeder cell. That is, the PA6 cell proliferated to an almost confluent on a 3 cm tissue culture dish was used as a feeder cell, the ES cell EB5 was inoculated onto the feeder cell at a density of 200 cells/dish, the medium was exchanged using a fresh serum-free medium on the 4th, 6th and 7th days, and the cells were cultured at 37° C. for 8 days in a stream of 5% carbon dioxide in a $CO_2$ incubator.

Eight days after culturing, the cells were fixed according to the method described in Example 1, and colonies formed as a result of coculturing of the ES cell EB5 and PA6 cell were immunologically stained using the anti-NCAM antibody, the anti-class III β tubulin antibody, the anti-nestin antibody, an antibody against a presynapse-specific marker synaptophysin (manufactured by Sigma), an RC2 antibody which recognizes neuroepitheliums (manufactured by Developmental Studies Hybridoma Bank), an MF20 antibody which recognizes mesodermal cells (manufactured by Developmental Studies Hybridoma Bank) and an antibody against PDGF receptor α or Flk1 whose expression are observed in mesodermal cells (S. I. Nishikawa et al., *Development*, 125, 1747 (1998)).

Similar to the results shown in Example 1, most of colonies formed as a result of coculturing of the ES cell EB5 and PA6 cell were stained with the anti-NCAM antibody. Also, as a result of double antibody staining, anti-tubulin antibody-positive colonies were stained with the anti-synaptophysin antibody and nestin-positive colonies were stained with the anti-RC2 antibody. On the other hand, colonies stained with the mesodermal cell markers PDGF receptor α and Flk1 and with various antibodies against MF20 were hardly observed, which were 2% or less of the total colonies. Thus, it was suggested that the induction process of the ES cell into the nerve cell by coculturing with PA6 cell does not substantially accompany induction of mesodermal cells.

Also, a result similar to the above was obtained when coculturing was carried out using a typical ES cell, 129 line mouse-derived CCE cell (M. R. Kuehn et al., *Nature*, 326, 295 (1987); *Production of Mutation Mice Using ES Cell*).

Example 8

Analysis of Differentiation Process of Embryonic Stem Cell into Non-Neuroectodermal Cell A medium was produced by adding 0.5 nmol/l of BMP4 (manufactured by R & D) to the serum-free medium described in Example 1. Using the thus produced BMP4-added serum-free medium instead of the serum-free medium used in Example 1, the ES cell EB5 and PA6 cell were cocultured according to the method described in Example 1. That is, the PA6 cell proliferated to an almost confluent on a 3 cm tissue culture dish was used as a feeder cell, the ES cell was inoculated onto the feeder cell at a density of 200 cells/dish, medium exchange was carried out using fresh medium on the 4th, 6th and 7th days, and the cells were cultured at 37° C. for 8 days in a stream of 5% carbon dioxide in a $CO_2$ incubator.

Eight days after coculturing, the cells were fixed according to the method described in Example 1, and colonies formed as a result of coculturing of the ES cell and PA6 cell were immunologically stained using the anti-NCAM antibody, the anti-E cadherin antibody, an MF20 antibody which recognizes mesodermal cells (manufactured by Developmental Studies Hybridoma Bank) and an antibody against PDGF receptor α or Flk1 whose expression are observed in mesodermal cells (S. I. Nishikawa et al., *Development*, 125, 1747 (1998)).

Similar to the results shown in Example 2, NCAM-negative Ecadherin-positive colonies were formed at a high frequency by coculturing the ES cell and PA6 cell using the BMP4-added serum-free medium. On the other hand, colonies stained with antibodies against the mesodermal cell markers PDGF receptor α, Flk1 and MF20 were hardly observed, which were 5% or less of the total colonies. Thus, it was suggested that the induction process of the ES cell into the non-neural cell by coculturing with PA6 cell in the presence of BMP4 does not substantially accompany induction of mesodermal cells.

Also, a result similar to the above was obtained when coculturing was carried out using a typical ES cell, 129 line mouse-derived CCE cell (M. R. Kuehn et al., *Nature*, 326, 295 (1987); *Production of Mutation Mice Using ES Cell*).

Example 9

Analysis of Nerve Cell Colonies Differentiation-Induced from Embryonic Stem Cell According to the method described in Example 1, the ES cell EB5 was cultured for 8 days in the serum-free medium without BMP4 using the PA6 cell as a feeder cell. That is, the PA6 cell proliferated to an almost confluent on a 3 cm tissue culture dish was used as a feeder, the ES cell was inoculated onto the feeder cell at a density of 200 cells/dish, the medium was exchange using a fresh serum-free medium on the 4th, 6th, 8th and 10th days, and the cells were cultured at 37° C. for 12 days in a stream of 5% carbon dioxide in a $CO_2$ incubator.

Ten days after coculturing, the cells on some of the dishes were fixed according to the method described in Example 1, and the colonies formed as a result of coculturing of the ES cell EB5 with PA6 cell were immunologically stained using antibodies against tyrosine hydroxylase, VachT, GAD and serotonin (n=200).

Among the colonies formed as a result of coculturing of the ES cell EB5 and PA6 cell, 92% were dopaminergic neuron marker tyrosine hydroxylase-positive, 43% were GABAergic neuron marker GAD-positive, 28% were cholinergic neuron marker VachT-positive and 7% were serotonin-positive.

Next, culturing of the remaining dishes was continued and, 12 days after culturing, the cells were fixed according to the method described in Example 1, and the colonies formed as a result of coculturing of the ES cell EB5 with PA6 cell were immunologically stained using antibodies against class III β tubulin, nestin and tyrosine hydroxylase. Also, in order to measure the number of total cells comprising colonies, nuclear staining was carried out using a kit YOYO-1 manufactured by Molecular Probe. After nuclear staining, colonies formed as a result of the coculturing of the ES cell EB5 with PA6 cell (n=20) were randomly selected, and the number of stained cells was counted by observing them under a confocal microscope (n=5,050).

Among the total cells counted, ratios of the class III β tubulin-positive cells, nestin-positive cells and tyrosine hydroxylase-positive cells were 52±9%, 47±10% and 30±4%, respectively.

Also, a result similar to the above was obtained when coculturing was carried out using a typical ES cell, 129 line mouse-derived CCE cell (M. R. Kuehn et al., *Nature*, 326, 295 (1987); *Production of Mutation Mice Using ES Cell*).

Example 10

Analysis of Dopaminergic Neuron Differentiation-Induced from Embryonic Stem Cell (Part 1)

In order to more minutely analyze properties of the nerve cell differentiation-induced from the embryonic stem cell by the method described in Example 1, changes in the expression accompanied by the differentiation induction of Nurr1 (R. H. Zetterstrom et al., *Science*, 276, 248 (1997)) and Ptx3 (M. P. Smidt et al., *Proc. Natl. Acad. Sci. USA*, 94, 13305 (1997)), as markers of dopaminergic neurons in the midbrain, were examined by RT-PCR method.

The cells were prepared as follows.

According to the method described in Example 1, the ES cell EB5 was cultured for 12 days in the serum-free medium without BMP4 using the PA6 cell as a feeder cell. That is, the PA6 cell proliferated to almost confluent on a 9 cm tissue culture dish was used as a feeder, the ES cell EB5 was inoculated onto the feeder cell at a density of $5 \times 10^4$ cells/dish, medium exchange was carried out using fresh serum-free medium on the 4th, 6th, 8th and 10th days, and the cells were cultured at 37° C. for 12 days in a stream of 5% carbon dioxide in a $CO_2$ incubator.

Also, using the ES cell culturing medium shown in Example 1, the ES cell EB5 was inoculated into a 9 cm tissue culture dish at a density of $5 \times 10^4$ cells/dish, medium exchange was carried out using fresh medium on the 4th, 6th, 8th and 10th days, and the cells were cultured at 37° C. for 12 days in a stream of 5% carbon dioxide in a $CO_2$ incubator.

In order to detect expression of Nurr1 and Ptx3 at mRNA level in the thus produced differentiation-induced cell and control ES cell, RT-PCR was carried out using the head of a mouse of 12 days of fetal age as the positive control according to the method reported by Sasai et al. (Y. Sasai et al., *Nature*, 376, 333 (1995)). That is, total RNA was produced from each of the cell-produced dishes and the head of a mouse of 12 days of fetal age, and cDNA was synthesized therefrom using SUPER SCRIPT Preamplification System for First Strand cDNA Synthesis (manufactured by GIBCO BRL). A reaction solution (10 mmol l Tris-HCl (pH 8.3), 50 mmol/l KCl, 1.5 mmol/l $MgCl_2$, 0.2 mmol/l dNTP, 0.2 µmol/l of each gene-specific primer (shown in sequence Listing) and 1 unit of recombinant Ex Taq polymerase (manufactured by Takara Shuzo)) was produced using a solution of the thus synthesized cDNA diluted 50 times with sterile water as a material according to the usual method, and PCR was carried out under conditions in which the reaction was carried out by incubating the reaction solution at 94° C. for 3 minutes, repeating 30 cycles of a cycle of 94° C. for 30 seconds, 55° C. for 30 second and 72° C. for 1 minute and finally incubating it at 72° C. for 7 minutes, and the reaction solution was stored overnight at 4°

C. Semi-quantitative comparison of the expressed amounts of respective factors was carried out by subjecting the reaction solution to an agarose gel electrophoresis and comparing the density of DNA bands specific for the used primers.

In this case, oligonucleotides having the nucleotide sequences represented by SEQ ID NOs: 1 and 2 were used as the Nurr1-specific primers, and oligonucleotides having the nucleotide sequences represented by SEQ ID NOs: 3 and 4 as the Ptx3-specific primers and oligonucleotides having the nucleotide sequences represented by SEQ ID NOs: 5 and 6 were used as the G3PDH-specific primers. When PCR was carried out using the Ptx3-specific primers, DMSO was added to the reaction solution to give a final concentration of 5%.

Figure 7:
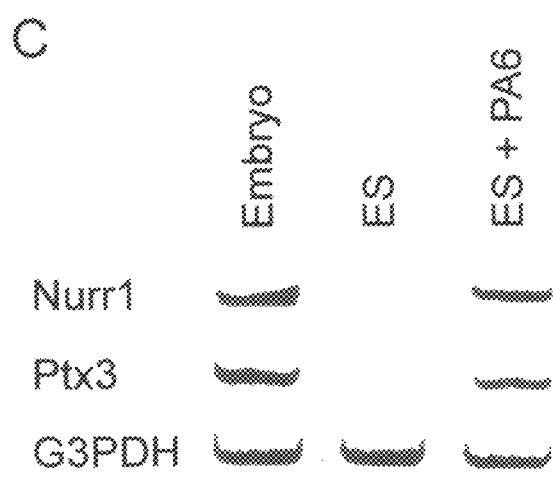
FIG. 7 is a graph showing a result of RT-PCR analysis of the expressed quantity of Nurr1, Ptx3 and G3PDH in differentiated cells formed by coculturing ES cell EB5 with PA6 cell. It shows a result of the analysis by agarose electrophoresis after carrying out RT-PCR using a cell of the head of a mouse of 12 days of fetal age (shown as Embryo in the drawing), ES cell EB5 cocultured with PA6 cell for 12 days (shown as ES+PA6 in the drawing) and a control ES cell EB5 cultured for 12 days (shown as ES in the drawing) as materials.

As a result of the 12 days of coculturing of ES cell with PA6 cell, nerve cell-like colonies were formed similar to the case of the result shown in Example 1. Also, similar to the positive control, significant expression of Nurr1 and Ptx3 was observed in a cell group containing the differentiation-induced colony (FIG. 7: ES+PA6). On the other hand, expression of Nurr1 and Ptx3 was not detected in the control ES cell (FIG. 7: ES). Also, expression of Nurr1 and Ptx3 was not detected when RT-PCR was carried out under the above conditions using the PA6 cell proliferated to an almost confluent on a 9 cm tissue culture dish as a control. Thus, it was found that expression of Nurr1 and Ptx3, as markers of dopaminergic neurons in the midbrain, increases, as embryonic stem cells are differentiation-induced into nerve cells by coculturing with PA6 cell.

Also, a result similar to the above was obtained when coculturing was carried out using a typical ES cell, 129 line mouse-derived CCE cell (M. R. Kuehn et al., *Nature*, 326, 295 (1987); *Production of mutation Mice Using ES Cell*).

Example 11

Analysis of Dopaminergic Neuron Differentiation-Induced from Embryonic Stem Cell (Part 2)

In order to more minutely analyze properties of the nerve cell differentiation-induced from the embryonic stem cell by the method described in Example 1, the produced amount of dopamine was determined using HPLC according to the usual method (K. Inoue, J. G. Kenimer et al., *J. Biol. Chem.*, 263, 8157 (1988); M. Imaizumi and K. Kumakura, *Experimental Medicine Supplement, Nerve Biochemistry Manual*, pp. 191-200 (1990)).

The measuring samples from cells was produced as follows.

According to the method described in Example 1, the ES cell EB5 was cultured for 8 days in the serum-free medium without BMP4 using the PA6 cell as a feeder cell. That is, the PA6 cell proliferated to an almost confluent on a 9 cm tissue culture dish was used as a feeder, the ES cell was inoculated onto the feeder cell at a density of $5 \times 10^4$ cells/dish, the medium was exchanged using a fresh serum-free medium on the 4th and 6th days, and the cells were cultured at 37° C. for 8 days in a stream of 5% carbon dioxide in a $CO_2$ incubator. Thereafter, culturing was further carried out for 6 days using the Glasgow MEM medium to which 2 mmol/l glutamine, 1 mmol/l pyruvic acid, 0.1 mmol/l MEM non-essential amino acids solution, 0.1 mmol/l 2-mercaptoethanol, 0.2 mmol/l ascorbic acid, 0.1 mmol/l tetrahydrobiopterin and $N_2$ had been added. After culturing, the cells were washed twice using a buffer HBSS (manufactured by GIBCO BRL), and the washed cells were cultured for 15 minutes in the HBSS solution containing 56 mmol/l KCl. Fifteen minutes thereafter, the cultured medium was recovered, mixed with 0.4 mol/l perchloric acid and 5 mmol/l EDTA in final concentrations and then preserved at −80° C. as the measuring sample.

Figure 8:
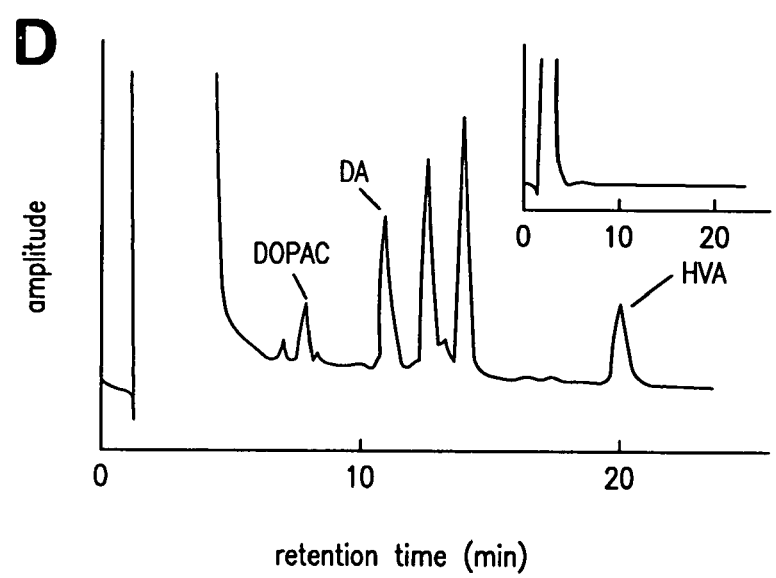
FIG. 8 is a chromatogram showing a result of HPLC analysis of components secreted into the medium caused by the stimulation of differentiated cells formed by coculturing ES cell EB5 with PA6 cell. As a control, a result of the analysis of components secreted by the same stimulation of PA6 cell alone used as a feeder cell is shown in the upper right-side chromatogram.

About one million cells were formed as ES cell-derived differentiated cells by coculturing ES cell with PA6 cell. Also, the amount of dopamine in measuring samples produced using the formed colonies was determined using a reverse phase HPLC-aided Monoamine Analysis System (Eicom Corp., Kyoto, Japan). The results are shown in FIG. 8.

It was found that the nerve cells differentiated from embryonic stem cells by coculturing with PA6 cell released a significant amount of dopamine by stimulation with 56 mmol/l of KCl (7.7 pmol/$10^6$ cells (ES cell-derived differentiated cells)). Dopamine derivatives DOPAC (3,4-dihydroxyphenylacetic acid) and HVA (homovanillic acid) were also detected in significant amounts (2.5 pmol/$10^6$ cells (ES cell-derived differentiated cells) and 4.0 pmol/$10^6$ cells (ES cell-derived differentiated cells), respectively).

Thus, it was also shown in vitro that the dopaminergic neuron differentiation-induced from embryonic stem cells by coculturing with PA6 cell has ability of functioning as a functional nerve by producing dopamine.

Example 12

Differentiation of Primitive Ectoderm-Constituting Cell into Dopaminergic Neuron A cell isolated from a primitive ectoderm (pre-streak epiblast) of a mouse of 6 days of fetal age was used instead of the ES cell EB5, and cocultured with PA6 cell according to the method described in Example 1 or 2.

Cells constituting the pre-streak epiblast of a mouse of 6 days of fetal age were isolated and cultured according to the method described in *Manipulating the Mouse Embryo, A Laboratory Manual*.

According to the method described in Example 1, the isolated embryonic cell was cultured for 8 days in the serum-free tedium without BMP4 using the PA6 cell as a feeder cell. That is, the PA6 cell proliferated to an almost confluent on a 3 cm tissue culture dish was used as a feeder cell, the isolated pre-streak epiblast cell was inoculated onto the feeder cell at a density of 200 cells/dish, the medium was exchanged using a fresh serum-free medium on the 4th, 6th and 7th days, and the cells were cultured at 37° C. for 8 days in a stream of 5% carbon dioxide in a $CO_2$ incubator.

Also, the isolated embryonic cell was cocultured with PA6 cell according to the method described in Example 1, using a medium produced by supplementing the serum-free medium used in Example 1 with 0.5 nmol/l BMP4 (manufactured by R & D). That is, the PA6 cell proliferated to an almost confluent on a 3 cm tissue culture dish was used as a feeder cell, the ES cell was inoculated onto the feeder cell at a density of 200 cells/dish, the medium was exchanged using a fresh medium on the 4th, 6th and 7th days, and the cells were cultured at 37° C. for 8 days in a stream of 5% carbon dioxide in a $CO_2$ incubator.

Eight days after coculturing, the cells were fixed according to the method described in Example 1, and the colonies formed as a result of coculturing of the isolated embryonic cell with PA6 cell were immunologically stained using the anti-NCAM antibody, anti-tubulin antibody, anti-nestin antibody and anti-E cadherin antiblody.

A result similar to Examples 1 and 2 carried out using the ES cell EB5 was obtained also in the use of the embryonic cell of the isolated pre-streak epiblast, and appearance of a nervous system cell and an epidermal system cell was observed.

Example 13

Recovery of Factor, in Stroma Cell, Capable of Inducing Differentiation of Embryonic Stem Cell into Ectodermal Cell According to the method described in Example 3, the ES cell EB5 was cultured for 8 days in the serum-free medium without BMP4 using the p-formaldehyde-fixed PA6 cell as a feeder cell. Also, the case when the PA6 cell was cultured in a medium containing heparin (GIBCO BRL) (hereinafter referred to as "heparin treatment") was compared with the case when culturing in a heparin-free medium. That is, dishes in which the PA6 cell proliferated to an almost confluent on a 3 cm tissue culture dish was cultured for 2 days using a medium containing 200 ng/ml of heparin and dishes in which it was cultured for 2 days using a heparin-free medium were produced, washed twice with PBS(−) and subjected to p-formaldehyde fixation, and the ES cell EB5 was inoculated onto the p-formaldehyde-fixed PA6 cell at a density of 200 cells/dish, the medium was exchanged using a fresh medium on the 4th, 6th and 7th days, and then the cells were cultured at 37° C. for 8 days in a stream of 5% carbon dioxide in a $CO_2$ incubator.

Eight days after coculturing, the cells were fixed according to the method described in Example 1, and the colonies formed as a result of the coculturing of the ES cell EB5 with PA6 cell were immunologically stained using the anti-NCAM antibody, anti-tubulin antibody and anti-nestin antibody.

When the PA6 cell having no heparin treatment was used as a feeder cell, close to 90% of the ES cell-derived colonies were NCAM-positive similar to the results shown in Example 3, so that differentiation of ES cell into nerve cell was observed at a high frequency. On the other hand, significant differentiation of ES cell into nerve cell was not observed when the heparin-treated PA6 cell was used as a feeder cell. Accordingly, it was suggested that the activity of a stroma cell to induce differentiation of an embryonic stem cell into an ectodermal cell can be recovered from a culture supernatant by culturing the stroma cell using a heparin-containing medium, similar to the phenomenon observed by Wnts molecule (R. S. Bradley & A. M. C. Brown, *EMBO J.*, 9, 1569 (1990)).

Example 14

Differentiation Induction of Embryonic Stem Cell into Various Neural Cells along the Dorso-Ventral Axis In order to examine effects of shh and BMP4 as factors which determine diversity of nerves along the dorso-ventral axis in the generation of central nervous system, these factors were allowed to act upon an ES cell which started its differentiation on a stroma cell and their influences were examined in the following manner.

According to the method described in Example 1, the ES cell EB5 was cultured for 10 days in the serum-free medium without BMP4 using the PA6 cell as a feeder cell. That is, the PA6 cell proliferated to almost confluent on a 3 cm tissue culture dish was used as a feeder cell, the ES cell was inoculated onto the feeder cell at a density of 200 cells/dish, the medium was exchanged using a fresh serum-free medium on the 4th, 6th and 8th days, and the cells were cultured at 37° C. for 10 days in a 5% $CO_2$ incubator.

Effects of shh were evaluated using a serum-free medium to which 300 nmol/l of shh (manufactured by R & D) had been added at the time of the medium exchange on the 4th, 6th and 8th days.

Effects of BMP4 were evaluated using a serum-free medium to which 0.5 nmol/l of BMP4 (manufactured by R & D) had been added at the time of the medium exchange on the 4th, 6th and 8th days.

Ten days after of coculturing, the cells cultured by respective culturing methods were fixed according to the method described in Example 1, and the colonies formed as a result of coculturing of the ES cell with PA6 cell were immunologically stained using the anti-NCAM antibody, an antibody against HNF-3β which is a marker of the basal plate existing on the most ventral side of the central nervous system primordium (neural tube) (purchased from Developmental Studies Hybridoma Bank), an antibody against Nkx2.2 as a marker existing secondary to the HNF-3β from the ventral side (purchased from Developmental Studies Hybridoma Bank), an antibody against Pax-7 as a marker of the neural tube dorsal side (purchased from Developmental Studies Hybridoma Bank), an antibody against AP-2 as a marker of the neural crest cell (purchased from Developmental Studies Hybridoma Bank), an antibody against islet 1 as a marker of motor neuron (purchased from Developmental Studies Hybridoma Bank) and an antibody against VAchT which is a marker of cholinergic neuron (manufactured by Chemicon).

Regardless of the addition of shh or BMP4, most of the colonies formed as a result of coculturing of the ES cell EB5 with PA6 cell were stained with the anti-NCAM antibody similar to the results shown in Example 1, and 90% of the ES cell-derived colonies were positive in both cases.

The result is shown in Table 1, together with the ratio of ES cell-derived colonies stained with antibodies against other markers.

TABLE 1

| Antibodies | Control | shh added | BMP4 added |
|---|---|---|---|
| Anti-NCAM antibody | 90% | 90% | 90% |
| Anti-HNF-3β antibody | 70% | 81% | 9% |
| Anti-Nkx2.2 antibody | 44% | 85% | 19% |
| Anti-Pax-7 antibody | 30% | 0% | 72% |
| Anti-AP-2 antibody | 16% | 0% | 24% |
| Anti-islet 1 antibody | 82% | 82% | 36% |
| Anti-VAchT antibody | 36% | 58% | 42% |

It was shown from the above results that nervous system cells expressing not only the NCAM as a neuron marker but also various types of neuron-specific markers are formed by the nerve cell induction of the ES cell by its coculturing with the PA6 cell. That is, when the ES cell was differentiation-induced by coculturing with the PA6 cell, it is differentiation-induced into a nervous system cell which is positioned on the basal plate of the most ventral side of the central nervous system primordium (neural tube) and expresses HNF-3β, a nervous system cell which is positioned secondary to the HNF-3β from the ventral side of the central nervous system primordium (neural tube) and expresses Nkx2.2, a nerve cell of the neural tube dorsal side expressing Pax-7, a neural crest cell expressing AP-2 and a motor neuron expressing islet 1.

Also, since shh and BMP4, whose relation to the determination of dorso-ventral axis during the embryo neurogenesis has been revealed, showed a differentiation potency similar to the in vivo differentiation potency of embryonic neural precursor cell, a cell of neural tube before the step of determining dorso-ventral axis is induced by coculturing ES cell with the PA6 cell. That is, in this neural tube cell, expression induction of the ventral side markers HNF-3β and Nkx2.2 and expression inhibition of the dorsal side markers Pax-7 and AP-2 are observed by the action of shh as a neural tube dorso-ventral factor. On the other hand, when the BMP4 as a neural tube dorsal side factor is allowed to act, expression inhibition of the ventral side markers HNF-3β and Nkx2.2 and expression induction of the dorsal side markers Pax-7 and AP-2 are observed.

Also, a result similar to the above was obtained when a typical ES cell, 129 line mouse-derived CCE cell (M. R. Kuehn et al., *Nature*, 326, 295 (1987); *Production of Mutation Mice Using ES Cell*), was used.

Example 15

Production of Monoclonal Antibody Capable of Recognizing Stroma Cell PA6

(1) Production of Immunogen

The PA6 cell was used as the antigen. The PA6 cell was cultured according to the method described in Example 1. The PA6 cell whose cell density reached an almost confluent was washed twice with PBS(−), a PBS(−) solution containing 10 μg/ml of actinase (manufactured by Kaken Pharmaceutical) and 0.02% of EDTA was added thereto, followed by culturing at 37° C. for 30 minutes, the action of actinase was stopped by adding α-MEM medium containing 10% fetal bovine serum (GIBCO-BRL), and then the cells were recovered by 5 minutes of centrifugation at 4° C. and at 1,000×g. The thus recovered cells were re-suspended in PBS(−) and washed by centrifugation at 4° C. and at 1,000×g for 5 minutes. A total of $10^7$ of the cells washed twice with PBS(−) were suspended in 1 ml of PBS(−) and used as the antigen.

(2) Immunization of Animal and Production of Antibody Producing Cell

The $10^7$ cells produced in (1) were administered to each of 3 female SD rats of 6 to 8 weeks of age, together with 2 mg of an aluminum hydroxide adjuvant (*Antibody, A Laboratory Manual*, p. 99) and $1\times10^9$ cells of pertussis vaccine (manufactured by Chiba Serum Institute). Two weeks after the administration, the $10^7$ cells produced in (1) were administered once a week for a total of 4 times. Blood samples were collected from the carotid artery of the rats, their serum antibody titers were examined by an enzyme immunoassay shown in the following, and the spleen was excised 3 days after the final immunization from a mouse which showed a sufficient antibody titer.

The thus excised spleen was cut to pieces in MEM (minimum essential medium) (manufactured by Nissui Pharmaceutical), the cells were unbound using a pair of forceps and centrifuged (250×g, 5 minutes). The thus obtained precipitation fraction was treated with Tris-ammonium chloride buffer (pH 7.65) for 1 to 2 minutes to eliminate erythrocytes. The thus obtained precipitation fraction (cell fraction) was washed three times with MEM and used in cell fusion.

(3) Enzyme Immunoassay (Binding ELISA)

The PA6 cell was inoculated into each well of a 96 well EIA plates (manufactured by Greiner), and a plate in which the cells were proliferated into a confluent was used as an antigen plate. An immunized rat antiserum or a monoclonal antibody culture supernatant was dispensed in 50 μl/well into the plate and incubated at 37° C. for 1 hour. One hour after standing, the added antiserum or culture supernatant was discarded, and PBS(−) containing 0.25% glutaraldehyde was added to the remaining cells and incubated at room temperature for 30 minutes. The plate was washed with 0.05% polyoxyethylene (20) sorbitan monolaurate (equivalent to Tween 20, trademark of ICI: manufactured by Wako Pure Chemical Industries)/PBS (hereinafter referred to as "Tween-PBS"), and a peroxidase-labeled rabbit anti-rat inmunoglobulin (manufactured by DAKO) was dispensed in 50 μl/well into the plate and incubated at room temperature for 1 hour. After washing the plate with Tween-PBS, an ABTS substrate solution (2,2-azinobis(3-ethylbenzothiazole-6-sulfonic acid) ammonium salt, 1 mmol/l ABTS/0.1 mol/l citrate buffer (pH 4.2)) was added thereto, and the absorbance at 415 nm was measured using a plate reader (Emax; manufactured by Molecular Devices).

(4) Production of Mouse Myeloma Cells

An 8-azaguanine-resistant mouse myeloma cell line P3X63Ag8U.1 (P3-U1: purchased from ATCC) was cultured in a normal medium (RPMI medium supplemented with 10% fetal calf serum), and $2\times10^7$ or more of the cells are secured for cell fusion and used as the parent cell line in the cell fusion.

(5) Production of Hybridoma

The mouse spleen cells obtained in Example 15(2) and the myeloma cells obtained in Example 15(4) were mixed in a proportion of 10:1, followed by centrifugation (250×g, 5 minutes). The cells of the thus obtained precipitation fraction were thoroughly disintegrated, a mixed solution of 2 g of polyethylene glycol-1,000 (PEG-1,000), 2 ml of MEM and 0.7 ml of dimethyl sulfoxide was added to the cells with stirring at 37° C., in an amount of 0.5 ml per $10^8$ mouse spleen cells, 1 ml of MEM was added several times at 1 to 2-minute intervals and then the total volume was adjusted to 50 ml by adding MEM.

After centrifugation of the suspension (900 rpm, 5 minutes), the cells of the thus obtained precipitation fraction were loosened gently and then suspended in 100 ml of HAT medium (produced by adding HAT media Supplement (manufactured by Boehringer Mannheim) to the RPMI medium supplemented with 10% fetal calf serum) by repeated drawing up into and discharging from a measuring pipette. This suspension was dispensed in 200 μl/well into a 96-well culture plates, followed by culturing at 37° C. for 7 to 14 days in a 5% $CO_2$ incubator.

After culturing, the culture supernatant was examined by the enzyme immunoassay described in Example 15(3) to select wells which reacted with the PA6 cell but did not react with a control plate coated with 1% BSA-containing PBS(−) (hereinafter referred to as "1% BSA-PBS(−)"), and cloning was repeated twice by limiting dilution to establish anti-PA6 monoclonal antibody producing hybridomas from cells contained therein, As a result, three types of anti-human PA6 cell antibodies KM1306, KM1307 and KM1310 were obtained by using the PA6 cell as the antigen.

The KM1310 producing hybridoma cell line has been deposited on Apr. 27, 2001, as FERM BP-7573 in International Patent organism Depositary, National Instituted of Advanced Industrial Science and Technology (AIST Tsukuba Central 6, 1-1, Higashi 1-Chome, Tsukuba-shi, Ibaraki-ken, 305-8566, Japan).

(6) Production of Monoclonal Antibody

Each of the hybridoma cell lines obtained in Example 15(5) was intraperitoneally injected into pristane-treated 8 weeks old female mice (BALB/c) at a dose of $5\times10^6$ to $20\times10^6$ cells per animal. Ten to twenty-one days thereafter, the ascitic fluid was collected from the ascites tumor mice caused by the hybridoma (1 to 8 ml/animal).

The ascitic fluid was centrifuged (1,200×g, 5 minutes) to remove solid matters Purified IgM monoclonal antibodies were obtained by purifying them using an ammonium sulfate precipitation method (*Antibody, A Laboratory Manual*). The subclass of all of the monoclonal antibodies KM1306, KM1307 and KM1310 was determined to be IgM by ELISA using a subclass typing kit.

(7) Analysis of the Reactivity with PA6 Cell by Fluorescent Antibody Technique (Cell Sorter Analysis)

The PA6 cell was cultured according to the method described in Example 1. The PA6 cell whose cell density reached an almost confluent was washed twice with PBS(−), a PBS(−) solution containing 10 μg/ml of actinase (manufactured by Kaken Pharmaceutical) and 0.02% of EDTA was added thereto, followed by culturing at 37° C. for 30 minutes, the action of actinase was stopped by adding α-MEM medium containing 10% fetal bovine serum (GIBCO-BRL), and then the cells were recovered by centrifugation at 4° C. and at 1,000×g for 5 minutes. The thus recovered cells were re-suspended in A-MEM medium containing 10% fetal bovine serum (GIBCO-BRL) and dispensed in 1×10$^6$ cell portions into 1.5 ml tubes. The dispensed cells were washed twice by suspending them in 1% BSA-PBS(−) and centrifuging at 1,000×g for 5 minutes. The washed cells were suspended in 1% BSA-PBS(−) solution containing 10 μg/ml of a purified antibody (or 50 μg/ml of an ammonium sulfate precipitation antibody fraction) and cultured at 37° C. for 30 minutes to carry out the reaction with the antibody. The cells reacted with the antibody were allowed to react with a fluorescence-labeled secondary antibody in the usual way and analyzed using a cell sorter (*Antibody, A Laboratory Manual*). That is, the cells reacted with the antibody were recovered by centrifugation at 1,000×g for 5 minutes, suspended in 1% BSA-PBS(−) solution containing the secondary antibody, cultured at 37° C. for 30 minutes, washed twice with 1% BSA-PBS(−), suspended in 2 ml of 1% BSA-PBS(−) solution and analyzed using a cell analyzer (EPICS XL system II, manufactured by Coulter). As the secondary antibody, an FITC-labeled anti-rat immunoglobulin antibody (FITC-labeled goat anti-rat immunoglobulin (H+L); manufactured by CALTAG) was diluted 30 times with 1% BSA-PBS(−), and the solution was used in 100 μl/tube portions. As a control antibody, KM2070 as a monoclonal rat IgM antibody which recognizes a Klotho protein was allowed to react at a concentration of 10 μg/ml and detected in the same manner. Also, KM2070 is an antibody produced by a hybridoma KM2070 (FERM BP-6196; WO 98/29544). Also, KM2070 was used as the control antibody after confirming in advance that expression of the antigen molecule recognized by KM2070 is not due to the PA6 cell.

Figure 9:
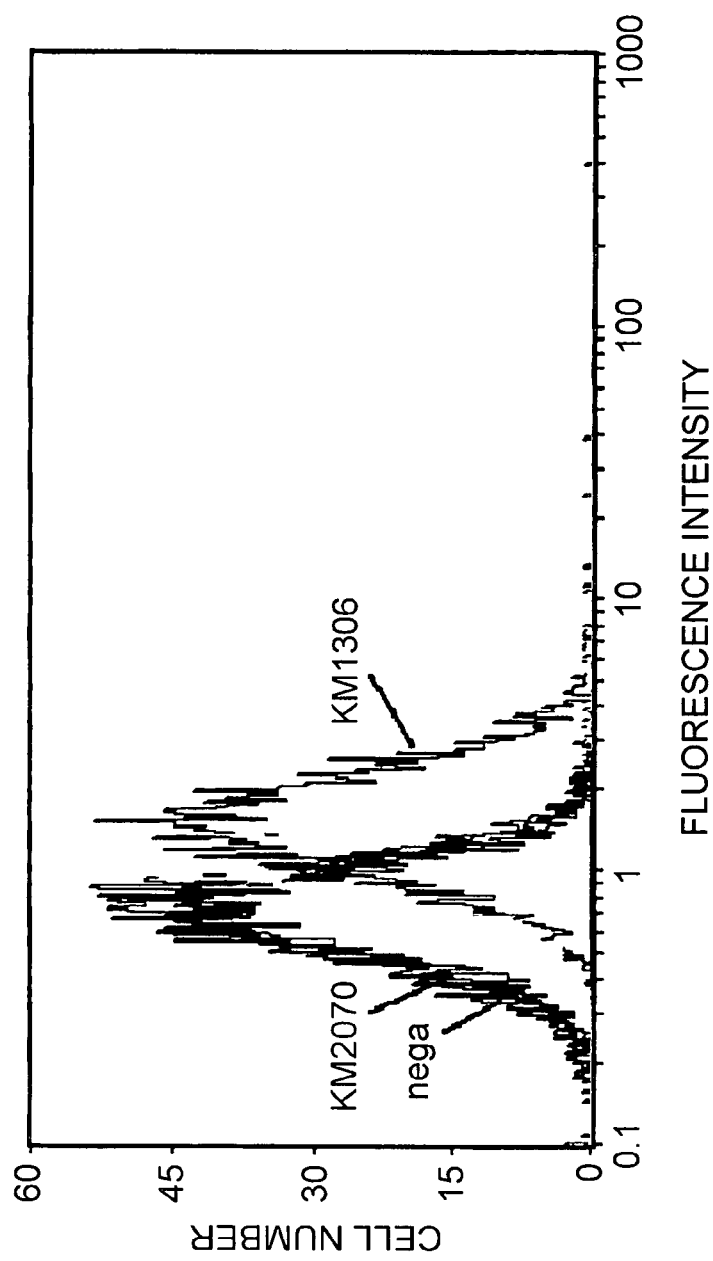
FIG. 9 is a graph showing a result on the reactivity of a monoclonal antibody KM1306 with PA6, analyzed by fluorescent antibody technique using a cell sorter. As a control, a result of the same analysis carried out using a rat IgM monoclonal antibody KM2070 whose species and subclass coincided with the antibody is shown. The number of cells is shown as the ordinate, and the fluorescence strength is shown as the abscissa.
Figure 10:
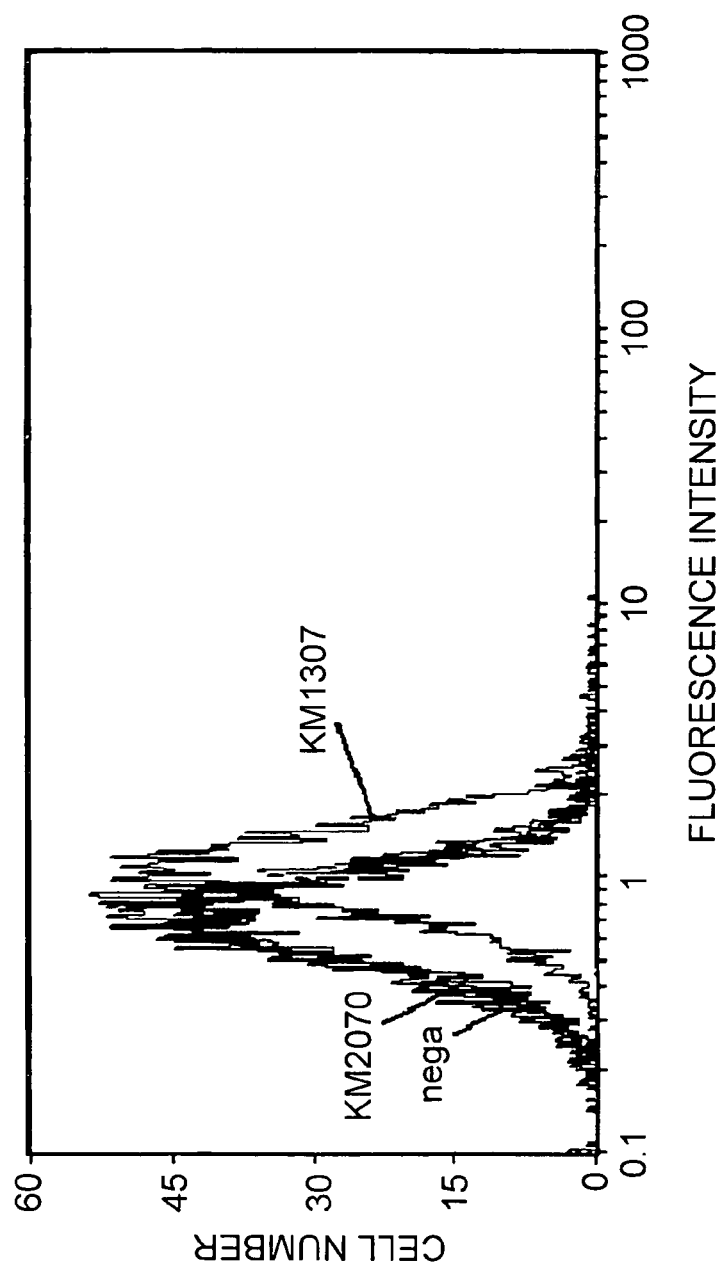
FIG. 10 is a graph showing a result on the reactivity of a monoclonal antibody KM1307 with PA6, analyzed by fluorescent antibody technique using a cell sorter. As a control, a result of the same analysis carried out using a rat IgM monoclonal antibody KM2070 whose species and subclass coincided with the antibody is shown. The number of cells is shown as the ordinate and the fluorescence strength is shown as the abscissa.
Figure 11:
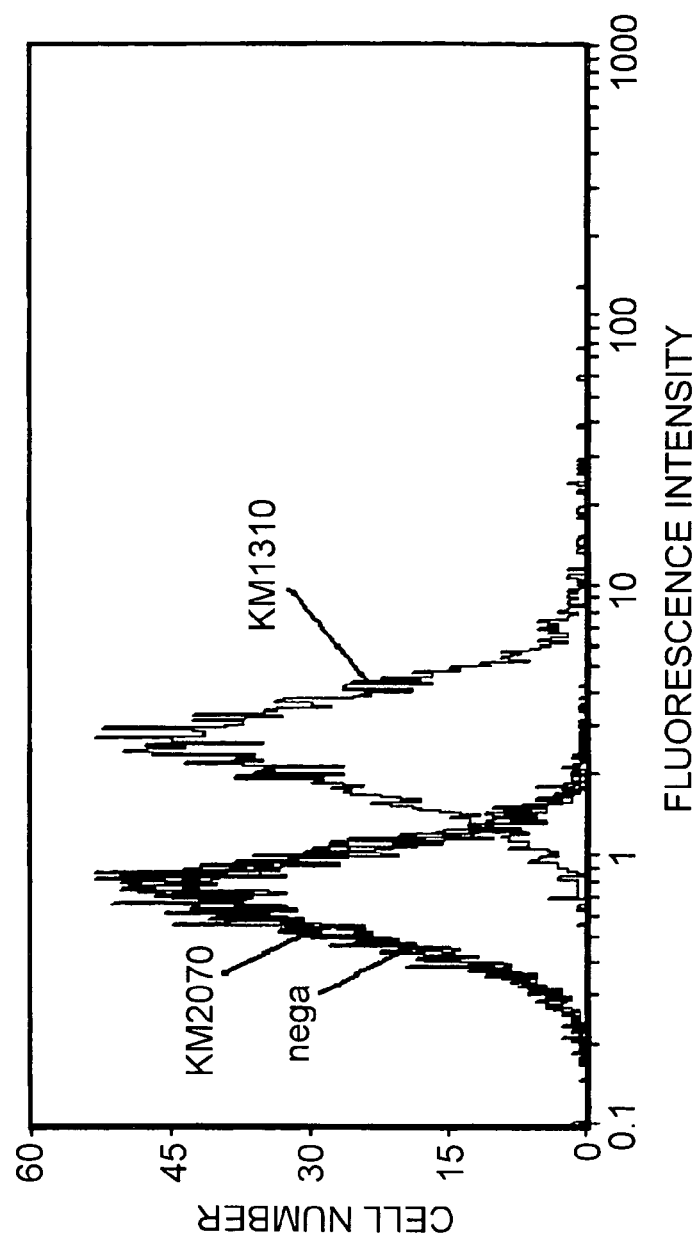
FIG. 11 is a graph showing a result on the reactivity of a monoclonal antibody KM1310 with PA6, analyzed by fluorescent antibody technique using a cell sorter. As a control, a result of the same analysis carried out using a rat IgM monoclonal antibody KM2070 whose species and subclass coincided with the antibody is shown. The number of cells is shown as the ordinate and the fluorescence strength is shown as the abscissa.

As respectively shown in FIGS. 9, 10 and 11, KM1306, KM1307 and KM1310 obtained by immunizing the PA6 cell recognized the PA6 cell. The ordinate shows the number of cells, and the abscissa shows fluorescence intensity. In these drawings, "nega" indicates a result when the antibody was not added.

While the invention has been described in detail and with reference to specific embodiments thereof, it will be apparent to one skill in the art that various changes and modifications can be made therein without departing from the spirit and scope thereof.

What is claimed is:

1. A method for producing a cell expressing a neural crest marker or a neural tube marker, comprising:
    culturing under serum-free conditions a mammalian embryonic stem cell in vitro in the absence of retinoic acid and in the presence of a stroma cell without forming embryoid body, wherein the stroma cell is OP9 cell or PA6 cell.

2. A method for producing a dopaminergic neuron, an acetylcholinergic neuron, a γ-aminobutyratergic neuron or a serotonergic neuron, comprising:
    culturing under serum-free conditions a mammalian embryonic stem cell in vitro in the absence of retinoic acid and in the presence of a stroma cell without forming embryoid body, wherein the stroma cell is OP9 cell or PA6 cell.

3. A method for producing a neural stem cell which is stained by an anti-nestin antibody comprising:
    culturing under serum-free conditions a mammalian embryonic stem cell in vitro in the absence of retinoic acid and in the presence of a stroma cell without forming embryoid body, wherein the stroma cell is OP9 cell or PA6 cell.

4. The method according to any one of claim 1, 2 or 3, wherein the stroma cell is a stroma cell whose proliferation potency is deleted by a physicochemical treatment.

5. The method according to any one of claim 1, 2 or 3, wherein the stroma cell is a stroma cell whose proliferative potency is deleted by an antitumor agent, irradiation or pathologic tissue fixative.

6. The method according to claim 4, wherein the physicochemical treatment is an antitumor agent selected from the group consisting of mitomycin C, 5-fluorouracil, adriamycin and methotrexate.

7. The method according to any one of claim 1, 2 or 3, wherein the stroma cell is a stroma cell whose proliferative potency is deleted by a microwave fixation, a rapid freeze-substitution fixation, a glutaraldehyde fixation, a p-formaldehyde fixation, a formalin fixation, an acetone fixation, a Van fixation, a periodic acid fixation, a methanol fixation or an osmic acid fixation.

8. The method according to any one of claim 1, 2 or 3, wherein the stroma cell is an M-CSF deficient mouse calvaria-derived OP9 cell.

9. The method according to claim 8, wherein the stroma cell is recognized by a monoclonal antibody produced by hybridoma FERM BP-7573.

10. The production method according to claim 1, wherein the method produces a cell expressing said neural crest marker.

11. The production method according to claim 1, wherein the method produces a cell expressing said neural tube marker.

12. The production method according to claim 2, wherein the method produces said dopaminergic neuron.

13. The production method according to claim 2, wherein the method produces said acetylcholinergic neuron.

14. The production method according to claim 2, wherein the method produces said γ-aminobutyratergic neuron.

15. The production method according to claim 2, wherein the method produces said serotonergic neuron.

16. The method according to any one of claims 1, 2 or 3, wherein the stroma cell is a mouse calvaria-derived MC3T3-G2/PA6 cell.

17. The method according to claim 8, wherein the stroma cell is recognized by a monoclonal antibody produced by hybridoma FERM BP-7573.

18. The method according to claim 16, wherein the stroma cell is recognized by a monoclonal antibody produced by hybridoma FERM BP-7573.

* * * * *

UNITED STATES PATENT AND TRADEMARK OFFICE
CERTIFICATE OF CORRECTION

PATENT NO. : 8,273,570 B2
APPLICATION NO. : 09/855587
DATED : September 25, 2012
INVENTOR(S) : Yoshiki Sasai et al.

Page 1 of 7

It is certified that error appears in the above-identified patent and that said Letters Patent is hereby corrected as shown below:

ON THE TITLE PAGE [56] REFERENCES CITED:

Other Publications,
"Hirami, et al., "Generation of retinal cells from mouse and human induced pluripotent stems sells", Neuroscience Letters, vol. 458 (2000) 126-31. Kim, et al.," should read --¶ Kim, et al.,--;
"Mizuseki et al., (PNAS, 100(10); 5828-5833, 2003,*" should be deleted; and
Insert:
--Fuchs, et al., "Stem Cells: A New Lease on Life", Cell, Vol. 100 (2000), 143-155.
Kawasaki, et al., "Generation of dopaminergic neurons and pigmented epithelia from primate ES cells by stromal cell-derived inducing activity", PNAS, Vol. 99, No. 3 (2002) 1580-85.
Schuldiner et al., "Effects of eight growth factors on the differentiation of cells derived from human embryonic stem cells", PNAS, Vol. 97, No. 1 (2000) 11307-312.
Wilson et al., "Induction of epidermis and inhibition of neural fate by Bmp-4", Nature, Vol. 376 (1995) 331-33.
Kodama, et al., "MC3T3-G2/PA6 preadipoctyes support in vitro proliferation of hemopoietic stem cells through a mechanism different than that of interleukin 3", Journel Cell Physio., Vol. 129 (1986) 20-26.
Kawasaki, et al, "Induction of midbrain dopaminergic neurons from ES cells by stromal cell-derived inducing activity", Neuron, Vol. 28 (2000) 31-40.
Toru Nakano, "In vitro development of hematopoietic system from mouse embryonic stem cells: a new approach for embryonic hematopoiesis", Int. J. Hematology, Vol. 65 (1996) 1-8.
Komatsu, et al., "Embryonic Stem (ES) Cell in Vitro", Sapporo Med. Journal, Vol. 67 (1998) 11-22.--.

Signed and Sealed this
Twelfth Day of February, 2013

Teresa Stanek Rea
*Acting Director of the United States Patent and Trademark Office*

COLUMN 1:

Line 24, "a cell which" should read --a cell of another individual which--;
Line 25, ", of other indi-" should be deleted;
Line 26, "vidual" should be deleted;
Line 32, "mouse" should read --mouse- --; and
Line 41, "at" should read --from--.

COLUMN 2:

Line 6, "It" should read --it--;
Line 36, "as" should be deleted; and
Line 39, "other" should read --another--.

COLUMN 3:

Line 30, "It" should read --it--; and
Line 45, "(M.J. Evans et al," should read --(M.J. Evans et al.,--.

COLUMN 5:

Line 5, "show" should read --shows--; and
Line 22, "control," should read --control;--.

COLUMN 6:

Line 57, "confluent" should read --confluence--.

COLUMN 7:

Line 48, "an" should read --a--; and
Line 53, "Protein," should be italicized.

COLUMN 8:

Line 10, "Parkinson" should read --Parkinson's--;
Line 20, "Parkinson" should read --Parkinson's--;
Line 25, "Parkinson" should read --Parkinson's--;
Line 32, "Parkinson" should read --Parkinson's--; and
Line 40, "these backgrounds," should read --this background,--.

COLUMN 10:

Line 30, "an" should read --a--.

COLUMN 13:

Line 45, "Alzheimer" should read --Alzheimer's-- and "Huntington" should read --Huntington's--; and
Line 46, "Parkinson" should read --Parkinson's--.

COLUMN 15:

Line 15, "include" should read --includes--; and
Line 44, "include" should read --includes--.

COLUMN 19:

Line 66, "an" should be deleted; and
Line 67, "almost confluent" should read --near confluency--.

COLUMN 20:

Line 24, "KNOCKOUTS" should read --KNOCKOUT™--.

COLUMN 23:

Line 52, "available" should read --available for--.

COLUMN 24:

Lines 5-6, "Guide to Techniques in Mouse Development" should be italicized; and
Line 13, "medium," should read --media,--.

COLUMN 27:

Line 32, "confluent" should read --confluence--;
Line 39, "confluent" should read --confluence--; and
Line 55, "confluent" should read --confluence--.

COLUMN 28:

Line 15, "confluent" should read --confluence--;
Line 48, "confluent" should read --confluence--; and
Line 53, "with" should read --with PBS.--.

COLUMN 30:

Line 20, "differentiationinduced" should read --differentiation-induced--.

COLUMN 31:

Line 8, "cause" should read --caused--;
    Line 12, "Alzheimer" should read --Alzheimer's-- and "Huntington" should
        read --Huntington's--; and
    Line 13, "Parkinson" should read --Parkinson's--.

COLUMN 33:

Line 58, "10:1," should read --10:1;--.

COLUMN 34:

Line 11, "plates" should read --plate--.

COLUMN 35:

Line 43, "includes" should read --include--; and
    Line 48, "(1991)))" should read --(1991))--.

COLUMN 37:

Line 17, "Saccharomyces" should be italicized;
    Lines 17-18, "Schizosaccharomyces," should be italicized;
    Line 18, "Kluyveromyces," and "Trichosporon," should be italicized; and
    Line 19, "Schwanniomyces" should be italicized.

COLUMN 44:

Line 24, "Parkinson" should read --Parkinson's--; and
    Line 45, "western" should read --Western--.

COLUMN 45:

Line 58, "confluent" should read --confluence--; and
    Line 64, "KNOCKOUT SR" should read --KNOCKOUT™ SR--.

COLUMN 47:

Line 63, "R and I." should read --H and I.--.

COLUMN 48:

Line 55, "were" should read --was--; and
    Line 58, "fluent" should read --fluence-- and "was" should read --were--.

COLUMN 49:

Line 34, "Forth," should read --Fourth,--;
Line 37, "of" should be deleted; and
Line 64, "confluent" should read --confluence--.

COLUMN 50:

Line 9, "manufacture's" should read --manufacturer's--;
Line 24, "Current Proto-" should be italicized;
Line 25, "cols in Neuroscience" should be italicized;
Line 28, "The Mouse Brain in Stereotaxic Coor-" should be italicized; and
Line 29, "dinates" should be italicized.

COLUMN 51:

Line 2, "confluent" should read --confluence--.

COLUMN 52:

Line 8, "Di1-labeled" should read --DiI-labeled--;
Line 20, "confluent" should read --confluence--; and
Line 38, "are" should read --is--.

COLUMN 53:

Line 3, "confluent" should read --confluence--;
Line 16, "are" should read --is--;
Line 43, "confluent" should read --confluence--; and
Line 46, "exchange" should read --exchanged--.

COLUMN 54:

Line 56, "(10mmol ℓ" should read --(10mmol/ℓ--;
Line 58, "sequence" should read --Sequence--; and
Line 65, "second" should read --seconds--.

COLUMN 55:

Line 23, "confluent" should read --confluence--;
Line 32, "mutation" should read --*Mutation*--;
Line 48, "was" should read --were--; and
Line 53, "confluent" should read --confluence--.

COLUMN 56:

Line 41, "confluent" should read --confluence--;
Line 53, "confluent" should read --confluence--; and
Line 65, "antiblody." should read --antibody.--.

COLUMN 57:

Line 17, "confluent" should read --confluence--; and
Line 18, "was" should read --were--.

COLUMN 58:

Line 28, "VAchT" should read --VAChT--; and
Line 48, "Anti-VAchT" should read --Anti-VAChT--.

COLUMN 59:

Line 25, "confluent" should read --confluence--; and
Line 61, "plates" should read --plate--.

COLUMN 60:

Line 4, "Tndus-" should read --Indus- --;
Line 38, "media" should read --Media--;
Line 43, "plates," should read --plate,--; and
Line 57, "organism" should read --Organism-- and "Instituted" should read --Institute--.

COLUMN 61:

Line 2, "matters" should read --matter.--;
Line 12, "confluent" should read --confluence--; and
Line 20, "A-MEM" should read --α-MEM--.

COLUMN 62:

Line 13, "Klotho" should be italicized; and
Line 28, "one" should read --one of--.

COLUMN 64:

Line 50, "claim 1, 2 or 3," should read --claims 1-3,--;
Line 53, "claim 1, 2 or 3," should read --claims 1-3,--; and
Line 61, "claim 1, 2 or 3," should read --claims 1-3,--.

COLUMN 65:

Line 1, "claim 1, 2 or 3," should read --claims 1-3,--.